(12) United States Patent
Bondy et al.

(10) Patent No.: US 9,012,441 B2
(45) Date of Patent: Apr. 21, 2015

(54) THERAPEUTIC COMPOUNDS

(71) Applicant: Gilead Sciences, Inc., Foster City, CA (US)

(72) Inventors: Steven S. Bondy, Danville, CA (US); Carina E. Cannizzaro, Foster City, CA (US); Chien-Hung Chou, Livermore, CA (US); Yunfeng Eric Hu, San Mateo, CA (US); John O. Link, San Francisco, CA (US); Qi Liu, Union City, CA (US); Scott D. Schroeder, Union City, CA (US); Winston C. Tse, Redwood City, CA (US); Jennifer R. Zhang, Union City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 14/151,762

(22) Filed: Jan. 9, 2014

(65) Prior Publication Data

US 2014/0221417 A1      Aug. 7, 2014

Related U.S. Application Data

(60) Provisional application No. 61/750,759, filed on Jan. 9, 2013.

(51) Int. Cl.
| | |
|---|---|
| C07D 487/04 | (2006.01) |
| C07D 513/04 | (2006.01) |
| A61K 31/00 | (2006.01) |
| C07D 471/14 | (2006.01) |

(52) U.S. Cl.
CPC ............ *C07D 513/04* (2013.01); *C07D 471/14* (2013.01); *C07D 487/04* (2013.01)

(58) Field of Classification Search
USPC ................ 540/455, 456, 457, 458, 460, 461; 514/183, 285, 286, 287, 288, 405, 410
See application file for complete search history.

(56) References Cited

U.S. PATENT DOCUMENTS

| | | |
|---|---|---|
| 2013/0165489 A1 | 6/2013 | Cocklin et al. |
| 2014/0142085 A1 | 5/2014 | Bondy et al. |
| 2014/0221346 A1 | 8/2014 | Halcomb et al. |
| 2014/0221347 A1 | 8/2014 | Brizgys et al. |
| 2014/0221421 A1 | 8/2014 | Bondy et al. |

FOREIGN PATENT DOCUMENTS

| | | |
|---|---|---|
| WO | WO-2009/005677 A2 | 1/2009 |
| WO | WO-2009/005677 A3 | 1/2009 |
| WO | WO-2009/010804 A1 | 1/2009 |
| WO | WO-2009/062285 A1 | 5/2009 |
| WO | WO-2010/130034 A1 | 11/2010 |
| WO | WO-2012/003497 A1 | 1/2012 |
| WO | WO-2012/003498 A1 | 1/2012 |
| WO | WO-2012/145728 A1 | 10/2012 |
| WO | WO-2013/006792 A1 | 1/2013 |
| WO | WO-2013/159064 A1 | 10/2013 |
| WO | WO-2014/016358 A1 | 1/2014 |

OTHER PUBLICATIONS

Berge, S.M. et al. (Jan. 1977). "Pharmaceutical Salts," *J. Pharma. Sci.* 66(1):1-19.
Hammer, S. et al. (Aug. 6, 2008). "Antiretroviral Treatment of Adult HIV Infection. 2008 Recommendations of the International AIDS Society: USA Panel," *JAMA* 300(5):555-570.
International Search Report mailed on Apr. 11, 2014 for PCT Patent Application No. PCT/US2014/010937, filed on Jan. 9, 2014, three pages.
Lemke, C.T. et al. (Jun. 2012). "Distinct Effects of Two HIV-1 Capsid Assembly Inhibitor Families That Bind the Same Site Within the N-Terminal Domain of the Viral CA Protein," *J. Virol.* 86(12):6643-6655.
Smith, R.J. et al. (Feb. 5, 2010; e-pub. Jan. 14, 2010). "Evolutionary Dynamics of Complex Networks of HIV Drug-Resistant Strains: The Case of San Francisco," *Science* 327(5966):697-701.
Taiwo, B. (Sep. 2009; e-pub. Jan. 10, 2009). "Understanding Transmitted HIV Resistance through the Experience in the USA," *Int'l J. of Infectious Diseases* 13(5):552-559.
Written Opinion of the International Searching Authority mailed on Apr. 11, 2014 for PCT Patent Application No. PCT/US2014/010937, filed on Jan. 9, 2014, six pages.

*Primary Examiner* — Bruck Kifle
(74) *Attorney, Agent, or Firm* — Timothy A. Marquart

(57) ABSTRACT

Compounds of formula I:

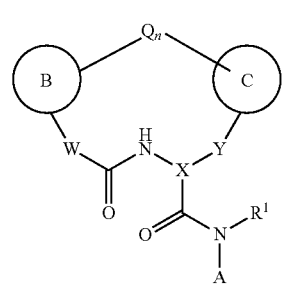

or salts thereof are disclosed. Also disclosed are pharmaceutical compositions comprising a compound of formula I, processes for preparing compounds of formula I, intermediates useful for preparing compounds of formula I and therapeutic methods for treating a Retroviridae viral infection including an infection caused by the HIV virus.

17 Claims, No Drawings

THERAPEUTIC COMPOUNDS

CROSS REFERENCE TO RELATED APPLICATION

This application claims the benefit of and priority to U.S. Provisional Application Ser. No. 61/750,759, filed Jan. 9, 2013, the disclosure of which is hereby incorporated by reference in its entirety.

BACKGROUND

Positive-single stranded RNA viruses comprising the Retroviridae family include those of the subfamily Orthoretrovirinae and genera *Alpharetrovirus, Betaretrovirus, Gamaretrovirus, Deltaretrovirus, Epsilonretrovirus, Lentiviruss*, and *Spumavirus* which cause many human and animal diseases. Among the *Lentivirus*, HIV-1 infection in humans leads to depletion of T helper cells and immune dysfunction, producing immunodeficiency and vulnerability to opportunistic infections. Treating HIV-1 infections with highly active antiretroviral therapies (HAART) has proven to be effective at reducing viral load and significantly delaying disease progression (Hammer, S. M., et al.; *JAMA* 2008, 300: 555-570). However, these treatments do lead to the emergence of HIV strains that are resistant to current therapies (Taiwo, B., *International Journal of Infectious Diseases* 2009, 13:552-559; Smith, R. J., et al., *Science* 2010, 327:697-701). Therefore, there is a pressing need to discover new antiretroviral agents that are active against emerging drug-resistant HIV variants.

SUMMARY

Provided herein are compounds and methods for the treatment of a viral infection. One embodiment provides a compound of formula I:

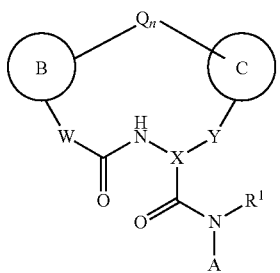

wherein:

A is aryl, heteroaryl, heterocycle, aryl($C_1$-$C_4$)alkyl- or heteroaryl($C_1$-$C_4$)alkyl- wherein any aryl, heteroaryl, heterocycle, aryl($C_1$-$C_4$)alkyl- or heteroaryl($C_1$-$C_4$)alkyl- of A is optionally substituted with one or more (e.g., 1, 2, 3, 4 or 5) $Z^1$ groups;

B is aryl or heteroaryl, wherein any aryl or heteroaryl of B is optionally substituted with one or more (e.g., 1, 2, 3, 4 or 5) $Z^2$ groups, and wherein Q and W are connected to adjacent ring atoms of B;

C is phenyl, 5-membered heteroaryl or 6-membered heteroaryl, wherein any phenyl, 5-membered heteroaryl or 6-membered heteroaryl of C is optionally substituted with one or more (e.g. 1, 2, 3 or 4) $Z^3$ groups, and wherein Q and Y are connected to adjacent ring atoms of C, or Q and Y are connected to the first and third atom of three consecutive ring atoms of C;

each Q is independently selected from —C($R^{2a}$)$_2$—O—, —$NR^{1a}$—, —S—, —C(=O)—, —S(=O)— and —S(=O)$_2$—, or two adjacent Q groups taken together can be —$CR^{2b}$=$CR^{2b}$—;

W is —$CH_2$—;

X is CH or N;

Y is —$CH_2$—;

n is 1, 2, 3, 4 or 5;

$R^1$ is selected from ($C_1$-$C_6$)alkyl, ($C_3$-$C_7$)carbocycle, ($C_3$-$C_7$)carbocycle($C_1$-$C_6$)alkyl-, aryl($C_1$-$C_6$)alkyl- and heteroaryl($C_1$-$C_6$)alkyl-;

$R^{1a}$ is H or ($C_1$-$C_4$)alkyl, each $R^{2a}$ is independently H, halogen or ($C_1$-$C_4$)alkyl, and each $R^{2b}$ is independently H or ($C_1$-$C_4$)alkyl, or one $R^{2a}$ together with an adjacent Q group forms a three membered carbocycle;

each $Z^1$ is independently selected from ($C_1$-$C_4$)alkyl, ($C_2$-$C_4$)alkenyl, ($C_2$-$C_4$)alkynyl, —CN, —$OR_{n1}$, —OC(O)$R_{p1}$, —OC(O)$NR_{q1}R_{r1}$, —$SR_{n1}$, —S(O)$R_{p1}$, —S(O)$_2$OH, —S(O)$_2R_{p1}$, —S(O)$_2NR_{q1}R_{r1}$, —$NR_{q1}R_{r1}$, —$NR_{n1}COR_{p1}$, —$NR_{n1}CO_2R_{p1}$, —$NR_{n1}CONR_{q1}$, —$NR_{n1}S(O)_2R_{p1}$, —$NR_{n1}S(O)_2OR_{p1}$, —$NR_{n1}S(O)_2NR_{q1}OR_{r1}$, $NO_2$, —C(O)$R_{n1}$, —C(O)$OR_{n1}$ and —C(O)$NR_{q1}R_{r1}$, wherein any ($C_1$-$C_4$)alkyl, ($C_2$-$C_4$)alkenyl or ($C_2$-$C_4$)alkynyl of $Z^1$ is optionally substituted with one or more (e.g., 1, 2, 3, 4 or 5) $Z^{1a}$ groups;

each $Z^{1a}$ is independently selected from halogen, —CN, —$OR_{n2}$, —OC(O)$R_{p2}$, —OC(O)$NR_{q2}R_{r2}$, —$SR_{n2}$, (O)$R_{p2}$, —S(O)$_2$OH, (O)$_2R_{p2}$, (O)$_2NR_{q2}R_{r2}$, —$NR_{q2}R_{r2}$, —$NR_{n2}COR_{p2}$, —$NR_{n2}CO_2R_{p2}$, —$NR_{n2}CONR_{q2}R_{r2}$, —$NR_{n2}S(O)_2R_{p2}$, —$NR_{n2}S(O)_2OR_{p2}$, —$NR_{n2}S(O)_2NR_{q2}R_{r2}$, $NO_2$, —C(O)$R_{n2}$, —C(O)$OR_{n2}$ and —C(O)$NR_{q2}R_{r2}$;

each $Z^{1b}$ is independently selected from ($C_1$-$C_4$)alkyl, ($C_2$-$C_4$)alkenyl and ($C_2$-$C_4$)alkynyl;

each $R_{n1}$ is independently selected from H, ($C_1$-$C_4$)alkyl, ($C_2$-$C_4$)alkenyl, ($C_2$-$C_4$)alkynyl, wherein any ($C_1$-$C_4$)alkyl, ($C_2$-$C_4$)alkenyl or ($C_2$-$C_4$)alkynyl of $R_{n1}$ is optionally substituted with one or more (e.g., 1, 2, 3, 4 or 5) $Z^{1a}$ groups;

each $R_{p1}$ is independently selected from ($C_1$-$C_4$)alkyl, ($C_1$-$C_4$)haloalkyl, ($C_2$-$C_4$)alkenyl, ($C_2$-$C_4$)alkynyl wherein any ($C_1$-$C_4$)alkyl, ($C_2$-$C_4$)alkenyl or ($C_2$-$C_4$)alkynyl of $R_{p1}$ is optionally substituted with one or more (e.g., 1, 2, 3, 4 or 5) $Z^{1a}$ groups;

$R_{q1}$ and $R_{r1}$ are each independently selected from H, ($C_1$-$C_4$)alkyl, ($C_2$-$C_4$)alkenyl, ($C_2$-$C_4$)alkynyl, wherein any ($C_1$-$C_4$)alkyl, ($C_2$-$C_4$)alkenyl or ($C_2$-$C_4$)alkynyl of $R_{q1}$ or $R_{r1}$ is optionally substituted with one or more (e.g., 1, 2, 3, 4 or 5) $Z^{1a}$ groups, or $R_{q1}$ and $R_{r1}$ together with the nitrogen to which they are attached form a 5, 6 or 7-membered heterocycle, wherein the 5, 6 or 7-membered heterocycle is optionally substituted with one or more (e.g., 1, 2, 3, 4 or 5) $Z^{1a}$ or $Z^{1b}$ groups;

each $R_{n2}$ is independently selected from H, ($C_1$-$C_4$)alkyl, ($C_2$-$C_4$)alkenyl, ($C_2$-$C_4$)alkynyl, ($C_1$-$C_4$)haloalkyl and ($C_1$-$C_4$)heteroalkyl;

each $R_{p2}$ is independently selected from ($C_1$-$C_4$)alkyl, ($C_2$-$C_4$)alkenyl, ($C_2$-$C_4$)alkynyl, ($C_1$-$C_4$)haloalkyl and ($C_1$-$C_4$)heteroalkyl;

$R_{q2}$ and $R_{r2}$ are each independently selected from H, ($C_1$-$C_4$)alkyl, ($C_2$-$C_4$)alkenyl, ($C_2$-$C_4$)alkynyl, ($C_1$-$C_4$)haloalkyl and ($C_1$-$C_4$)heteroalkyl, or $R_{q2}$ and $R_{r2}$ together with the nitrogen to which they are attached form a 5, 6 or 7-membered heterocycle;

each $Z^2$ is independently selected from ($C_1$-$C_4$)alkyl, ($C_2$-$C_4$)alkenyl, ($C_2$-$C_4$)alkynyl, halogen, —CN, —$OR_{n3}$, —OC(O)$R_{p3}$, —OC(O)$NR_{q3}R_{r3}$, —$SR_{n3}$, —S(O)$R_{p3}$, —S(O)$_2$OH, —S(O)$_2R_{p3}$, —S(O)$_2NR_{q3}R_{r3}$, —$NR_{q3}R_{r3}$, —$NR_{n3}COR_{p3}$, —$NR_{n3}CO_2R_{p3}$, —$NR_{n3}CONR_{q3}R_{r3}$, —NR$_{n3}$S(O)$_2$R$_{p3}$, —NR$_{n3}$S(O)$_2$OR$_{p3}$, —NR$_{n3}$S(O)$_2$NR$_{q3}$R$_{r3}$, NO$_2$, —C(O)R$_{n3}$, —C(O)OR$_{n3}$ and —C(O)NR$_{q3}$R$_{r3}$, wherein any (C$_1$-C$_4$)alkyl, (C$_2$-C$_4$)alkenyl or (C$_2$-C$_4$)alkynyl of Z$^2$ is optionally substituted with one or more (e.g., 1, 2, 3, 4 or 5) Z$^{2a}$ groups;

each Z$^{2a}$ is independently selected from halogen, —CN, —OR$_{n4}$, —OC(O)R$_{p4}$, —OC(O)NR$_{q4}$R$_{r4}$, —SR$_{n4}$, —S(O)R$_{p4}$, —S(O)$_2$OH, —S(O)$_2$R$_{p4}$, —S(O)$_2$NR$_{q4}$R$_{r4}$, —NR$_{q4}$R$_{r4}$, —NR$_{n4}$COR$_{p4}$, —NR$_{n4}$CO$_2$R$_{p4}$, —NR$_{n4}$CONR$_{q4}$R$_{r4}$, —NR$_{n4}$S(O)$_2$R$_{p4}$, —NR$_{n4}$S(O)$_2$OR$_{p4}$, —NR$_{n4}$S(O)$_2$NR$_{q4}$R$_{r4}$, NO$_2$, —C(O)R$_{n4}$, —C(O)OR$_{n4}$ and —C(O)NR$_{q4}$R$_{r4}$;

each Z$^{2b}$ is independently selected from (C$_1$-C$_4$)alkyl, (C$_2$-C$_4$)alkenyl and (C$_2$-C$_4$)alkynyl;

each R$_{n3}$ is independently selected from H, (C$_1$-C$_4$)alkyl, (C$_2$-C$_4$)alkenyl, (C$_2$-C$_4$)alkynyl, wherein any (C$_1$-C$_4$)alkyl, (C$_2$-C$_4$)alkenyl or (C$_2$-C$_4$)alkynyl of R$_{n3}$ is optionally substituted with one or more (e.g., 1, 2, 3, 4 or 5) Z$^{2a}$ groups;

each R$_{p3}$ is independently selected from (C$_1$-C$_4$)alkyl, (C$_1$-C$_4$)haloalkyl, (C$_2$-C$_4$)alkenyl, (C$_2$-C$_4$)alkynyl, wherein any (C$_1$-C$_4$)alkyl, (C$_2$-C$_4$)alkenyl or (C$_2$-C$_4$)alkynyl of R$_{p3}$ is optionally substituted with one or more (e.g., 1, 2, 3, 4 or 5) Z$^{2a}$ groups;

R$_{q3}$ and R$_{r3}$ are each independently selected from H, (C$_1$-C$_4$)alkyl, (C$_2$-C$_4$)alkenyl, (C$_2$-C$_4$)alkynyl, wherein any (C$_1$-C$_4$)alkyl, (C$_2$-C$_4$)alkenyl or (C$_2$-C$_4$)alkynyl of R$_{q3}$ or R$_{r3}$ is optionally substituted with one or more (e.g., 1, 2, 3, 4 or 5) Z$^{2a}$ groups, or R$_{q3}$ and R$_{r3}$ together with the nitrogen to which they are attached form a 5, 6 or 7-membered heterocycle, wherein the 5, 6 or 7-membered heterocycle is optionally substituted with one or more (e.g., 1, 2, 3, 4 or 5) Z$^{2a}$ or Z$^{2b}$ groups;

each R$_{n4}$ is independently selected from H, (C$_1$-C$_4$)alkyl, (C$_2$-C$_4$)alkenyl, (C$_2$-C$_4$)alkynyl, (C$_3$-C$_7$)carbocycle, heterocycle, heteroaryl, aryl, haloaryl, haloheteroaryl, haloheterocycle, (C$_1$-C$_4$)haloalkyl and (C$_1$-C$_4$)heteroalkyl;

each R$_{p4}$ is independently selected from (C$_1$-C$_4$)alkyl, (C$_2$-C$_4$)alkenyl, (C$_2$-C$_4$)alkynyl, (C$_3$-C$_7$)carbocycle, heterocycle, heteroaryl, aryl, haloaryl, haloheteroaryl, haloheterocycle, (C$_1$-C$_4$)haloalkyl and (C$_1$-C$_4$)heteroalkyl;

R$_{q4}$ and R$_{r4}$ are each independently selected from H, (C$_1$-C$_4$)alkyl, (C$_2$-C$_4$)alkenyl, (C$_2$-C$_8$)alkynyl, (C$_3$-C$_7$)carbocycle, heterocycle, heteroaryl, aryl, haloaryl, haloheteroaryl, haloheterocycle, (C$_1$-C$_4$)haloalkyl and (C$_1$-C$_4$)heteroalkyl, or R$_{q4}$ and R$_{r4}$ together with the nitrogen to which they are attached form a 5, 6 or 7-membered heterocycle;

each Z$^3$ is independently selected from (C$_1$-C$_4$)alkyl, halogen, —CN, —OR$_{n5}$, —NR$_{n5}$COR$_{p5}$, —C(O)R$_{n5}$, and —C(O)NR$_{q5}$R$_{r5}$;

each R$_{n5}$ is independently selected from H, (C$_1$-C$_4$)alkyl, (C$_1$-C$_4$)haloalkyl and (C$_1$-C$_4$)heteroalkyl;

each R$_{p5}$ is independently selected from (C$_1$-C$_4$)alkyl, (C$_2$-C$_4$)alkenyl, (C$_2$-C$_4$)alkynyl, (C$_1$-C$_4$)haloalkyl and (C$_1$-C$_4$)heteroalkyl; and R$_{q5}$ and R$_{r5}$ are each independently selected from H, (C$_1$-C$_4$)alkyl, (C$_2$-C$_4$)alkenyl, (C$_2$-C$_4$)alkynyl, (C$_1$-C$_4$)haloalkyl and (C$_1$-C$_4$)heteroalkyl, or R$_{q5}$ and R$_{r5}$ together with the nitrogen to which they are attached form a 5, 6 or 7-membered heterocycle;

or a salt thereof. In certain embodiments, a salt is a pharmaceutically acceptable salt.

One embodiment provides a pharmaceutical composition comprising a compound of formula I or a pharmaceutically acceptable salt thereof, and a pharmaceutically acceptable carrier.

One embodiment provides a method for treating a Retroviridae viral infection (e.g., an HIV viral infection) in a mammal (e.g., a human), comprising administering a compound of formula I, or a pharmaceutically acceptable salt thereof, to the mammal.

One embodiment provides a method for inhibiting the proliferation of the HIV virus, treating AIDS or delaying the onset of AIDS or ARC symptoms in a mammal (e.g., a human), comprising administering a compound of formula I, or a pharmaceutically acceptable salt thereof, to the mammal.

One embodiment provides a method for treating an HIV infection in a mammal (e.g., a human), comprising administering a compound of formula I, or a pharmaceutically acceptable salt thereof, to the mammal.

One embodiment provides a method for treating an HIV infection in a mammal (e.g., a human), comprising administering to the mammal in need thereof a therapeutically effective amount of a compound of formula I, or a pharmaceutically acceptable salt thereof, in combination with a therapeutically effective amount of one or more additional therapeutic agents selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, and other drugs for treating HIV, and combinations thereof.

One embodiment provides a compound of formula I, or a pharmaceutically acceptable salt thereof for use in medical therapy (e.g., for use in treating a Retroviridae viral infection (e.g., an HIV viral infection) or the proliferation of the HIV virus or AIDS or delaying the onset of AIDS or ARC symptoms in a mammal (e.g., a human)).

One embodiment provides a compound of formula I, or a pharmaceutically acceptable salt thereof for use in the manufacture of a medicament for treating a Retroviridae viral infection (e.g., an HIV viral infection) or the proliferation of the HIV virus or AIDS or delaying the onset of AIDS or ARC symptoms in a mammal (e.g., a human).

One embodiment provides a compound of formula I, or a pharmaceutically acceptable salt thereof, for use in the prophylactic or therapeutic treatment of the proliferation of a Retroviridae virus, an HIV virus or AIDS or for use in the therapeutic treatment of delaying the onset of AIDS or ARC symptoms.

One embodiment provides a compound of formula I, or a pharmaceutically acceptable salt thereof, for use in the prophylactic or therapeutic treatment of a Retroviridae virus infection (e.g., an HIV virus infection).

One embodiment provides the use of a compound of formula I, or a pharmaceutically acceptable salt thereof, for the manufacture of a medicament for a Retroviridae virus infection (e.g., an HIV virus infection) in a mammal (e.g., a human).

One embodiment provides processes and intermediates disclosed herein that are useful for preparing compounds of formula I or salts thereof. In certain embodiments, a salt is a pharmaceutically acceptable salt.

Other embodiments, objects, features and advantages will be set forth in the detailed description of the embodiments that follows, and in part will be apparent from the description, or may be learned by practice, of the claimed invention. These objects and advantages will be realized and attained by the processes and compositions particularly pointed out in the written description and claims hereof. The foregoing Summary has been made with the understanding that it is to be considered as a brief and general synopsis of some of the embodiments disclosed herein, is provided solely for the benefit and convenience of the reader, and is not intended to limit in any manner the scope, or range of equivalents, to which the appended claims are lawfully entitled.

DETAILED DESCRIPTION

While the present invention is capable of being embodied in various forms, the description below of several embodiments is made with the understanding that the present disclosure is to be considered as an exemplification of the claimed subject matter, and is not intended to limit the appended claims to the specific embodiments illustrated. The headings used throughout this disclosure are provided for convenience only and are not to be construed to limit the claims in any way. Embodiments illustrated under any heading may be combined with embodiments illustrated under any other heading.

DEFINITIONS

Unless stated otherwise, the following terms and phrases as used herein are intended to have the following meanings:

When trade names are used herein, applicants intend to independently include the tradename product and the active pharmaceutical ingredient(s) of the tradename product.

"Alkyl" is a straight or branched saturated hydrocarbon. For example, an alkyl group can have 1 to 8 carbon atoms (i.e., ($C_1$-$C_8$)alkyl) or 1 to 6 carbon atoms (i.e., ($C_1$-$C_6$ alkyl) or 1 to 4 carbon atoms. Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —CH($CH_3$)$CH_2CH_3$), 2-methyl-2-propyl t-butyl, —$C(CH_3)_3$), 1-pentyl (n-pentyl, —$CH_2CH_2CH_2CH_2CH_3$), 2-pentyl (—CH($CH_3$)$CH_2CH_2CH_3$), 3-pentyl (—CH($CH_2CH_3$)$_2$), 2-methyl-2-butyl (—C($CH_3$)$_2$$CH_2CH_3$), 3-methyl-2-butyl (—CH($CH_3$)CH($CH_3$)$_2$), 3-methyl-1-butyl (—$CH_2CH_2$CH($CH_3$)$_2$), 2-methyl-1-butyl (—$CH_2$CH($CH_3$)$CH_2CH_3$), 1-hexyl (—$CH_2CH_2CH_2CH_2CH_2CH_3$), 2-hexyl (—CH($CH_3$)$CH_2CH_2CH_2CH_3$), 3-hexyl (—CH($CH_2CH_3$)($CH_2CH_2CH_3$)), 2-methyl-2-pentyl (—C($CH_3$)$_2$$CH_2CH_2CH_3$), 3-methyl-2-pentyl (—CH($CH_3$)CH($CH_3$)$CH_2CH_3$), 4-methyl-2-pentyl (—CH($CH_3$)$CH_2$CH($CH_3$)$_2$), 3-methyl-3-pentyl (—C($CH_3$)($CH_2CH_3$)$_2$), 2-methyl-3-pentyl (—CH($CH_2CH_3$)CH($CH_3$)$_2$), 2,3-dimethyl-2-butyl (—C($CH_3$)$_2$CH($CH_3$)$_2$), 3,3-dimethyl-2-butyl (—CH($CH_3$)C($CH_3$)$_3$, and octyl (—($CH_2$)$_7$$CH_3$).

"Alkenyl" is a straight or branched hydrocarbon with at least one site of unsaturation, e.g. a carbon-carbon, $sp^2$ double bond. For example, an alkenyl group can have 2 to 8 carbon atoms (i.e., $C_2$-$C_8$ alkenyl), or 2 to 6 carbon atoms (i.e., $C_2$-$C_6$ alkenyl). Examples of suitable alkenyl groups include, but are not limited to, ethylene or vinyl (—CH=$CH_2$), allyl (—$CH_2$CH=$CH_2$) and 5-hexenyl (—$CH_2CH_2CH_2CH_2$CH=$CH_2$).

"Alkynyl" is a straight or branched hydrocarbon with at least one site of unsaturation, i.e. a carbon-carbon, sp triple bond. For example, an alkynyl group can have 2 to 8 carbon atoms (i.e., $C_2$-$C_8$ alkyne,), or 2 to 6 carbon atoms (i.e., $C_2$-$C_6$ alkynyl). Examples of suitable alkynyl groups include, but are not limited to, acetylenic (—C≡CH), propargyl (—$CH_2$C≡CH), and the like.

The term "halo" or "halogen" as used herein refers to fluoro, chloro, bromo and iodo.

The term "haloalkyl" as used herein refers to an alkyl as defined herein, wherein one or more hydrogen atoms are each replaced by a halo substituent. For example, a ($C_1$-$C_6$)haloalkyl is a ($C_1$-$C_6$)alkyl wherein one or more of the hydrogen atoms have been replaced by a halo substituent. Such a range includes one halo substituent on the alkyl group to complete halogenation of the alkyl group.

The term "heteroalkyl" as used herein refers to an alkyl as defined herein, wherein one or more of the carbon atoms of the alkyl are replaced by an O, S, or $NR_q$, (or if the carbon atom being replaced is a terminal carbon with an OH, SH or $NR_{q2}$) wherein each $R_q$ is independently H or ($C_1$-$C_6$)alkyl.

The term "aryl" as used herein refers to a single all carbon aromatic ring or a multiple condensed all carbon ring system wherein at least one of the rings is aromatic. For example, an aryl group can have 6 to 20 carbon atoms, 6 to 14 carbon atoms, or 6 to 12 carbon atoms. Aryl includes a phenyl radical. Aryl also includes multiple condensed ring systems (e.g., ring systems comprising 2, 3 or 4 rings) having about 9 to 20 carbon atoms in which at least one ring is aromatic and wherein the other rings may be aromatic or not aromatic (i.e., carbocycle). Such multiple condensed ring systems may be optionally substituted with one or more (e.g., 1, 2 or 3) oxo groups on any carbocycle portion of the multiple condensed ring system. The rings of the multiple condensed ring system can be connected to each other via fused, spiro and bridged bonds when allowed by valency requirements. It is to be understood that the point of attachment of a multiple condensed ring system, as defined above, can be at any position of the ring system including an aromatic or a carbocycle portion of the ring. Typical aryl groups include, but are not limited to, phenyl, indenyl, naphthyl, 1,2,3,4-tetrahydronaphthyl, anthracenyl, and the like.

"Arylalkyl" refers to an alkyl radical as defined herein in which one of the hydrogen atoms bonded to a carbon atom is replaced with an aryl radical as described herein (i.e., an aryl-alkyl-moiety). The alkyl group of the "arylalkyl" is typically 1 to 6 carbon atoms (i.e. aryl($C_1$-$C_6$)alkyl). Arylalkyl groups include, but are not limited to, benzyl, 2-phenylethan-1-yl, 1-phenylpropan-1-yl, naphthylmethyl, 2-naphthylethan-1-yl and the like.

The term "heteroaryl" as used herein refers to a single aromatic ring that has at least one atom other than carbon in the ring, wherein the atom is selected from the group consisting of oxygen, nitrogen and sulfur; the term also includes multiple condensed ring systems that have at least one such aromatic ring, which multiple condensed ring systems are further described below. Thus, the term includes single aromatic rings of from about 1 to 6 carbon atoms and about 1-4 heteroatoms selected from the group consisting of oxygen, nitrogen and sulfur in the rings. The sulfur and nitrogen atoms may also be present in an oxidized form provided the ring is aromatic. Such rings include but are not limited to pyridyl, pyrimidinyl, oxazolyl or furyl. The term also includes multiple condensed ring systems (e.g., ring systems comprising 2, 3 or 4 rings) wherein a heteroaryl group, as defined above, can be condensed with one or more rings selected from heteroaryls (to form for example a naphthyridinyl such as 1,8-naphthyridinyl), heterocycles, (to form for example a 1,2,3,4-tetrahydronaphthyridinyl such as 1,2,3,4-tetrahydro-1,8-naphthyridinyl), carbocycles (to form for example 5,6,7,8-tetrahydroquinolyl) and aryls (to form for example indazolyl) to form the multiple condensed ring system. Thus, a heteroaryl (a single aromatic ring or multiple condensed ring system) has about 1-20 carbon atoms and about 1-6 heteroatoms within the heteroaryl ring. Such multiple condensed ring systems may be optionally substituted with one or more (e.g., 1, 2, 3 or 4) oxo groups on the carbocycle or heterocycle portions of the condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heteroaryl) can be at any position of the multiple condensed ring system including a heteroaryl, heterocycle, aryl or carbocycle portion of the multiple condensed ring system and at any suitable atom of the multiple condensed ring system including a carbon atom and heteroatom (e.g., a nitrogen). Exemplary heteroaryls include but are not limited to pyridyl, pyrrolyl, pyrazinyl, pyrimidinyl, pyridazinyl, pyrazolyl, thienyl, indolyl, imidazolyl, oxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl and thianaphthenyl.

The term "heterocyclyl" or "heterocycle" as used herein refers to a single saturated or partially unsaturated ring that has at least one atom other than carbon in the ring, wherein the atom is selected from the group consisting of oxygen, nitrogen and sulfur; the term also includes multiple condensed ring systems that have at least one such saturated or partially unsaturated ring, which multiple condensed ring systems are further described below. Thus, the term includes single saturated or partially unsaturated rings (e.g., 3, 4, 5, 6 or 7-membered rings) from about 1 to 6 carbon atoms and from about 1 to 3 heteroatoms selected from the group consisting of oxygen, nitrogen and sulfur in the ring. The ring may be substituted with one or more (e.g., 1, 2 or 3) oxo groups and the sulfur and nitrogen atoms may also be present in their oxidized forms. Such rings include but are not limited to azetidinyl, tetrahydrofuranyl or piperidinyl. The term "heterocycle" also includes multiple condensed ring systems (e.g., ring systems comprising 2, 3 or 4 rings) wherein a single heterocycle ring (as defined above) can be condensed with one or more groups selected from heterocycles (to form for example a decahydronapthyridinyl), carbocycles (to form for example a decahydroquinolyl) and aryls to form the multiple condensed ring system. Thus, a heterocycle (a single saturated or single partially unsaturated ring or multiple condensed ring system) has about 2-20 carbon atoms and 1-6 heteroatoms within the heterocycle ring. Such multiple condensed ring systems may be optionally substituted with one or more (e.g., 1, 2, 3 or 4) oxo groups on the carbocycle or heterocycle portions of the multiple condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heterocycle) can be at any position of the multiple condensed ring system including a heterocycle, aryl and carbocycle portion of the ring. It is also to be understood that the point of attachment for a heterocycle or heterocycle multiple condensed ring system can be at any suitable atom of the heterocycle or heterocycle multiple condensed ring system including a carbon atom and a heteroatom (e.g., a nitrogen). Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl and 1,4-benzodioxanyl.

"Heteroarylalkyl" refers to an alkyl radical as defined herein in which one of the hydrogen atoms bonded to a carbon atom is replaced with a heteroaryl radical as described herein (i.e., a heteroaryl-alkyl-moiety). The alkyl group of the "heteroarylalkyl" is typically 1 to 6 carbon atoms (i.e. heteroaryl $(C_1-C_6)$alkyl). Heteroarylalkyl groups include, but are not limited to heteroaryl-$CH_2$—, heteroaryl-$CH(CH_3)$—, heteroaryl-$CH_2CH_2$—, 2-(heteroaryl)ethan-1-yl, and the like, wherein the "heteroaryl" portion includes any of the heteroaryl groups described above. One skilled in the art will also understand that the heteroaryl group can be attached to the alkyl portion of the heteroarylalkyl by means of a carbon-carbon bond or a carbon-heteroatom bond, with the proviso that the resulting group is chemically stable. Examples of heteroarylalkyls include by way of example and not limitation 5-membered sulfur, oxygen, and/or nitrogen containing heteroaryls such as thiazolylmethyl, 2-thiazolylethan-1-yl, imidazolylmethyl, oxazolylmethyl, thiadiazolylmethyl, etc., 6-membered sulfur, oxygen, and/or nitrogen containing heteroaryls such pyridinylmethyl, pyridizylmethyl, pyrimidylmethyl, pyrazinylmethyl, etc.

"Heterocyclylalkyl" refers to an alkyl radical as defined herein in which one of the hydrogen atoms bonded to a carbon atom is replaced with a heterocyclyl radical as described herein (i.e., a heterocyclyl-alkyl-moiety). The alkyl group of the "heterocyclylalkyl" is typically 1 to 6 carbon atoms (i.e. heterocyclyl$(C_1-C_6)$alkyl). Typical heterocyclylalkyl groups include, but are not limited to heterocyclyl-$CH_2$—, heterocyclyl-$CH(CH_3)$—, heterocyclyl-$CH_2CH_2$—, 2-(heterocyclyl)ethan-1-yl, and the like, wherein the "heterocyclyl" portion includes any of the heterocyclyl groups described above. One skilled in the art will also understand that the heterocyclyl group can be attached to the alkyl portion of the heterocyclyl alkyl by means of a carbon-carbon bond or a carbon-heteroatom bond, with the proviso that the resulting group is chemically stable. Examples of heterocyclylalkyls include by way of example and not limitation 5-membered sulfur, oxygen, and/or nitrogen containing heterocycles such tetrahydrofuranylmethyl and pyrroldinylmethyl, etc., and 6-membered sulfur, oxygen, and/or nitrogen containing heterocycles such as piperidinylmethyl, piperazinylmethyl, morpholinylmethyl, etc.

The term "carbocycle" or "carbocyclyl" refers to a single saturated (i.e., cycloalkyl) or a single partially unsaturated (e.g., cycloalkenyl, cycloalkadienyl, etc.) all carbon ring having 3 to 7 carbon atoms (i.e. $(C_3-C_7)$carbocycle). The term "carbocycle" or "carbocyclyl" also includes multiple condensed, saturated and partially unsaturated all carbon ring systems (e.g., ring systems comprising 2, 3 or 4 carbocyclic rings). Accordingly, carbocycle includes multicyclic carbocyles such as a bicyclic carbocycles (e.g., bicyclic carbocycles having about 6 to 12 carbon atoms such as bicyclo [3.1.0]hexane and bicyclo[2.1.1]hexane), and polycyclic carbocycles (e.g tricyclic and tetracyclic carbocycles with up to about 20 carbon atoms). The rings of the multiple condensed ring system can be connected to each other via fused, spiro and bridged bonds when allowed by valency requirements. For example, multicyclic carbocyles can be connected to each other via a single carbon atom to form a spiro connection (e.g., spiropentane, spiro[4,5]decane, etc), via two adjacent carbon atoms to form a fused connection (e.g., carbocycles such as decahydronaphthalene, norsabinane, norcarane) or via two non-adjacent carbon atoms to form a bridged connection (e.g., norbornane, bicyclo[2.2.2]octane, etc). The "carbocycle" or "carbocyclyl" can also be optionally substituted with one or more (e.g., 1, 2 or 3) oxo groups. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl and 1-cyclohex-3-enyl.

"Carbocyclylalkyl" refers to an alkyl radical as defined herein in which one of the hydrogen atoms bonded to a carbon atom is replaced with a carbocyclyl radical as described herein (i.e., a carbocyclyl-alkyl-moiety). The alkyl group of the "carbocyclylalkyl" is typically 1 to 6 carbon atoms (i.e. carbocyclyl($C_1$-$C_6$)alkyl). Typical carbocyclyl alkyl groups include, but are not limited to carbocyclyl-$CH_2$—, carbocyclyl-$CH(CH_3)$—, carbocyclyl-$CH_2CH_2$—, 2-(carbocyclyl) ethan-1-yl, and the like, wherein the "carbocyclyl" portion includes any of the carbocyclyl groups described above.

The term "haloaryl" as used herein refers to an aryl as defined herein, wherein one or more hydrogen atoms of the aryl are each replaced independently by a halo substituent. Such a range includes one halo substituent on the aryl group to complete halogenation of the aryl group.

The term "haloheteroaryl" as used herein refers to a heteroaryl as defined herein, wherein one or more hydrogen atoms of the heteroaryl are each replaced independently by a halo substituent. Such a range includes one halo substituent on the heteroaryl group to complete halogenation of the heteroaryl group.

The term "haloheterocycle" as used herein refers to a heterocycle as defined herein, wherein one or more hydrogen atoms of the heterocycle are each replaced independently by a halo substituent. Such a range includes one halo substituent on the heterocycle group to complete halogenation of the heterocycle group.

One skilled in the art will recognize that substituents and other moieties of the compounds of formula I should be selected in order to provide a compound which is sufficiently stable to provide a pharmaceutically useful compound which can be formulated into an acceptably stable pharmaceutical composition. Compounds of formula I which have such stability are contemplated as falling within the scope of the present invention.

The modifier "about" used in connection with a quantity is inclusive of the stated value and has the meaning dictated by the context (e.g., includes the degree of error associated with measurement of the particular quantity). The word "about" may also be represented symbolically by "~" in the context of a chemical measurement (e.g., ~50 mg or pH~7).

The term "treatment" or "treating," to the extent it relates to a disease or condition includes preventing the disease or condition from occurring, inhibiting the disease or condition, eliminating the disease or condition, and/or relieving one or more symptoms of the disease or condition.

Stereoisomers

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York.

The term "chiral" refers to molecules which have the property of non-superimposability of the mirror image partner, while the term "achiral" refers to molecules which are superimposable on their minor image partner.

The term "stereoisomers" refers to compounds which have identical chemical constitution, but differ with regard to the arrangement of the atoms or groups in space.

"Diastereomer" refers to a stereoisomer with two or more centers or axes of chirality and whose molecules are not mirror images of one another. Diastereomers typically have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable minor images of one another.

The compounds disclosed herein may have chiral centers, e.g., chiral carbon atoms. Such compounds thus include racemic mixtures of all stereoisomers, including enantiomers, diastereomers, and atropisomers. In addition, the compounds disclosed herein include enriched or resolved optical isomers at any or all asymmetric, chiral atoms. Such compositions thus include racemic mixtures of all stereoisomers, including enantiomers, diastereomers, and atropisomers. In addition, the compositions disclosed herein include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures can be separated into their individual, substantially optically pure isomers through well-known techniques such as, for example, the separation of diastereomeric salts formed with optically active adjuncts, e.g., acids or bases followed by conversion back to the optically active substances. The desired optical isomer can also be synthesized by means of stereospecific reactions, beginning with the appropriate stereoisomer of the desired starting material.

It is to be understood that for compounds disclosed herein when a bond is drawn in a non-stereochemical manner (e.g., flat) the atom to which the bond is attached includes all stereochemical possibilities. It is also to be understood that when a bond is drawn in a stereochemical manner (e.g., bold, bold-wedge, dashed or dashed-wedge) the atom to which the stereochemical bond is attached has the stereochemistry as shown unless otherwise noted. Accordingly, in one embodiment, a compound disclosed herein is greater than 50% a single enantiomer. In another embodiment, a compound disclosed herein is at least 80% a single enantiomer. In another embodiment, a compound disclosed herein is at least 90% a single enantiomer. In another embodiment, a compound disclosed herein is at least 98% a single enantiomer. In another embodiment, a compound disclosed herein is at least 99% a single enantiomer. In another embodiment, a compound disclosed herein is greater than 50% a single diastereomer. In another embodiment, a compound disclosed herein is at least 80% a single diastereomer. In another embodiment, a compound disclosed herein is at least 90% a single diastereomer. In another embodiment, a compound disclosed herein is at least 98% a single diastereomer. In another embodiment, a compound disclosed herein is at least 99% a single diastereomer.

Accordingly, in one embodiment, a composition disclosed herein is greater than 50% a single enantiomer. In another embodiment, a composition disclosed herein is at least 80% a single enantiomer. In another embodiment, a composition disclosed herein is at least 90% a single enantiomer. In another embodiment, a composition disclosed herein is at least 98% a single enantiomer. In another embodiment, a composition disclosed herein is at least 99% a single enantiomer. In another embodiment, a composition disclosed herein is greater than 50% a single diastereomer. In another embodiment, a composition disclosed herein is at least 80% a single diastereomer. In another embodiment, a composition disclosed herein is at least 90% a single diastereomer. In another embodiment, a composition disclosed herein is at least 98% a single diastereomer. In another embodiment, a composition disclosed herein is at least 99% a single diastereomer.

Tautomers

The compounds disclosed herein can also exist as tautomeric isomers in certain cases. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

Protecting Groups

"Protecting group" refers to a moiety of a compound that masks or alters the properties of a functional group or the properties of the compound as a whole. Chemical protecting groups and strategies for protection/deprotection are well known in the art. See e.g., *Protective Groups in Organic Chemistry*, Theodora W. Greene, John Wiley & Sons, Inc., New York, 1991. Protecting groups are often utilized to mask the reactivity of certain functional groups, to assist in the efficiency of desired chemical reactions, e.g., making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

Salts and Hydrates

Examples of pharmaceutically acceptable salts of the compounds disclosed herein include salts derived from an appropriate base, such as an alkali metal (for example, sodium), an alkaline earth metal (for example, magnesium), ammonium and $NX_4^+$ (wherein X is $C_1$-$C_4$ alkyl). Pharmaceutically acceptable salts of a nitrogen atom or an amino group include for example salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, hydrobromic, sulfuric, phosphoric and sulfamic acids. Pharmaceutically acceptable salts of a compound of a hydroxy group include the anion of said compound in combination with a suitable cation such as $Na^+$ and $NX_4^+$ (wherein each X is independently selected from H or a $C_1$-$C_4$ alkyl group).

A pharmaceutically acceptable salt can refer to a salt of a compound that is pharmaceutically acceptable and that possesses (or can be converted to a form that possesses) the desired pharmacological activity of the parent compound. Examples of pharmaceutically acceptable salts of the compounds disclosed herein include salts derived from an appropriate base, such as an alkali metal (for example, sodium), an alkaline earth metal (for example, magnesium), ammonium and $NX_4^+$ (wherein X is $C_1$-$C_4$ alkyl). Pharmaceutically acceptable salts of a nitrogen atom or an amino group include for example salts of organic carboxylic acids such as acetic, benzoic, camphorsulfonic, citric, glucoheptonic, gluconic, lactic, fumaric, tartaric, maleic, malonic, malic, mandelic, isethionic, lactobionic, succinic, 2-naphthalenesulfonic, oleic, palmitic, propionic, stearic, and trimethylacetic acids; organic sulfonic acids, such as methanesulfonic, ethanesulfonic, benzenesulfonic and p-toluenesulfonic acids; and inorganic acids, such as hydrochloric, hydrobromic, sulfuric, nitric, phosphoric and sulfamic acids. Pharmaceutically acceptable salts of a compound of a hydroxy group include the anion of said compound in combination with a suitable cation such as $Na^+$ and $NX_4^+$ (wherein X is independently selected from H or a $C_1$-$C_4$ alkyl group). Pharmaceutically acceptable salts also include salts formed when an acidic proton present in the parent compound is replaced by either a metal ion, e.g., an alkali metal ion, an alkaline earth ion, or an aluminum ion; or coordinates with an organic base such as diethanolamine, triethanolamine, N-methylglucamine and the like. Also included in this definition are ammonium and substituted or quaternized ammonium salts. Representative non-limiting lists of pharmaceutically acceptable salts can be found in S. M. Berge et al., J. Pharma Sci., 66(1), 1-19 (1977), and Remington: The Science and Practice of Pharmacy, R. Hendrickson, ed., 21st edition, Lippincott, Williams & Wilkins, Philadelphia, Pa., (2005), at p. 732, Table 38-5, both of which are hereby incorporated by reference herein.

For therapeutic use, salts of active ingredients of the compounds disclosed herein will typically be pharmaceutically acceptable, i.e., they will be salts derived from a physiologically acceptable acid or base. However, salts of acids or bases which are not pharmaceutically acceptable may also find use, for example, in the preparation or purification of a compound of formula I or another compound disclosed herein. All salts, whether or not derived from a physiologically acceptable acid or base, are within the scope of the present invention.

Metal salts typically are prepared by reacting the metal hydroxide with a compound disclosed herein. Examples of metal salts which are prepared in this way are salts containing $Li^+$, $Na^+$, and $K^+$. A less soluble metal salt can be precipitated from the solution of a more soluble salt by addition of the suitable metal compound.

In addition, salts may be formed from acid addition of certain organic and inorganic acids, e.g., HCl, HBr, $H_2SO_4$, $H_3PO_4$ or organic sulfonic acids, to basic centers, such as amines. Finally, it is to be understood that the compositions herein comprise compounds disclosed herein in their un-ionized, as well as zwitterionic form, and combinations with stoichiometric amounts of water as in hydrates.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

Isotopes

It is understood by one skilled in the art that this invention also includes any compound claimed that may be enriched at any or all atoms above naturally occurring isotopic ratios with one or more isotopes such as, but not limited to, deuterium ($^2H$ or D). As a non-limiting example, a —$CH_3$ group may be substituted with —$CD_3$.

Specific values listed below for radicals, substituents, and ranges in the embodiments of the invention are for illustration only; they do not exclude other defined values or other values within defined ranges for the radicals and substituents.

Compounds of Formula I.

A specific group of compounds of formula I are compounds of formula Ia.

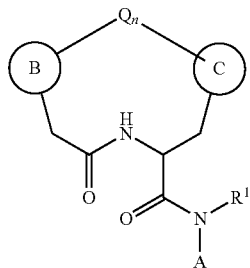

Ia or a salt thereof. In certain embodiments, a salt is a pharmaceutically acceptable salt.

Another specific group of compounds of formula I are compounds of formula Ib.

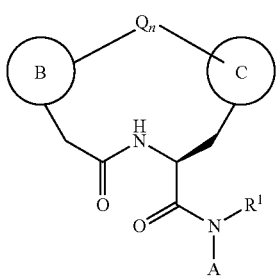

Ib or a salt thereof. In certain embodiments, a salt is a pharmaceutically acceptable salt.

Another specific group of compounds of formula I are compounds of formula Ic.

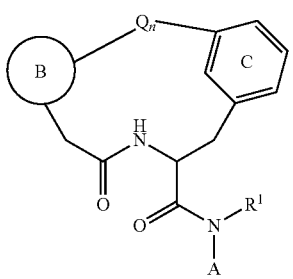

Ic wherein phenyl C is optionally substituted with one or more (e.g., 1, 2, 3, 4 or 5) $Z^3$ groups, or a salt thereof. In certain embodiments, a salt is a pharmaceutically acceptable salt.

Another specific group of compounds of formula I are compounds of formula Id.

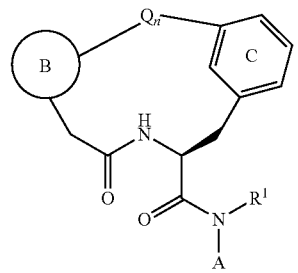

Id wherein phenyl C is optionally substituted with one or more (e.g., 1, 2, 3, 4 or 5) $Z^3$ groups, or a salt thereof. In certain embodiments, a salt is a pharmaceutically acceptable salt.

Another specific group of compounds of formula I are compounds of formula Ie.

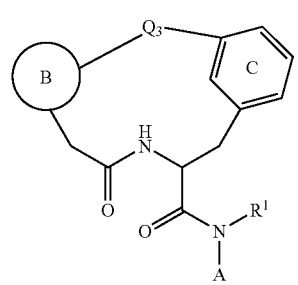

Ie wherein phenyl C is optionally substituted with one or more (e.g., 1, 2, 3, 4 or 5) $Z^3$ groups, or a salt thereof. In certain embodiments, a salt is a pharmaceutically acceptable salt.

Another specific group of compounds of formula I are compounds of formula If.

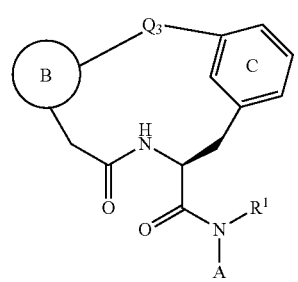

If wherein phenyl C is optionally substituted with one or more (e.g., 1, 2, 3, 4 or 5) $Z^3$ groups, or a salt thereof. In certain embodiments, a salt is a pharmaceutically acceptable salt.

Specific values listed below are values for compounds of formula I as well as the compounds of formula Ia, Ib, Ic, Id, Ie and If.

A specific group of compounds of formula I are compounds wherein each $R^{1a}$ is H or $(C_1-C_4)$alkyl, each $R^{2a}$ is H and each $R^{2b}$ is H.

A specific value for $R^{1a}$ is H or $(C_1-C_4)$alkyl.

A specific value for $R^{2a}$ is H.

A specific value for $R^{2b}$ is H.

A specific value for n is 2, 3 or 4.

Another specific value for n is 1, 2, 3 or 4.

A specific group of compounds of formula I are compounds wherein each Q is independently —CH$_2$—S— or —S(=O)$_2$—, or two adjacent Q groups taken together are —CH=CH—.

A specific group of compounds of formula I are compounds wherein each Q is independently —CH$_2$—S— or —S(=O)$_2$—.

A specific value for $Q_n$ is —CH=CHCH$_2$—, —(CH$_2$)$_2$—, —(CH$_2$)$_3$—, —(CH$_2$)$_4$—, —CH$_2$CH=CH—, —CH$_2$SCH$_2$—, —CH$_2$S(=O)$_2$CH$_2$—, —CH=CH—, —CH$_2$S(CH$_2$)$_2$—, —CH$_2$S(=O)$_2$(CH$_2$)$_2$—, —CH$_2$S—, —CH$_2$S(CH$_2$)$_2$—, —SCH$_2$— or —S(=O)$_2$CH$_2$—.

A specific group of compounds of formula I are compounds wherein each Q is independently selected from —C(R$^{2a}$)$_2$—, —O—, —NR$^1$—, —S—, —C(=O)—, —S(=O)— and —S(=O)$_2$—, or two adjacent Q groups taken together can be —CR$^{2b}$=CR$^{2b}$—; provided no two groups selected from —O—, —NR$^1$— and —S— are adjacent to each other.

In one embodiment no two Q groups selected from —O—, —NR$^1$— and —S— can be adjacent to each other.

A specific value for X is CH.

A specific value for C is phenyl, 5-membered heteroaryl or 6-membered heteroaryl, wherein any phenyl, 5-membered heteroaryl or 6-membered heteroaryl of C is optionally substituted with one or more (e.g., 1, 2, 3, 4 or 5) $Z^3$ groups.

A specific value for C is phenyl, 5-membered heteroaryl or 6-membered heteroaryl, wherein any phenyl, 5-membered heteroaryl or 6-membered heteroaryl of C is optionally substituted with one or more (e.g., 1, 2, 3, 4 or 5) $Z^3$ groups, and wherein Q and Y are connected to adjacent ring atoms of C.

A specific value for C is phenyl, 5-membered heteroaryl or 6-membered heteroaryl, wherein any phenyl, 5-membered heteroaryl or 6-membered heteroaryl of C is optionally substituted with one or more (e.g., 1, 2, 3, 4 or 5) $Z^3$ groups, and wherein Q and Y are connected to the first and third atom of three consecutive ring atoms of C.

A specific value for C is phenyl, wherein any phenyl of C is optionally substituted with one or more (e.g., 1, 2, 3, 4 or 5) $Z^3$ groups.

A specific value for C is phenyl, wherein any phenyl of C is optionally substituted with one or more (e.g., 1, 2, 3, 4 or 5) $Z^3$ groups, and wherein Q and Y are connected to adjacent ring atoms of C.

A specific value for C is phenyl, wherein any phenyl of C is optionally substituted with one or more (e.g., 1, 2, 3, 4 or 5) $Z^3$ groups, and wherein Q and Y are connected to the first and third atom of three consecutive ring atoms of C.

A specific value for $Z^3$ is halogen or (C$_1$-C$_4$)alkyl.

A specific value for $Z^3$ is halogen.

A specific value for $Z^3$ is fluoro.

A specific value for $R^1$ is (C$_1$-C$_4$)alkyl.

A specific value for $R^1$ is methyl.

A specific value for A is aryl or aryl(C$_1$-C$_6$)alkyl-, wherein any aryl or aryl(C$_1$-C$_6$)alkyl- of A is optionally substituted with one or more (e.g., 1, 2, 3, 4 or 5) $Z^1$ groups.

A specific value for A is aryl or aryl(C$_1$-C$_6$)alkyl-, wherein aryl or the aryl of aryl(C$_1$-C$_6$)alkyl- has 6-12 carbon atoms in the aryl ring, and wherein any aryl or aryl(C$_1$-C$_6$)alkyl- of A is optionally substituted with one or more (e.g., 1, 2, 3, 4 or 5) $Z^1$ groups.

A specific value for A is phenyl or benzyl, wherein any phenyl or benzyl of A is optionally substituted with one or more (e.g., 1, 2, 3, 4 or 5) $Z^1$ groups.

A specific value for A is aryl, wherein aryl is optionally substituted with one or more (e.g., 1, 2, 3, 4 or 5) $Z^1$ groups.

A specific value for A is aryl, wherein aryl has 6-12 carbon atoms in the aryl ring, wherein aryl is optionally substituted with one or more (e.g., 1, 2, 3, 4 or 5) $Z^1$ groups.

A specific value for A is phenyl optionally substituted with one or more (e.g., 1, 2, 3, 4 or 5) $Z^1$ groups.

A specific value for each $Z^1$ is independently selected from halogen and —O(C$_1$-C$_4$)alkyl.

A specific value for each $Z^1$ is independently selected from chloro and —OMe.

A specific value for each $Z^1$ is independently selected from chloro and —OMe.

A specific value for A is 4-methoxyphenyl, 4-chlorophenyl or benzyl.

A specific value for $Z^1$ is halogen or —OR$_{n1}$.

A specific value for $R_{n1}$ is (C$_1$-C$_4$)alkyl.

A specific value for B is heteroaryl, wherein heteroaryl is optionally substituted with one or more (e.g., 1, 2, 3, 4 or 5) $Z^2$ groups.

A specific value for B is heteroaryl, wherein heteroaryl has 2-10 carbon atoms and 1-5 heteroatoms in the heteroaryl ring system, and wherein heteroaryl is optionally substituted with one or more (e.g., 1, 2, 3, 4 or 5) $Z^2$ groups.

A specific value for B is bicyclic-heteroaryl, wherein bicyclic-heteroaryl is optionally substituted with one or more (e.g., 1, 2, 3, 4 or 5) $Z^2$ groups.

A specific value for B is bicyclic-heteroaryl, wherein bicyclic-heteroaryl has 4-10 carbon atoms and 1-5 heteroatoms in the bicyclic-heteroaryl ring system wherein bicyclic-heteroaryl is optionally substituted with one or more (e.g., 1, 2, 3, 4 or 5) $Z^2$ groups.

A specific value for B is indolyl, 1H-pyrrolo[3,2-b]pyridinyl or pyrazolyl, wherein any indolyl, 1H-pyrrolo[3,2-b]pyridinyl or pyrazolyl of B is optionally substituted with one or more (e.g., 1, 2, 3, 4 or 5) $Z^2$ groups.

A specific value for each $Z^2$ is independently selected from (C$_1$-C$_4$)alkyl, halogen and —OR$_{n3}$, wherein any (C$_1$-C$_4$)alkyl of $Z^2$ is optionally substituted with one or more (e.g., 1, 2, 3, 4 or 5) $Z^{2a}$ groups.

A specific value for each $R_{n3}$ is H or (C$_1$-C$_4$)alkyl, wherein any (C$_1$-C$_4$)alkyl of $R_{n3}$ is optionally substituted with one or more (e.g., 1, 2, 3, 4 or 5) $Z^{2a}$ groups.

A specific value for each $R_{n3}$ is H or methyl.

A specific value for each $Z^2$ is independently selected from (C$_1$-C$_4$)alkyl, halogen, —OH and —O(C$_1$-C$_4$)alkyl, wherein (C$_1$-C$_4$)alkyl is optionally substituted with one or more (e.g., 1, 2, 3, 4 or 5) halogen.

A specific value for each $Z^2$ is independently selected from trifluormethyl, fluoro, hydroxy and methoxy.

A specific value for B is selected from:

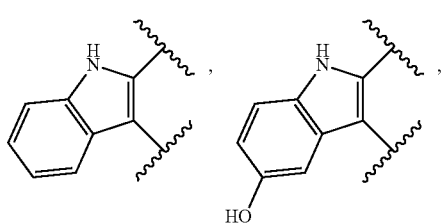

-continued

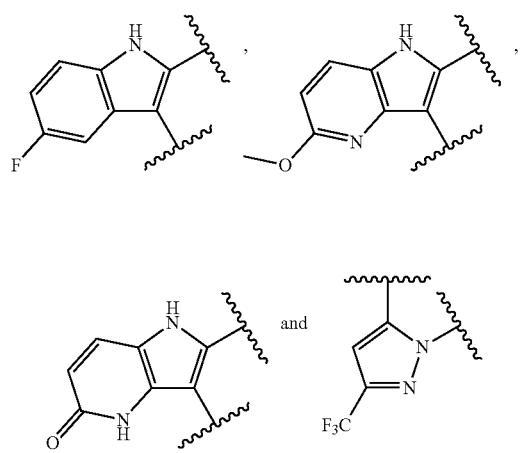

wherein the wavy lines denote points of attachment of B to W and Q of the compound of formula I.

A specific value for A is a value for A as depicted in any or all of the examples as described herein below.

A specific value for B is a value for B as depicted in any or all of the examples as described herein below.

A specific value for C is a value for C as depicted in any or all of the examples as described herein below.

A specific value for Q is a value for Q as depicted in any or all of the examples as described herein below.

A specific value for X is a value for X as depicted in any or all of the examples as described herein below.

A specific value for $R^1$ is a value for $R^1$ as depicted in any or all of the examples as described herein below.

One embodiment provides a compound of formula I as described in any or all of the examples as described herein below.

One embodiment provides an isomer (e.g. stereoisomer such as an enantiomer or diastereomer) of a compound of formula I as described in any or all of the examples as described herein below.

One embodiment provides a racemic mixture of a compound of formula I as described in any or all of the examples as described herein below.

In one embodiment a heteroaryl is a ring system having 1, 2, 3 or 4 rings.

In one embodiment a heteroaryl is a ring system having 1, 2 or 3 rings.

In one embodiment a heteroaryl is a ring system having 1 or 2 rings.

In one embodiment a heterocycle is a ring system having 2, 3 or 4 rings.

In one embodiment a heterocycle is a ring system having 1, 2, 3 or 4 rings.

In one embodiment a heterocycle is a ring system having 1, 2 or 3 rings.

In one embodiment a heterocycle is a ring system having 1 or 2 rings.

In one embodiment a heterocycle is a ring system having 2, 3 or 4 rings.

In one embodiment the compound of formula I is selected from:

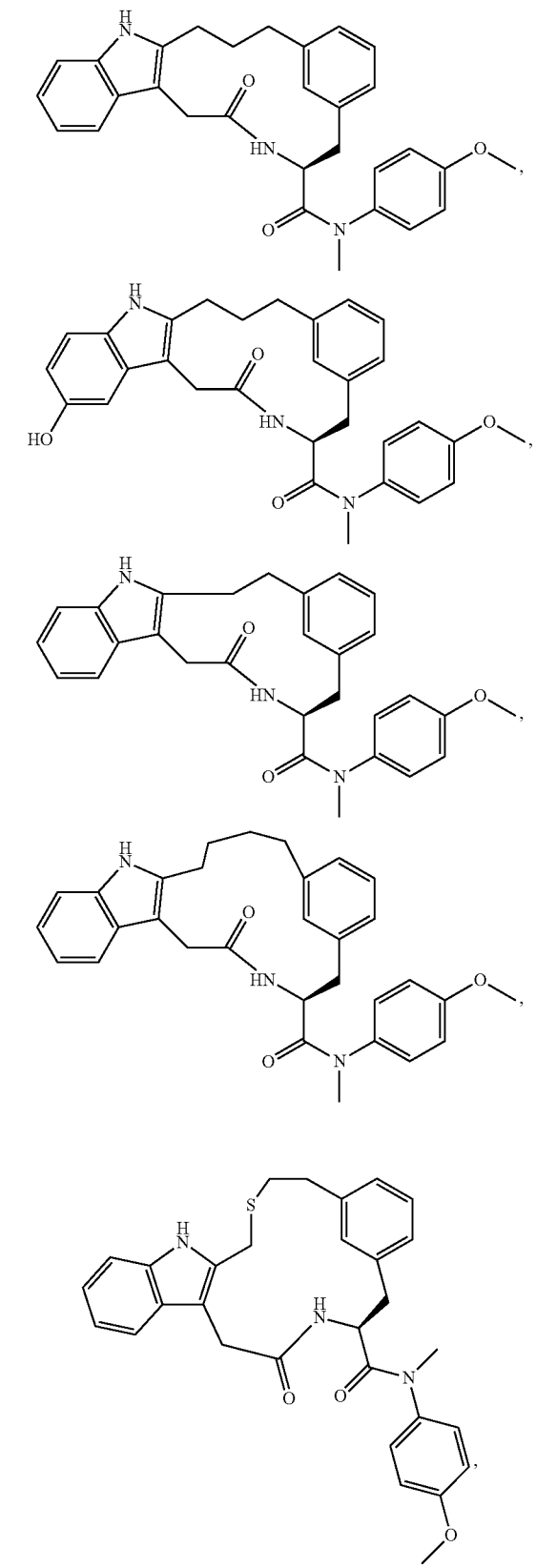

-continued
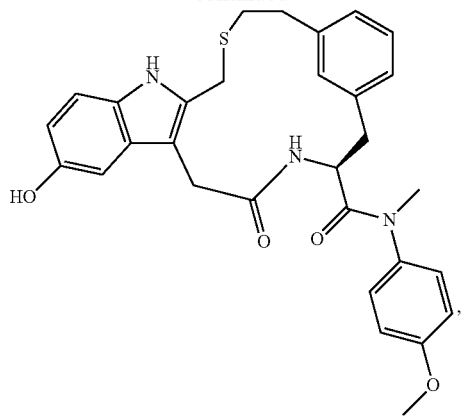
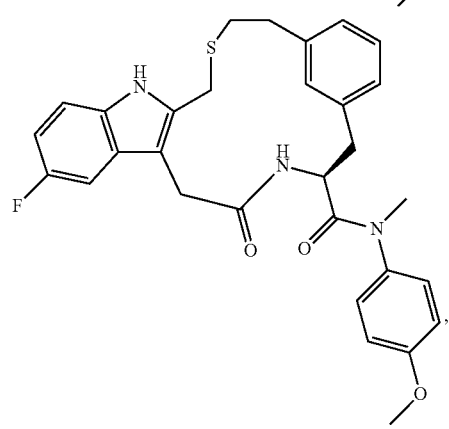
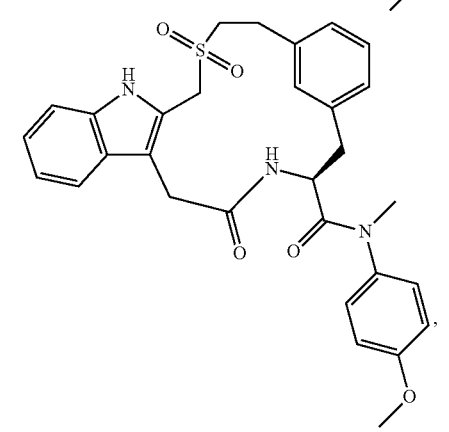
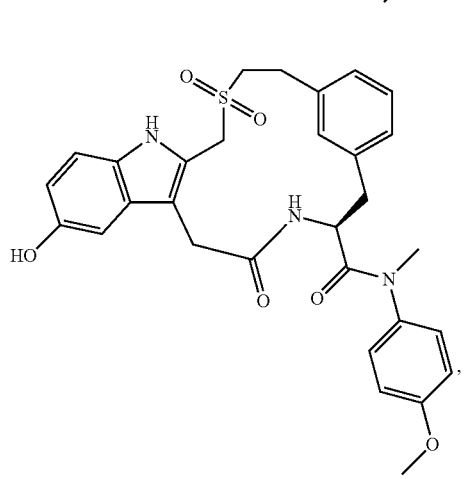
-continued
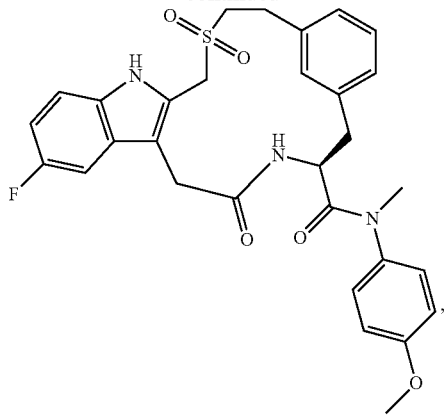
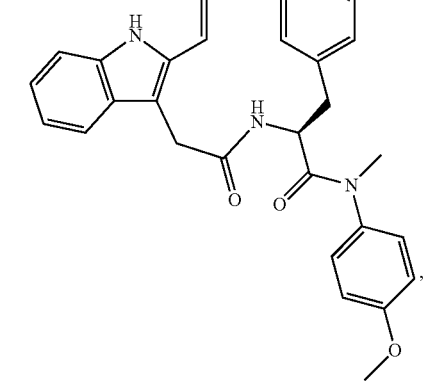
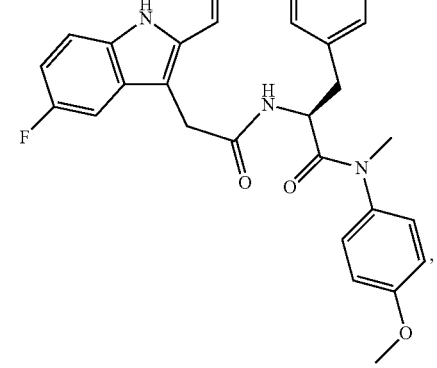
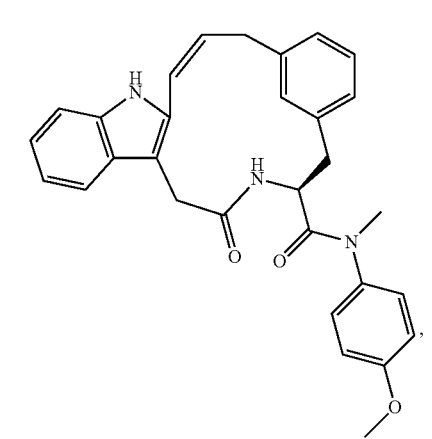

21
-continued
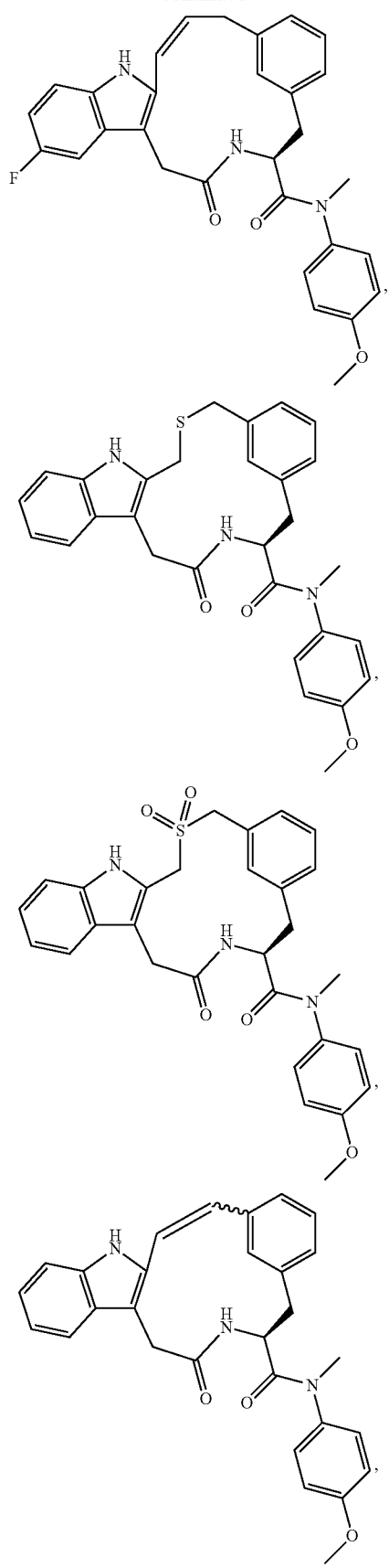
22
-continued
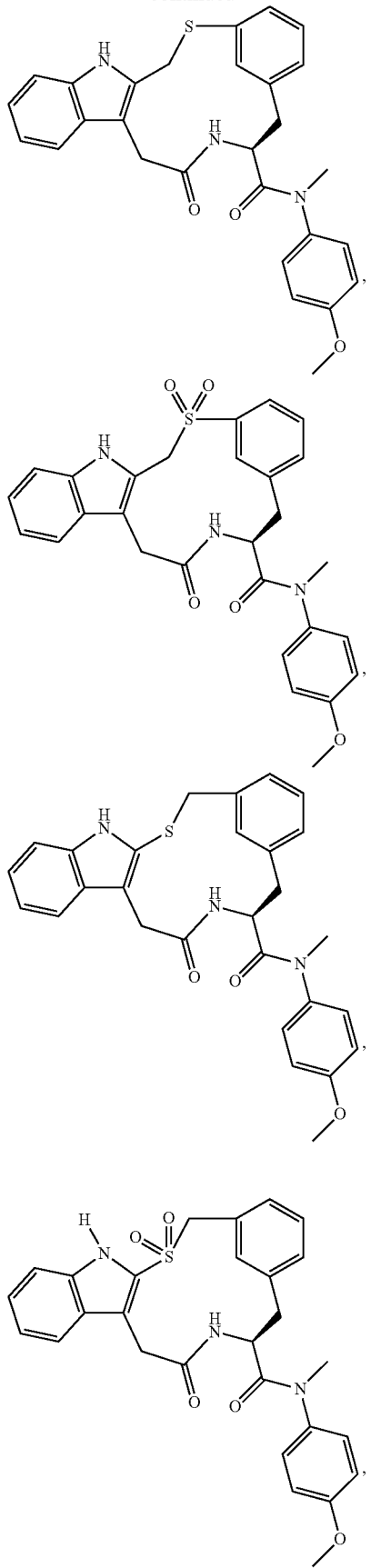

23
-continued
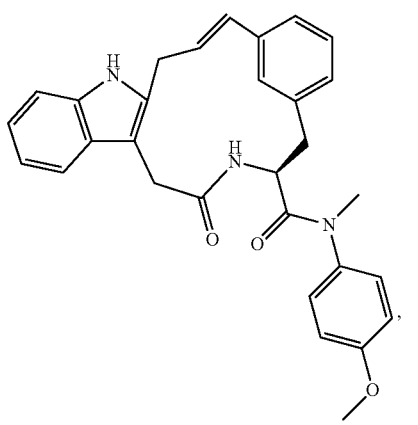
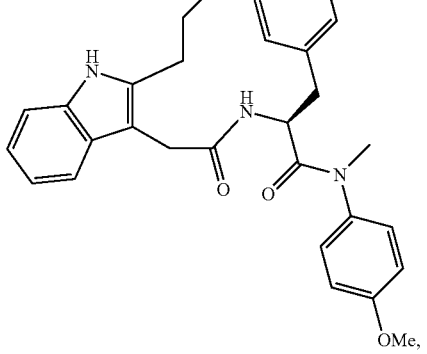
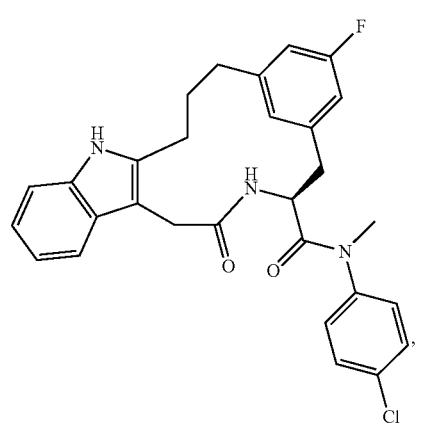
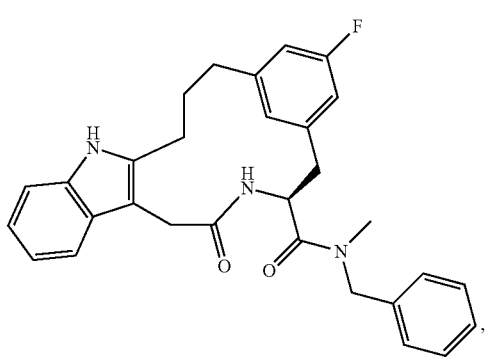
24
-continued
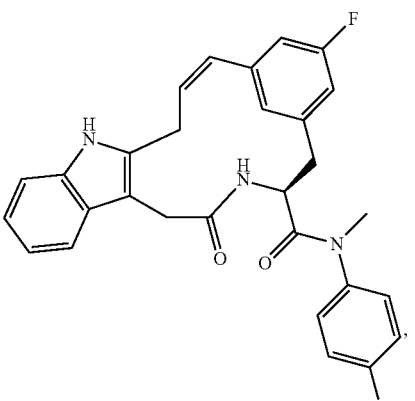
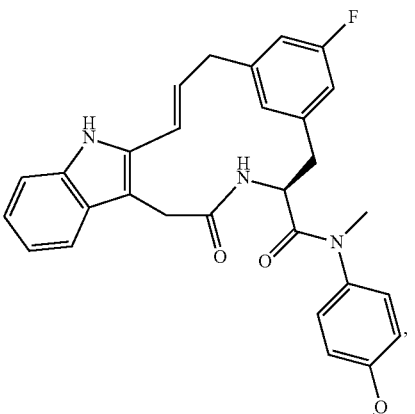
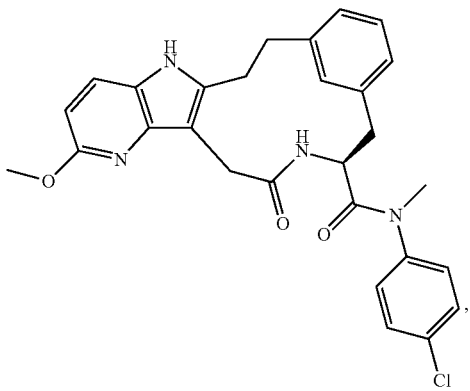
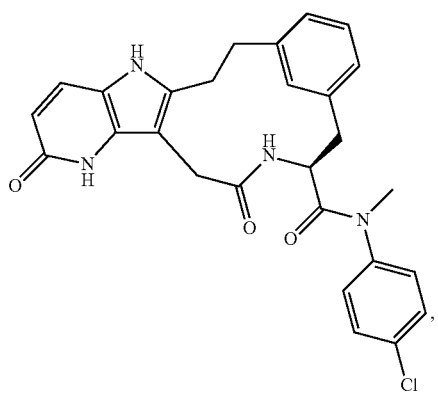

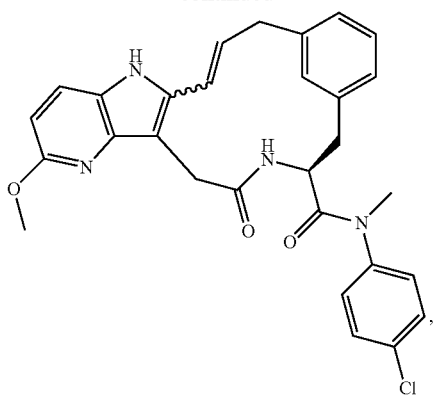

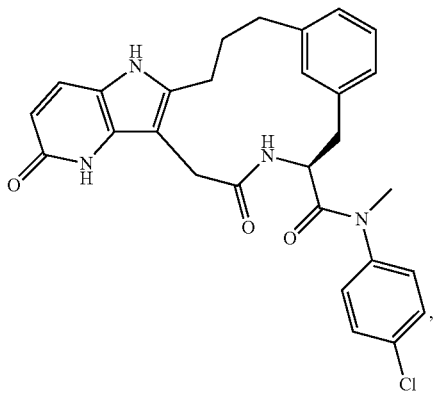

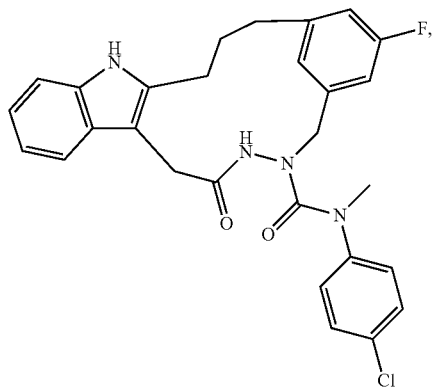

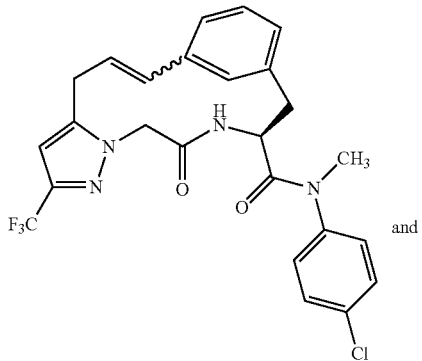

and

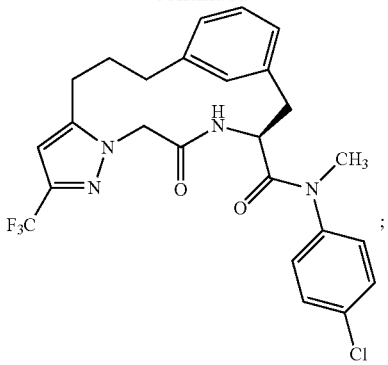 [SMILES: CN(C(=O)[C@@H]1Cc2cccc(c2)CCCc2cc(C(F)(F)F)nn2CC(=O)N1)c1ccc(Cl)cc1]

and salts thereof.

Combination Therapy

In one embodiment, the invention provides a method for treating an HIV infection, comprising administering to a patient in need thereof a therapeutically effective amount of a compound disclosed herein, or a pharmaceutically acceptable salt, thereof, in combination with a therapeutically effective amount of one or more additional therapeutic agents which are suitable for treating an HIV infection.

In one embodiment, a method for treating or preventing an HIV infection in a human having or at risk of having the infection is provided, comprising administering to the human a therapeutically effective amount of a compound disclosed herein, or a pharmaceutically acceptable salt thereof, in combination with a therapeutically effective amount of one or more additional therapeutic agents.

In one embodiment, the invention provides pharmaceutical compositions comprising a compound disclosed herein, or a pharmaceutically acceptable salt thereof, in combination with at least one additional therapeutic agent, and a pharmaceutically acceptable carrier. For example, the therapeutic agent used in combination with the compound disclosed herein can be any anti-HIV agent.

In one embodiment, combination pharmaceutical agents comprising a compound disclosed herein, or a pharmaceutically acceptable salt thereof, in combination with one or more additional therapeutic agents are provided.

One embodiment provides pharmaceutical compositions comprising a compound disclosed herein, or a pharmaceutically acceptable salt thereof, in combination with at least one additional therapeutic agent, and a pharmaceutically acceptable carrier. In one embodiment, the additional therapeutic agent may be an anti-HIV agent. For example, in some embodiments, the additional therapeutic agent is selected from the group consisting of HIV protease inhibiting compounds (HIV protease inhibitors), HIV non-nucleoside inhibitors of reverse transcriptase, HIV nucleoside inhibitors of reverse transcriptase, HIV nucleotide inhibitors of reverse transcriptase, HIV integrase inhibitors, HIV non-catalytic site (or allosteric) integrase inhibitors, entry inhibitors (e.g., CCR5 inhibitors, gp41 inhibitors (i.e., fusion inhibitors) and CD4 attachment inhibitors), CXCR4 inhibitors, gp120 inhibitors, G6PD and NADH-oxidase inhibitors, capsid polymerization inhibitors or capsid disrupting compounds such as those disclosed in US 2013/0165489 (University of Pennsylvania), and WO 2013/006792 (Pharma Resources), pharmacokinetic enhancers, and other drug for treating HIV, and combinations thereof.

In further embodiments, the additional therapeutic agent is selected from one or more of:

(1) HIV protease inhibitors selected from the group consisting of amprenavir, atazanavir, fosamprenavir, indinavir, lopinavir, ritonavir, nelfinavir, saquinavir, tipranavir, brecanavir, darunavir, TMC-126, TMC-114, mozenavir (DMP-450), JE-2147 (AG1776), L-756423, R00334649, KNI-272, DPC-681, DPC-684, GW640385X, DG17, PPL-100, DG35, and AG 1859;

(2) HIV non-nucleoside or non-nucleotide inhibitors of reverse transcriptase selected from the group consisting of capravirine, emivirine, delaviridine, efavirenz, nevirapine, (+) calanolide A, etravirine, GW5634, DPC-083, DPC-961, DPC-963, MW-150, TMC-120, rilpivirene, BILR 355 BS, VRX 840773, lersivirine (UK-453061), RDEA806, KM023 and MK-1439;

(3) HIV nucleoside inhibitors of reverse transcriptase selected from the group consisting of zidovudine, emtricitabine, didanosine, stavudine, zalcitabine, lamivudine, abacavir, amdoxovir, elvucitabine, alovudine, MIV-210, ±-FTC, D-d4FC, emtricitabine, phosphazide, fozivudine tidoxil, apricitibine (AVX754), amdoxovir, KP-1461, GS-9131 (Gilead Sciences) and fosalvudine tidoxil (formerly HDP 99.0003);

(4) HIV nucleotide inhibitors of reverse transcriptase selected from the group consisting of tenofovir, tenofovir disoproxil fumarate, tenofovir alafenamide fumarate (Gilead Sciences), tenofovir alafenamide (Gilead Sciences), GS-7340 (Gilead Sciences), GS-9148 (Gilead Sciences), adefovir, adefovir dipivoxil, CMX-001 (Chimerix) or CMX-157 (Chimerix);

(5) HIV integrase inhibitors selected from the group consisting of curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, AR-177, L-870812, and L-870810, raltegravir, BMS-538158, GSK364735C, BMS-707035, MK-2048, BA 011, elvitegravir, dolutegravir and GSK-744;

(6) HIV non-catalytic site, or allosteric, integrase inhibitors (NCINI) including, but not limited to, BI-224436, CX0516, CX05045, CX14442, compounds disclosed in WO 2009/062285 (Boehringer Ingelheim), WO 2010/130034 (Boehringer Ingelheim), WO 2013/159064 (Gilead Sciences), WO 2012/145728 (Gilead Sciences), WO 2012/003497 (Gilead Sciences), WO 2012/003498 (Gilead Sciences) each of which is incorporated by reference in its entirety herein;

(7) gp41 inhibitors selected from the group consisting of enfuvirtide, sifuvirtide, albuvirtide, FB006M, and TRI-1144;

(8) the CXCR4 inhibitor AMD-070;

(9) the entry inhibitor SP01A;

(10) the gp120 inhibitor BMS-488043;

(11) the G6PD and NADH-oxidase inhibitor immunitin;

(12) CCR5 inhibitors selected from the group consisting of aplaviroc, vicriviroc, maraviroc, cenicriviroc, PRO-140, INCB15050, PF-232798 (Pfizer), and CCR5 mAb004;

(13) CD4 attachment inhibitors selected from the group consisting of ibalizumab (TMB-355) and BMS-068 (BMS-663068);

(14) pharmacokinetic enhancers selected from the group consisting of cobicistat and SPI-452; and

(15) other drugs for treating HIV selected from the group consisting of BAS-100, SPI-452, REP 9, SP-01A, TNX-355, DES6, ODN-93, ODN-112, VGV-1, PA-457 (bevirimat), HRG214, VGX-410, KD-247, AMZ 0026, CYT 99007A-221 HIV, DEBIO-025, BAY 50-4798, MDX010 (ipilimumab), PBS 119, ALG 889, and PA-1050040 (PA-040).

In certain embodiments, a compound disclosed herein, or a pharmaceutically acceptable salt thereof, is combined with two, three, four or more additional therapeutic agents. In certain embodiments, a compound disclosed herein, or a pharmaceutically acceptable salt thereof, is combined with two additional therapeutic agents. In other embodiments, a compound disclosed herein, or a pharmaceutically acceptable salt thereof, is combined with three additional therapeutic agents. In further embodiments, a compound disclosed herein, or a pharmaceutically acceptable salt thereof, is combined with four additional therapeutic agents. The two, three four or more additional therapeutic agents can be different therapeutic agents selected from the same class of therapeutic agents, or they can be selected from different classes of therapeutic agents. In a specific embodiment, a compound disclosed herein, or a pharmaceutically acceptable salt thereof, is combined with an HIV nucleotide inhibitor of reverse transcriptase and an HIV non-nucleoside inhibitor of reverse transcriptase. In another specific embodiment, a compound disclosed herein, or a pharmaceutically acceptable salt thereof, is combined with an HIV nucleotide inhibitor of reverse transcriptase, and an HIV protease inhibiting compound. In a further embodiment, a compound disclosed herein, or a pharmaceutically acceptable salt thereof, is combined with an HIV nucleotide inhibitor of reverse transcriptase, an HIV non-nucleoside inhibitor of reverse transcriptase, and an HIV protease inhibiting compound. In an additional embodiment, a compound disclosed herein, or a pharmaceutically acceptable salt thereof, is combined with an HIV nucleotide inhibitor of reverse transcriptase, an HIV non-nucleoside inhibitor of reverse transcriptase, and a pharmacokinetic enhancer.

In some embodiments, one or more of the compounds disclosed herein are combined with one or more other active therapeutic agents in a unitary dosage form for simultaneous or sequential administration to a patient. The combination therapy may be administered as a simultaneous or sequential regimen. When administered sequentially, the combination may be administered in two or more administrations.

In some embodiments, one or more of the compounds disclosed herein are co-administered with one or more other active therapeutic agents. Co-administration of a compound disclosed herein with one or more other active therapeutic agents generally refers to simultaneous or sequential administration of a compound disclosed herein and one or more other active therapeutic agents, such that therapeutically effective amounts of disclosed herein and one or more other active therapeutic agents are both present in the body of the patient.

In yet another embodiment, the present application provides a method for treating an HIV infection comprising administering to a patient in need thereof a therapeutically effective amount of a compound disclosed herein, or a pharmaceutically acceptable salt thereof, in combination with a therapeutically effective amount of one or more additional therapeutic agents such as those disclosed above.

Pharmaceutical Formulations

The compounds disclosed herein are formulated with conventional carriers (e.g., inactive ingredient or excipient material) which will be selected in accord with ordinary practice. Tablets will contain excipients including glidants, fillers, binders and the like. Aqueous formulations are prepared in sterile form, and when intended for delivery by other than oral administration generally will be isotonic. All formulations will optionally contain excipients such as those set forth in the *Handbook of Pharmaceutical Excipients* (1986). Excipients include ascorbic acid and other antioxidants, chelating agents such as EDTA, carbohydrates such as dextrin, hydroxyalkylcellulose, hydroxyalkylmethylcellulose, stearic acid and the like. One embodiment provides the formulation as a solid dosage form including a solid oral dosage form. The pH of the formulations ranges from about 3 to about 11, but is ordinarily about 7 to 10.

While it is possible for the active ingredients to be administered alone it may be preferable to present them as pharmaceutical formulations (compositions). The formulations, both for veterinary and for human use, of the invention comprise at least one active ingredient, as above defined, together with one or more acceptable carriers and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with inactive ingredients (e.g., a carrier, pharmaceutical excipients, etc.) which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units including but not limited to capsules, cachets or tablets each containing a predetermined amount of the active ingredient.

Pharmaceutical formulations according to the present invention comprise one or more compounds disclosed herein together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

The amount of active ingredient that is combined with the inactive ingredients to produce a dosage form will vary depending upon the host treated and the particular mode of administration. For example, in some embodiments, a dosage form for oral administration to humans contains approximately 1 to 1000 mg of active material formulated with an appropriate and convenient amount of carrier material (e.g., inactive ingredient or excipient material). In certain embodiments, the carrier material varies from about 5 to about 95% of the total compositions (weight:weight).

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Effective dose of active ingredient depends at least on the nature of the condition being treated, toxicity, whether the compound is being used prophylactically (lower doses), the method of delivery, and the pharmaceutical formulation, and will be determined by the clinician using conventional dose escalation studies.

Routes of Administration

One or more compounds disclosed herein (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds disclosed herein is that they are orally bioavailable and can be dosed orally.

The antiviral properties of a compound of the invention may be determined using Test A described below.

Test A: Antiviral Assay in MT4 Cells

For the antiviral assay, 40 µL of 1× test concentration of 3-fold serially diluted compound in culture medium with 10% FBS was added to each well of a 384-well plate (10 concentrations) in quadruplicate. MT-4 cells were next mixed with HIV-IIIb at an m.o.i of 0.003 for 1 hour, after which time 35 µL of virus/cell mixture (2000 cells) was immediately added to each well containing 40 µL of diluted compound. The plates were then incubated at 37° C. for 5 days. After 5 days of incubation, 25 µl of 2× concentrated CellTiter-Glo™ Reagent (catalog #G7571, Promega Biosciences, Inc., Madison, Wis.) was added to each well containing MT-4 cells. Cell lysis was carried out by incubating at room temperature for 10 min and then chemiluminescence was read. EC50 values were defined as the compound concentration that caused a 50% decrease in luminescence signal, a measure of HIV-1 replication.

Test B: Cytotoxicity Assay

Compound cytotoxicity and the corresponding CC50 values were determined using the same protocol as described in the antiviral assay (Test A) except that uninfected cells were used.

Compounds of disclosed herein demonstrate antiviral activity (Test A) as depicted in the table below. Accordingly, the compounds disclosed herein may be useful for treating an HIV virus infection, treating AIDS or for delaying the onset of AIDS or ARC symptoms. The table shows the percent inhibition of virus-induced cell killing in the presence of 2 uM of the test compound and the corresponding values for compound cytotoxicity (CC50).

| Example | % Inh @ 2 uM | MT4-CC50 [uM] |
|---------|--------------|---------------|
| 1 | 102.9 | >50.3 |
| 2 | 102.4 | >46.4 |
| 3 | 99.2 | >53.0 |
| 4 | 79.6 | >48.7 |
| 5 | 33.4 | 49.5 |
| 6 | 94.3 | 49.2 |
| 7 | 26.3 | >53.0 |
| 8 | 0.6 | >53.0 |
| 9 | 0.7 | >53.0 |
| 10 | 1.8 | >53.0 |
| 11 | 101.9 | 23.9 |
| 12 | 85.5 | 31.8 |
| 13 | 99.0 | >53.0 |
| 14 | 95.6 | 44.3 |
| 15 | 95.8 | >51.4 |
| 16 | 67.8 | >53.0 |
| 17 | 4.7 | >53.0 |
| 18 | 47.3 | >53.0 |
| 19 | 80.3 | >53.0 |
| 20 | 97.7 | 45.2 |
| 21 | 11.8 | >53.0 |
| 22 | 64.5 | >52.6 |
| 23K | 94.0 | >50.3 |
| 24 | 100.2 | 47.1 |
| 25 | 84.9 | 52.3 |
| 26 | 79.9 | 34.8 |
| 27 | 92.5 | 18.9 |
| 28 | 63.9 | 18.3 |
| 29 | 87.6 | >53.0 |
| 30 | 0.0 | 24.4 |
| 31 | 2.4 | 21.7 |
| 32 | 72.3 | 22.5 |

In one embodiment, the compounds demonstrate >10% inhibition at 2 μM. In one embodiment, the compounds demonstrate >30% inhibition at 2 μM. In one embodiment, the compounds demonstrate >50% inhibition at 2 μM. In one embodiment, the compounds demonstrate >70% inhibition at 2 μM. It is to be understood that the compounds disclosed herein can be grouped according to their % inhibition as described above.

The specific pharmacological responses observed may vary according to and depending on the particular active compound selected or whether there are present pharmaceutical carriers, as well as the type of formulation and mode of administration employed, and such expected variations or differences in the results are contemplated in accordance with practice of the present invention.

The Examples provided herein describe the synthesis of compounds disclosed herein as well as intermediates used to prepare the compounds. It is to be understood that individual steps described herein may be combined. It is also to be understood that separate batches of a compound may be combined and then carried forth in the next synthetic step.

Examples 1-4

Preparation of Compounds 1-4

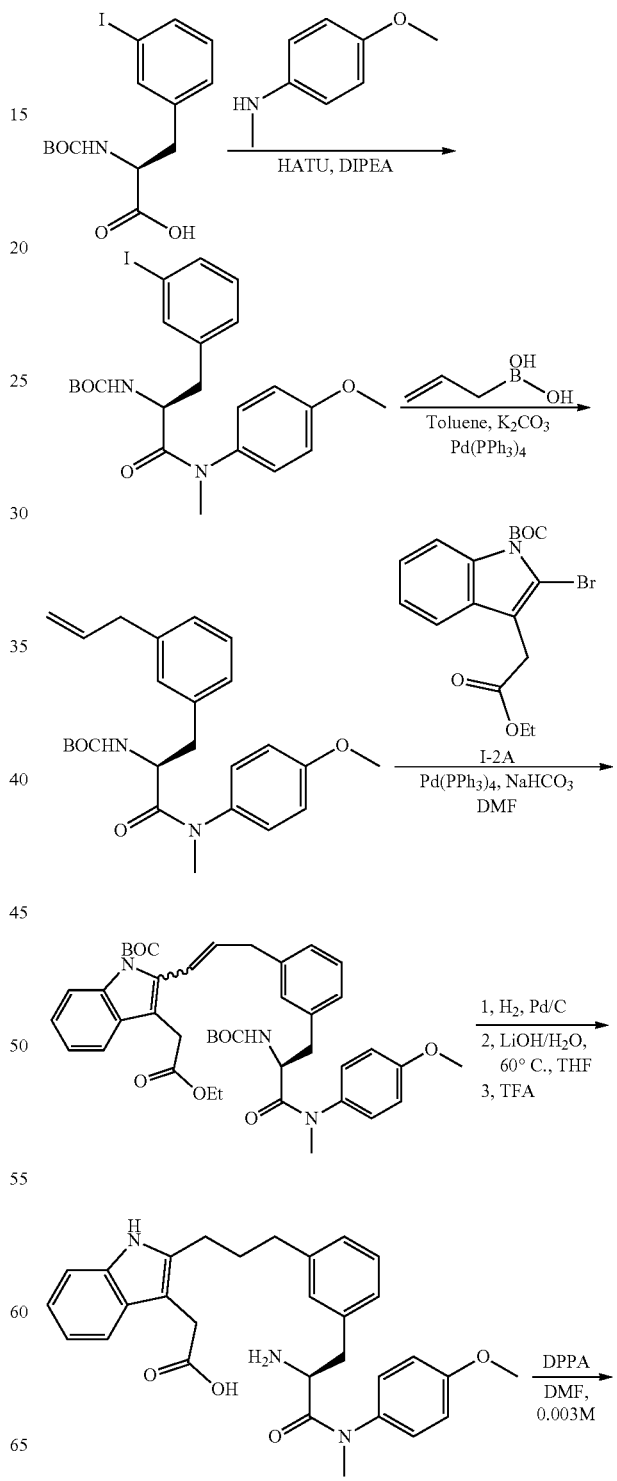

-continued

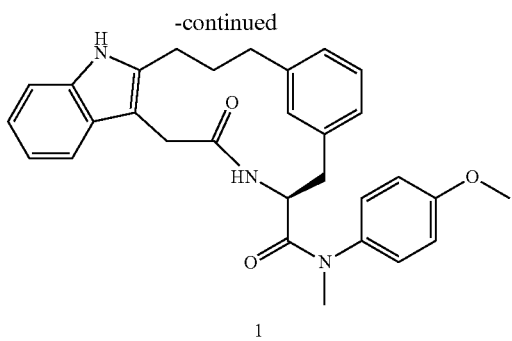

1

Synthesis of (5)-tert-butyl 3-(3-iodophenyl)-1-((4-methoxyphenyl)(methyl)amino)-1-oxopropan-2-ylcarbamate (S)-2-(tert-Butoxycarbonylamino)-3-(3-iodophenyl)propanoic acid (3.8 g, 9.65 mmol), 0-(7-azabenzotriazol-1-yl)-N,N,N',N'-tetramethyluronium hexafluorophosphate (HATU, 4.4 g, 11.6 mmol) and DIPEA (2.5 ml, 14.5 mmol) were dissolved in DMF (10 ml) and treated with 4-methoxy-N-methylaniline (1.59 g, 11.6 mmol). The mixture was stirred vigorously overnight at room temperature. The mixture was diluted with EtOAc (100 ml) and washed with brine (2×50 ml). The organic layer was dried over Na$_2$SO$_4$, filtered and concentrated. The oily crude product was introduced to a silica gel loading column and purified by column chromatography (15-38% EtOAc/hexanes) to provide the desired product (4.63 g, 9.07 mmol), 94%. MS (m/z) 511 [M+H]$^+$.

Synthesis of (5)-tert-butyl 3-(3-allylphenyl)-1-((4-methoxyphenyl)(methyl)amino)-1-oxopropan-2-ylcarbamate A suspension of (5)-tert-butyl 3-(3-iodophenyl)-1-(4-methoxyphenyl)(methyl)amino)-1-oxopropan-2-ylcarbamate (2.65 g, 5.2 mmol), 2-allyl-4,4,5,5-tetramethyl-1,3,2-dioxaborolane (1.13 g, 6.75 mmol), potassium carbonate (26 ml, 0.4 M) and tetrakis(triphenylphosphine)palladium(0) (0.6 g, 0.52 mmol) in 78 ml of toluene, was heated at reflux for 6 hours, cooled and filtered through celite. The filtrate was concentrated and the crude product was introduced to a silica gel loading column and purified by column chromatography (20-40% EtOAc/hexanes) to provide the desired product (1.75 g, 4.1 mmol), 79%. MS (m/z) 425 [M+H]$^+$.

Synthesis of (5)-tert-butyl 2-(3-(3-(2-(tert-butoxycarbonylamino)-3-((4-methoxyphenyl)(methyl)amino)-3-oxopropyl)phenyl)prop-1-enyl)-3-(2-ethoxy-2-oxoethyl)-1H-indole-1-carboxylate A suspension of (5)-tert-butyl 3-(3-allylphenyl)-1-((4-methoxyphenyl)(methyl)amino)-1-oxopropan-2-ylcarbamate (220 mg, 0.52 mmol), tert-butyl 2-bromo-3-(2-ethoxy-2-oxoethyl)-1H-indole-1-carboxylate (297 mg, 0.78 mmol), sodium bicarbonate (435 mg, 5.2 mmol) and tetrakis(triphenylphosphine)palladium(0) (60 mg, 0.05 mmol) in 4 ml of DMF was heated to 125° C. overnight. The reaction was cooled to room temperature and then filtered through celite. The filtrate was concentrated and the crude product was introduced to a silica gel loading column and purified by column chromatography (30-60% EtOAc/Hexans) to provide the desired product (178 mg, 0.25 mmol), 47%. MS (m/z) 726 [M+H]$^+$.

Synthesis of (S)-2-(2-(3-(3-(2-amino-3-((4-methoxyphenyl)(methyl)amino)-3-oxopropyl)phenyl)propyl)-1H-indol-3-yl)acetic acid A suspension of (5)-tert-butyl 2-(3-(3-(2-(tert-butoxycarbonylamino)-3-((4-methoxyphenyl)(methyl)amino)-3-oxopropyl)phenyl)prop-1-enyl)-3-(2-ethoxy-2-oxoethyl)-1H-indole-1-carboxylate (178 mg, 0.24 mmol) and palladium on carbon (134 mg, 10%) in 2.5 ml of ethanol and 2.5 ml of EtOAc, was degassed with nitrogen. The reaction was stirred at room temperature for 3 hours under an atmosphere of H$_2$ at 1 atm. The suspension was purged with nitrogen and filtered through celite. The filtrate was concentrated and the crude product was used without further purification. MS (m/z) 728 [M+H]$^+$. The crude product was redissolved in 1 ml of tetrahydrofuran and 1 ml of methanol and 2 ml of 2N (aq.) lithium hydroxide was added to the solution. The solution was heated at 60° C. for 2 hours. The solution was cooled in an ice bath and acidified with 1N (aq) HCl. The resulting mixture was extracted with EtOAc (2×25 ml). The organic layer was dried over Na$_2$SO$_4$, filtered and concentrated. TFA (2 ml) was added to the crude product. After 20 minutes, the solvent was removed and the residue was dried under high vacuum. The crude product was used without further purification. The crude product yield was (100 mg, 0.2 mmol). MS (m/z) 500 [M+H]$^+$.

Synthesis of (4S)—N-(4-methoxyphenyl)-N-methyl-2-oxo-2,3,4,5,11,12,13,14-octahydro-1H-6,10-(metheno)azacyclopentadecino[5,4-b]indole-4-carboxamide (1)

To a solution of (S)-2-(2-(3-(3-(2-amino-3-((4-methoxyphenyl)(methyl)amino)-3-oxopropyl)phenyl)propyl)-1H-indol-3-yl)acetic acid (100 mg, 0.2 mmol) and DIPEA (0.35 ml, 2 mmol) in DMF (65 ml), was added diphenylphosphoryl azide (275 mg, 1 mmol) in 2 ml of DMF dropwise. The reaction was stirred overnight at room temperature. 1 ml of acetic acid and 5 ml of methanol was added to the mixture to quench the reaction. The solvent was removed in vacuo and the residue was dissolved in EtOAc (50 ml). The solution was washed with brine. The organic layer was dried over Na$_2$SO$_4$, filtered and concentrated. The crude product was introduced to a silica gel loading column and purified by column chromatography (1-5% MeOH/DCM). A DMF solution of the purified product was filtered and purified by RP HPLC using a C18 column and a gradient of 20% B to 85% B over 25 minutes (A=0.1% TFA/H$_2$O, B=0.1% TFA/acetonitrile) to provide the desired product. The yield was 23 mg of the TFA salt. MS (m/z) 482 [M+H]$^+$.

The procedures used to prepare (4S)—N-(4-methoxyphenyl)-N-methyl-2-oxo-2,3,4,5,11,12,13,14-octahydro-1H-6,10-(metheno)azacyclopentadecino[5,4-b]indole-4-carboxamide (1) were also used to prepare compounds 2, 3 and 4 of Examples 2, 3 and 4. The benzyl protecting group of Example 2 was removed concurrently during hydrogenolysis of olefin intermediate.

| Example | Structure | | Exact Mass | Observed Mass M + 1 | Retention time (min) |
|---|---|---|---|---|---|
| Example 1 | 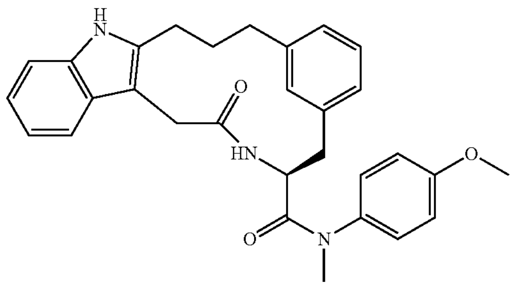 [SMILES: COc1ccc(N(C)C(=O)[C@@H]2Cc3cccc(c3)CCCc3[nH]c4ccccc4c3CC(=O)N2)cc1] | 1 | 481 | 482 | 1.55 |
| Example 2 | 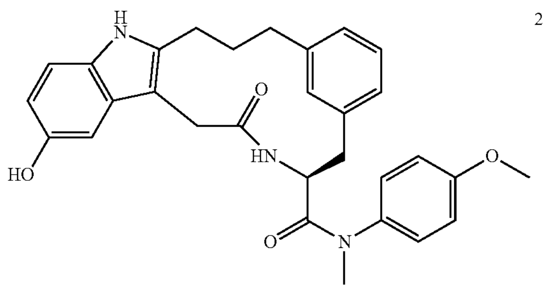 | 2 | 497 | 498 | 1.33 |
| Example 3 | 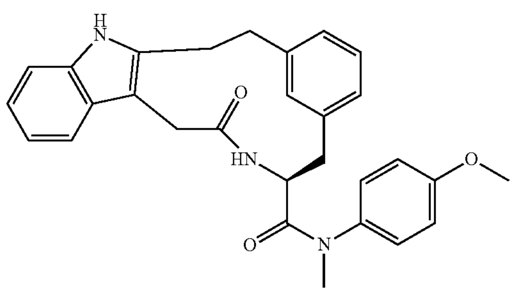 [SMILES: COc1ccc(N(C)C(=O)[C@@H]2Cc3cccc(c3)CCc3[nH]c4ccccc4c3CC(=O)N2)cc1] | 3 | 467 | 468 | 1.46 |
| Example 4 | 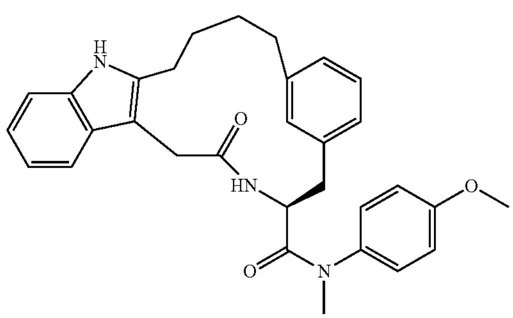 [SMILES: COc1ccc(N(C)C(=O)[C@@H]2Cc3cccc(c3)CCCCc3[nH]c4ccccc4c3CC(=O)N2)cc1] | 4 | 495 | 496 | 1.6 |
Intermediate I-1A
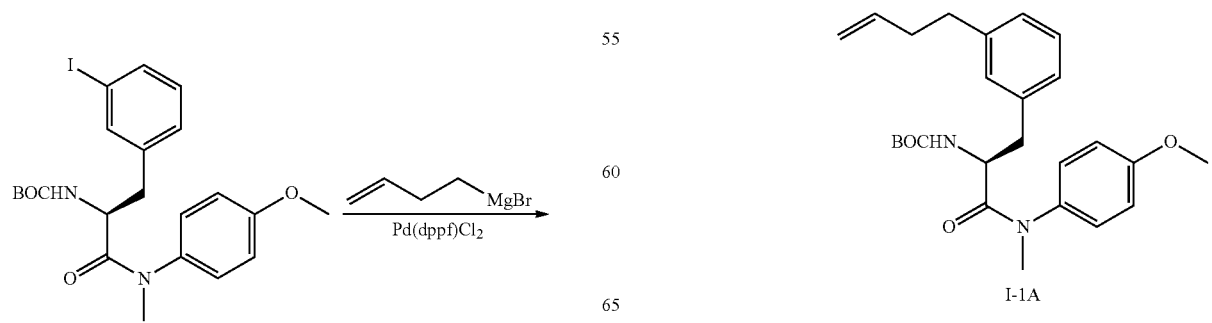

Synthesis of (5)-tert-butyl 3-(3-(but-3-enyl)phenyl)-1-((4-methoxyphenyl)(methyl)amino)-1-oxopropan-2-ylcarbamate To a solution of (5)-tert-butyl 3-(3-iodophenyl)-1-((4-methoxyphenyl)(methyl)amino)-1-oxopropan-2-ylcarbamate (510 mg, 1.0 mmol), Pd(dppf)Cl$_2$ (10 mol %) in THF (5 ml) was added but-3-enylmagnesium bromide (8 ml, 4 mmol, 0.5 M in THF). The solution was then heated at reflux overnight. The solution was cooled down and quenched with ammonia chloride (aq) and filtered through celite. The filtrate was extracted with EtOAc (2×25 ml). The organic layer was dried over Na$_2$SO$_4$, filtered and concentrated. The crude product was introduced to a silica gel loading column and purified by column chromatography (20-40% EtOAc/hexanes) to provide the desired product (270 mg, 0.62 mmol), 62%. MS (m/z) 439 [M+H]$^+$. Intermediate I-1A was used in the synthesis of Example 4.

Intermediate I-1B

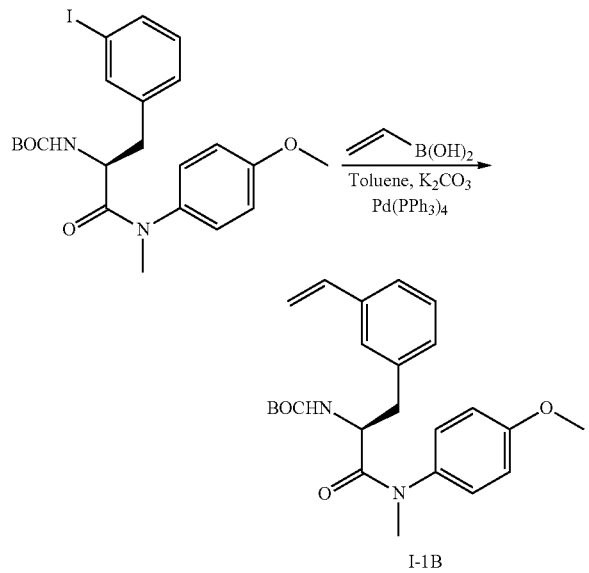

I-1B

The synthesis of Intermediate I-1B was analogous to the synthesis of (5)-tert-butyl 3-(3-allylphenyl)-1-((4-methoxyphenyl)(methyl)amino)-1-oxopropan-2-ylcarbamate of Example 1. Yield=99%, MS (m/z) 411 [M+H]$^+$, Intermediate I-1B was used in the synthesis of Example 3.

Intermediate I-2A and I-2B

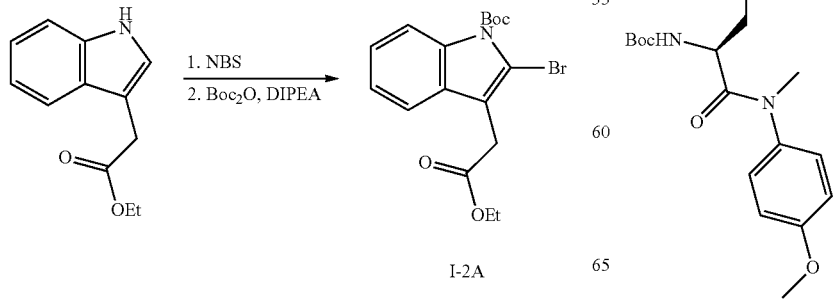

I-2A

Synthesis of tert-butyl 2-bromo-3-(2-ethoxy-2-oxoethyl)-1H-indole-1-carboxylate (2A)

To a solution of ethyl 2-(1H-indol-3-yl)acetate (5 g, 24.6 mmol) in 25 ml of DCM was added N-bromosuccinimide (4.38 g, 24.6 mmol) in small portions at 0° C. The mixture was warmed to room temperature and stirred for 6 hours. Di-tert-butyl pyrocarbonate (10.74 g, 49.2 mmol), DIPEA (8.6 ml, 49.5 mmol) and DMAP (cat) was added to the mixture. The reaction was stirred overnight. The mixture was diluted with DCM (100 ml) and washed with HCl (0.5 N, 2×50 ml). The organic layer was dried with Na$_2$SO$_4$, filtered and concentrated. The crude product was introduced to a silica gel loading column and purified by column chromatography on silica (5-20 EtOAc/hexanes) to get 6.3 g (16.5 mmol) of product. MS (m/z) 382 [M+H]$^+$.

The procedure to synthesize ethyl tert-butyl 2-bromo-3-(2-ethoxy-2-oxoethyl)-1H-indole-1-carboxylate (I-2A) was also used to prepare intermediate I-2B.

| Structure | | Exact Mass | Observed Mass M + 1 |
|---|---|---|---|
| (Boc-indole-Br with OEt ester) | I-2A | 381 | 382 |
| (BnO-Boc-indole-Br with OEt ester) | I-2B | 487 | 488 |

Examples 5-14

Preparation of Compounds 5-14

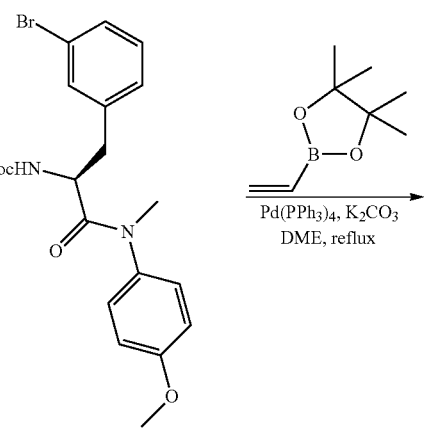

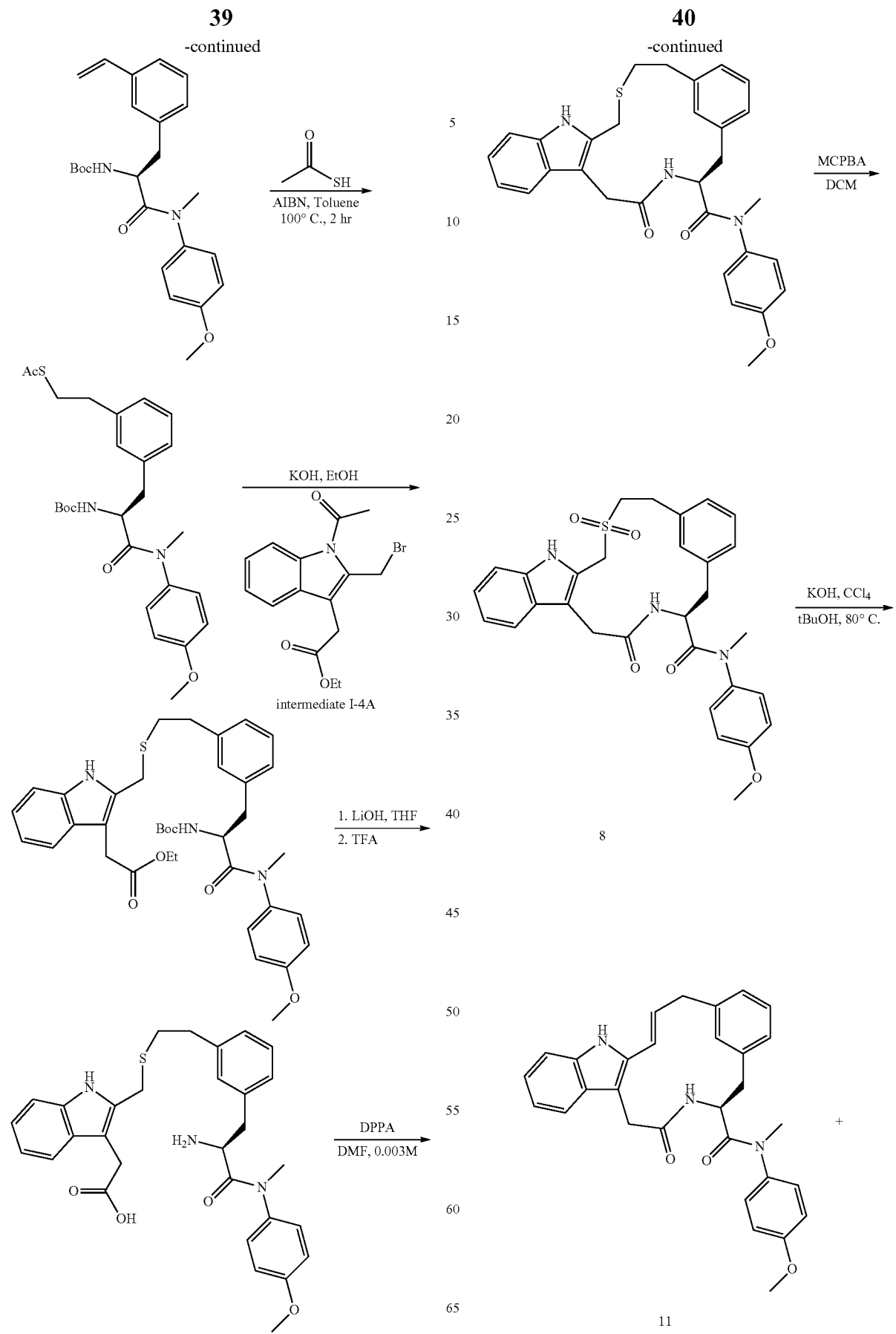

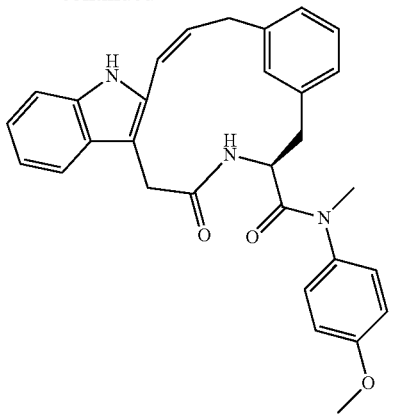

13

Synthesis of (5)-tert-butyl 1-((4-methoxyphenyl)(methyl)amino)-1-oxo-3-(3-vinylphenyl)propan-2-ylcarbamate A suspension of (S)-tert-butyl 3-(3-bromophenyl)-1-((4-methoxyphenyl)(methyl)amino)-1-oxopropan-2-ylcarbamate (6.3 g, 13.6 mmol), 4,4,5,5-tetramethyl-2-vinyl-1,3,2-dioxaborolane (3.3 g, 20.4 mmol), potassium carbonate (54 ml, 0.4 M) and tetrakis(triphenylphosphine)palladium(0) (0.79 g, 0.68 mmol) in 50 ml of DME, was heated at reflux overnight. The suspension was cooled and filtered through celite. The filtrate was washed with brine and filtered through celite. The organic layer was dried over $Na_2SO_4$, filtered and concentrated. The crude product was introduced to a silica gel loading column and purified by column chromatography (15-35% EtOAc/hexanes) to provide the desired product (5.47 g, 13.33 mmol), 94%. MS (m/z) 411 $[M+H]^+$.

Synthesis of (S)—S-3-(2-(tert-butoxycarbonylamino)-3-((4-methoxyphenyl)(methyl)amino)-3-oxopropyl)phenethyl ethanethioate To a solution of (5)-tert-butyl 1-((4-methoxyphenyl)(methyl)amino)-1-oxo-3-(3-vinylphenyl)propan-2-ylcarbamate (2.9 g, 7.06 mmol) and thioacetic acid (5 ml) in toluene (30 ml), was added azobisisobutyronitrile, (3.2 ml, 0.2M in toluene) dropwise. The solution was degassed for 30 minutes by purging with nitrogen. After purging was complete, the reaction was heated at 100° C. for 2 hours. The reaction was cooled to room temperature and then diluted with EtOAc (100 ml). The organics were washed with sodium bicarbonate (3×). The organic layer was dried with $Na_2SO_4$, filtered and concentrated. The crude product was introduced to a silica gel loading column and purified by column chromatography (20-50% EtOAc/hexanes) to provide the desired product (2.8 g, 5.74 mmol), 81.4%. MS (m/z) 487 $[M+H]^+$.

Synthesis of (S)-ethyl 2-(2-((3-(2-(tert-butoxycarbonylamino)-3-((4-methoxyphenyl)(methyl)amino)-3-oxopropyl)phenethylthio)methyl)-1H-indol-3-yl)acetate To a solution of (S)—S-3-(2-(tert-butoxycarbonylamino)-3-((4-methoxyphenyl)(methyl)amino)-3-oxopropyl)phenethyl ethanethioate (2.8 g, 5.74 mmol) in ethanol (20 ml) was added potassium hydroxide (0.64 g, 11.4 mmol). After 10 minutes, ethyl 2-(1-acetyl-2-(bromomethyl)-1H-indol-3-yl)acetate (2.2 g, 6.47 mmol) was added to the solution. The reaction was stirred for 2 hours at room temperature. The reaction was neutralized with 1N (aq) HCl and then extracted with EtOAc. The organic layer was dried over $Na_2SO_4$, filtered and concentrated. The crude product was introduced to a silica gel loading column and purified by column chromatography (3-6% MeOH/DCM) to provide the desired product (2.0 g, 3.0 mmol), 52.3%. MS (m/z) 660 $[M+H]^+$.

Synthesis of (S)-2-(2-((3-(2-amino-3-((4-methoxyphenyl)(methyl)amino)-3-oxopropyl)phenethylthio)methyl)-1H-indol-3-yl)acetic acid To a solution of (S)-ethyl 2-(2-((3-(2-(tert-butoxycarbonylamino)-3-(4-methoxyphenyl)(methyl)amino)-3-oxopropyl)phenethylthio)methyl)-1H-indol-3-yl)acetate (2.0 g, 3.0 mmol) in 3 ml of tetrahydrofuran and 3 ml of methanol was added 6 ml of 2 N lithium hydroxide. The reaction was heated at 60° C. for 2 hours. After cooling to room temperature, the mixture was acidified with 1N (aq) HCl and then extracted with EtOAc (2×50 ml). The organic layer was dried over $Na_2SO_4$, filtered and concentrated. TFA (5 ml) was added to the crude product. After 20 minutes the solvent was removed and the residue dried under high vacuum. The crude product was dissolved in DMF and the solution was filtered and purified by RP HPLC using a C18 column and a gradient of 20% B to 85% B over 25 minutes (A=0.1% $TFA/H_2O$, B=0.1% TFA/acetonitrile) to provide the desired product (380 mg, 0.71 mmol). MS (m/z) 532 $[M+H]^+$.

Synthesis of (11S)—N-(4-methoxyphenyl)-N-methyl-13-oxo-3,4,10,11,12,13,14,19-octahydro-1H-9,5-(metheno)[1,7]thiazacyclohexadecino[3,4-b]indole-11-carboxamide To a solution of (S)-2-(2-((3-(2-amino-3-((4-methoxyphenyl)(methyl)amino)-3-oxopropyl)phenethylthio)methyl)-1H-indol-3-yl)acetic acid (380 mg, 0.71 mmol) and DIPEA (1.23 ml, 7.1 mmol) in DMF (236 ml) was added diphenylphosphoryl azide (976 mg, 3.55 mmol) in 5 ml of DMF dropwise. The reaction was stirred overnight at room temperature and then 1 ml of acetic acid and 5 ml of methanol were added to quench the reaction. The solvent was removed in vacuo and the residue dissolved in EtOAc (100 ml) and washed with brine. The organic layer was dried over $Na_2SO_4$, filtered and concentrated. The crude product was introduced to a silica gel loading column and purified by column chromatography (1-5% MeOH/DCM). The purified product was dissolved in DMF and the solution was filtered and purified by RP HPLC using a C18 column and a gradient of 20% B to 85% B over 25 minutes (A=0.1% $TFA/H_2O$, B=0.1% TFA/acetonitrile). The yield was 240 mg of the TFA salt. MS (m/z) 514 $[M+H]^+$.

Synthesis of (11S)—N-(4-methoxyphenyl)-N-methyl-13-oxo-3,4,10,11,12,13,14,19-octahydro-1H-9,5-(metheno)[1,7]thiazacyclohexadecino[3,4-b]indole-11-carboxamide 2,2-dioxide To a solution of (11S)—N-(4-methoxyphenyl)-N-methyl-13-oxo-3,4,10,11,12,13,14,19-octahydro-1H-9,5-(metheno)[1,7]thiazacyclohexadecino[3,4-b]indole-11-carboxamide (240 mg, 0.47 mmol) in DCM (5 ml) was added meta-chloroperoxybenzoic acid (210 mg, 77%, 0.93 mmol). The reaction was stirred for 2 hours and then diluted with DCM (20 ml) and washed with $NaHCO_3$ (aq) and brine. The organic layer was dried over Na₂SO₄, filtered and concentrated. The crude product was introduced to a silica gel loading column and purified by column chromatography (1-5% MeOH/DCM). The yield was 250 mg. MS (m/z) 546 [M+H]⁺.

Synthesis of E isomer: (4S,12E)-N-(4-methoxyphenyl)-N-methyl-2-oxo-2,3,4,5,11,14-hexahydro-1H-6,10-(metheno)azacyclopentadecino[5,4-b]indole-4-carboxamide and Z isomer (4S,12Z)—N-(4-methoxyphenyl)-N-methyl-2-oxo-2,3,4,5,11,14-hexahydro-1H-6,10-(metheno)azacyclopentadecino[5,4-b]indole-4-carboxamide: Finely powdered KOH (448 mg, 8 mmol, 20 equiv) was added in a single portion to a solution of a portion of (11S)—N-(4-methoxyphenyl)-N-methyl-13-oxo-3,4,10,11,12,13,14,19-octahydro-1H-9,5-(metheno)[1,7]thiazacyclohexadecino[3,4-b]indole-11-carboxamide 2,2-dioxide (215 mg, 0.4 mmol) in a mixture of CCl₄/t-BuOH/H₂O (5/5/1, 4 mL/4 mL/0.8 mL) at 25° C. The resultant slurry was stirred for 1 hr at 80° C. Upon completion, the reaction mixture was quenched with saturated aqueous NH₄Cl (10 mL), poured into water (10 mL), and extracted with EtOAc (30 ml). The organic layers were then washed with water (200 mL) and brine (200 mL), dried over Na₂SO₄, filtered and concentrated. The product was dissolved in DMF and the solution was filtered and purified by RP HPLC using a C18 column and a gradient of 20% B to 85% B over 25 minutes (A=0.1% TFA/H₂O, B=0.1% TFA/acetonitrile). The yield was 9 mg of the TFA salt as a mixture of Z and E isomers. Repurification gave 2 mg pure E isomer and 3.6 mg pure Z isomer. MS (m/z) 480 [M+H]⁺

The procedures used to prepare (11S)—N-(4-methoxyphenyl)-N-methyl-13-oxo-3,4,10,11,12,13,14,19-octahydro-1H-9,5-(metheno)[1,7]thiazacyclohexadecino[3,4-b]indole-11-carboxamide (Example 5) were also used to prepare the compounds of Examples 6 and 7 using the corresponding intermediates I-4B and I-4C.

| Example | Structure | | Exact Mass | Observed Mass M + 1 | Retention time (min) |
|---|---|---|---|---|---|
| Example 5 | 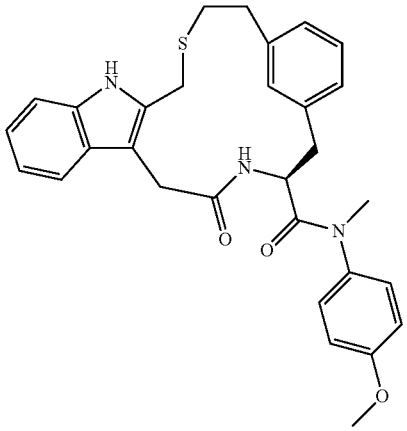 [SMILES: COc1ccc(N(C)C(=O)[C@@H]2Cc3cccc(c3)CCSCc3[nH]c4ccccc4c3CC(=O)N2)cc1] | 5 | 513 | 514 | 1.45 |
| Example 6 | 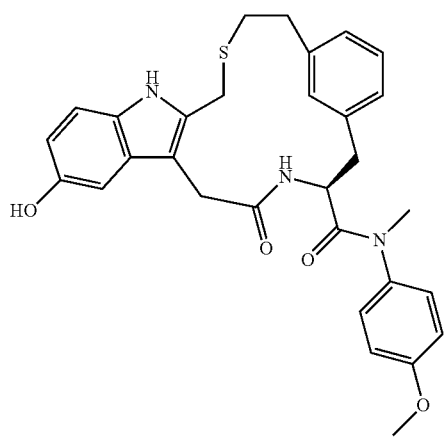 [SMILES: COc1ccc(N(C)C(=O)[C@@H]2Cc3cccc(c3)CCSCc3[nH]c4ccc(O)cc4c3CC(=O)N2)cc1] | 6 | 529 | 530 | 1.3 |

-continued

| Example | Structure | Exact Mass | Observed Mass M + 1 | Retention time (min) |
|---|---|---|---|---|
| Example 7 | 7 | 531 | 532 | 1.49 |

The procedures used to prepare (11S)—N-(4-methoxyphenyl)-N-methyl-13-oxo-3,4,10,11,12,13,14,19-octahydro-1H-9,5-(metheno) [1,7]thiazacyclohexadecino[3,4-b]indole-11-carboxamide 2,2-dioxide were also used to prepare the compounds of Examples 9 and 10.

| Example | Structure | Exact Mass | Observed Mass M + 1 | Retention time (min) |
|---|---|---|---|---|
| Example 8 | 8 | 545 | 546 | 1.2 |
| Example 9 | 9 | 561 | 562 | 1.08 |

| Example | Structure | | Exact Mass | Observed Mass M + 1 | Retention time (min) |
|---|---|---|---|---|---|
| Example 10 | 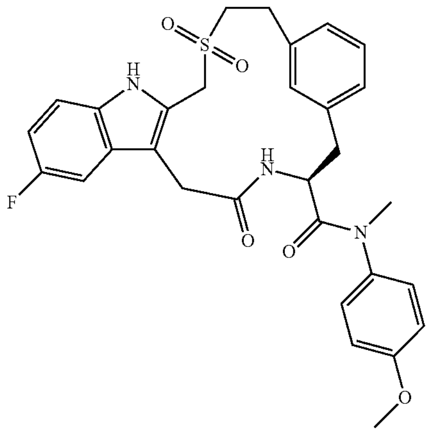 [SMILES: COc1ccc(N(C)C(=O)[C@@H]2Cc3cccc(c3)CCS(=O)(=O)Cc3[nH]c4ccc(F)cc4c3CC(=O)N2)cc1] | 10 | 563 | 564 | 1.26 |

The procedures used to prepare (4S,12E)-N-(4-methoxyphenyl)-N-methyl-2-oxo-2,3,4,5,11,14-hexahydro-1H-6,10-(metheno)azacyclopentadecino[5,4-b]indole-4-carboxamide and (4S,12Z)—N-(4-methoxyphenyl)-N-methyl-2-oxo-2,3,4,5,11,14-hexahydro-1H-6,10-(metheno) azacyclopentadecino[5,4-b]indole-4-carboxamide (11) were also used to prepare the compounds of Examples 12, 13 and 14.

| Example | Structure | | Exact Mass | Observed Mass M + 1 | Retention time (min) |
|---|---|---|---|---|---|
| Example 11 | 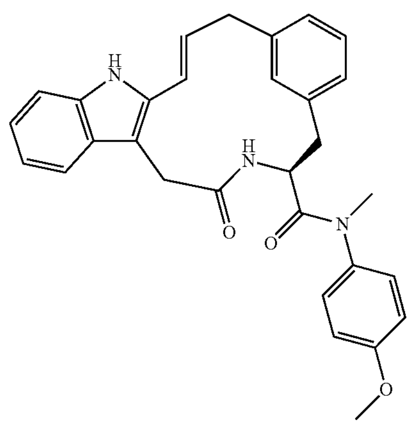 [SMILES: COc1ccc(N(C)C(=O)[C@@H]2Cc3cccc(c3)C/C=C/c3[nH]c4ccccc4c3CC(=O)N2)cc1] | 11 | 479 | 480 | 1.41 |
| Example 12 | 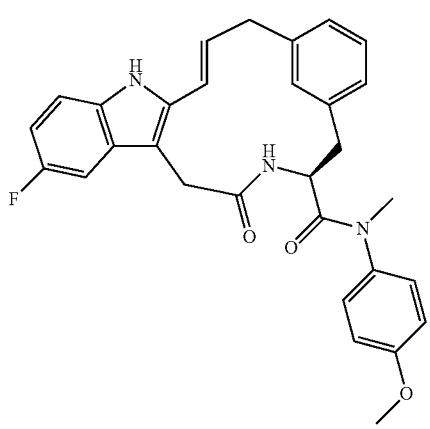 [SMILES: COc1ccc(N(C)C(=O)[C@@H]2Cc3cccc(c3)C/C=C/c3[nH]c4ccc(F)cc4c3CC(=O)N2)cc1] | 12 | 497 | 498 | 1.47 |

| Example | Structure | | Exact Mass | Observed Mass M + 1 | Retention time (min) |
|---|---|---|---|---|---|
| Example 13 | 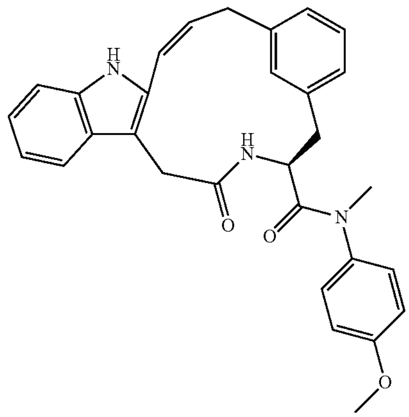 [SMILES: COc1ccc(N(C)C(=O)[C@@H]2Cc3cccc(c3)C/C=C\c3[nH]c4ccccc4c3CC(=O)N2)cc1] | 13 | 479 | 480 | 1.42 |
| Example 14 | 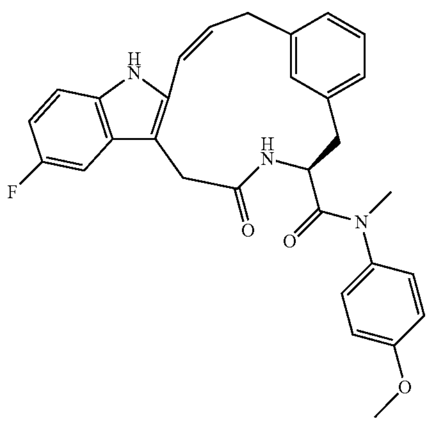 [SMILES: COc1ccc(N(C)C(=O)[C@@H]2Cc3cccc(c3)C/C=C\c3[nH]c4ccc(F)cc4c3CC(=O)N2)cc1] | 14 | 497 | 498 | 1.48 |

Intermediate I-3A and I-3B

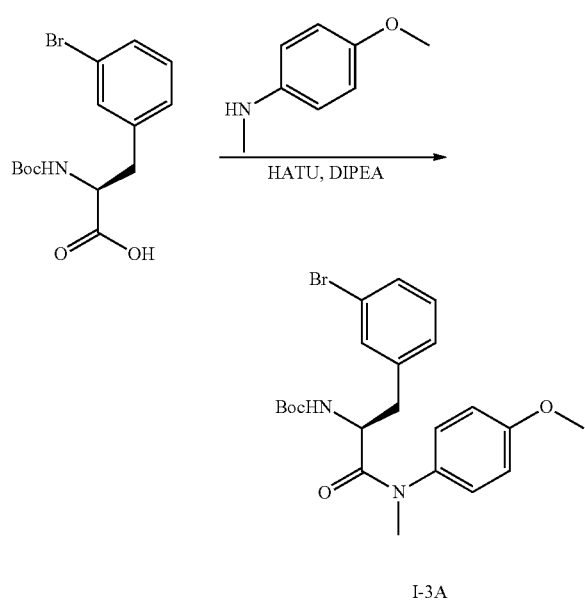

Synthesis of (S)-tert-butyl 3-(3-bromophenyl)-1-((4-methoxyphenyl)(methyl)amino)-1-oxopropan-2-ylcarbamate: (S)-2-(tert-Butoxycarbonylamino)-3-(3-bromophenyl)propanoic acid (660 mg, 1.92 mmol), O-(7-azabenzotriazol-1-yl)-N,N,N',N'-tetramethyluronium hexafluorophosphate (HATU, 803 mg, 2.1 mmol) and DIPEA (0.43 ml, 2.5 mmol) were dissolved in DMF (10 ml) and treated with 4-methoxy-N-methylaniline (316 g, 2.3 mmol). The mixture was stirred vigorously overnight. The mixture was diluted with EtOAc (100 ml) and washed with brine (2×50 ml). The organic layer was dried over $Na_2SO_4$, filtered and concentrated. The oily crude product was introduced to a silica gel loading column and purified by column chromatography (15-38% EtOAc/hexanes) to provide the desired product (770 mg, 1.66 mmol), 86.5%. MS (m/z) 463 [M+H]$^+$.

The procedure used to synthesize (S)-tert-butyl 3-(3-bromophenyl)-1-((4-methoxyphenyl)(methyl)amino)-1-oxopropan-2-ylcarbamate (I-3A) was also used to prepare intermediate I-3B.

| Intermediate | | Exact Mass | Observed Mass M + 1 |
|---|---|---|---|
| | I-3A | 462 | 463 |
| | I-3B | 409 | 410 |

Intermediate I-4A, I-4B and I-4C

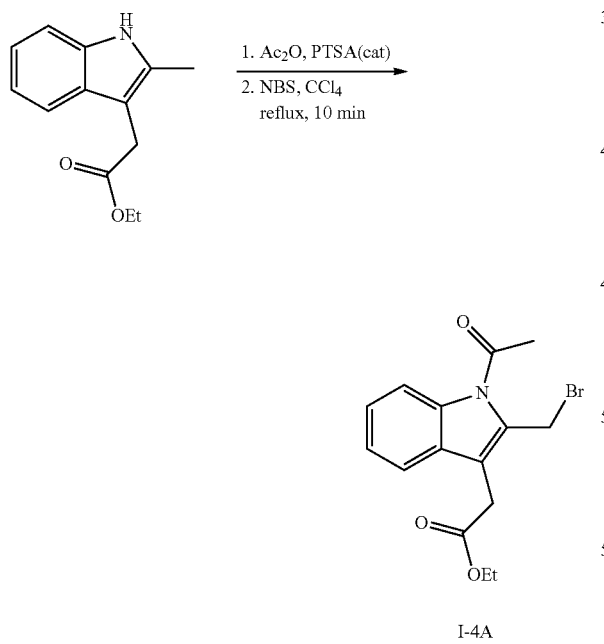

I-4A

Synthesis of ethyl 2-(1-acetyl-2-(bromomethyl)-1H-indol-3-yl)acetate

To a solution of ethyl 2-(2-methyl-1H-indol-3-yl)acetate (5 g, 23 mmol) in 30 ml of acetic anhydride was added p-toluenesulfonic acid monohydrate (cat). The reaction was heated to 80° C. for 1 hour. The reaction was cooled to room temperature and the acetic anhydride was removed in vacuo. The residue was dissolved in EtOAc (200 ml) and washed with sodium bicarbonate (aq) and brine. The organic layer was dried over $Na_2SO_4$, filtered and concentrated. The crude product was introduced to a silica gel loading column and purified by column chromatography (20-40 EtOAc/hexanes) to get 3 g (11.54 mmol) product. The product was dissolved in carbon tetrachloride (24 ml) and N-bromosuccinimide (2.05 g, 11.54 mmol) was added to the solution. The reaction was heated at reflux for 30 minutes. The solvent was removed in vacuo. The crude product was introduced to a silica gel loading column and purified by column chromatography (30-50 EtOAc/hexanes) to get 3 g (8.88 mmol) product. MS (m/z) 338 $[M+H]^+$.

The procedure used to synthesize ethyl 2-(1-acetyl-2-(bromomethyl)-1H-indol-3-yl)acetate (I-4A) was also used to prepare intermediates I-4B and I-4C.

| Intermediate | | Exact Mass | Observed Mass M + 1 |
|---|---|---|---|
| | I-4A | 337 | 338 |
| | I-4B | 355 | 356 |
| | I-4C | 353 | 354 |

Examples 15-17

Preparation of Compounds 15-17

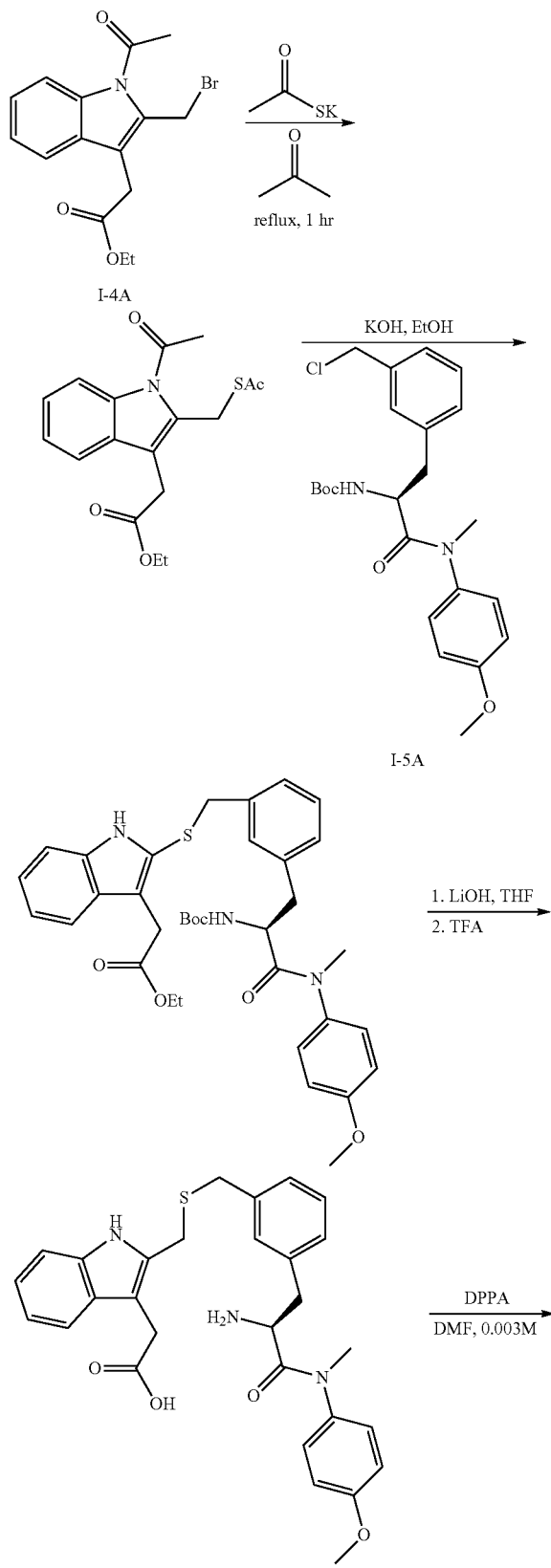

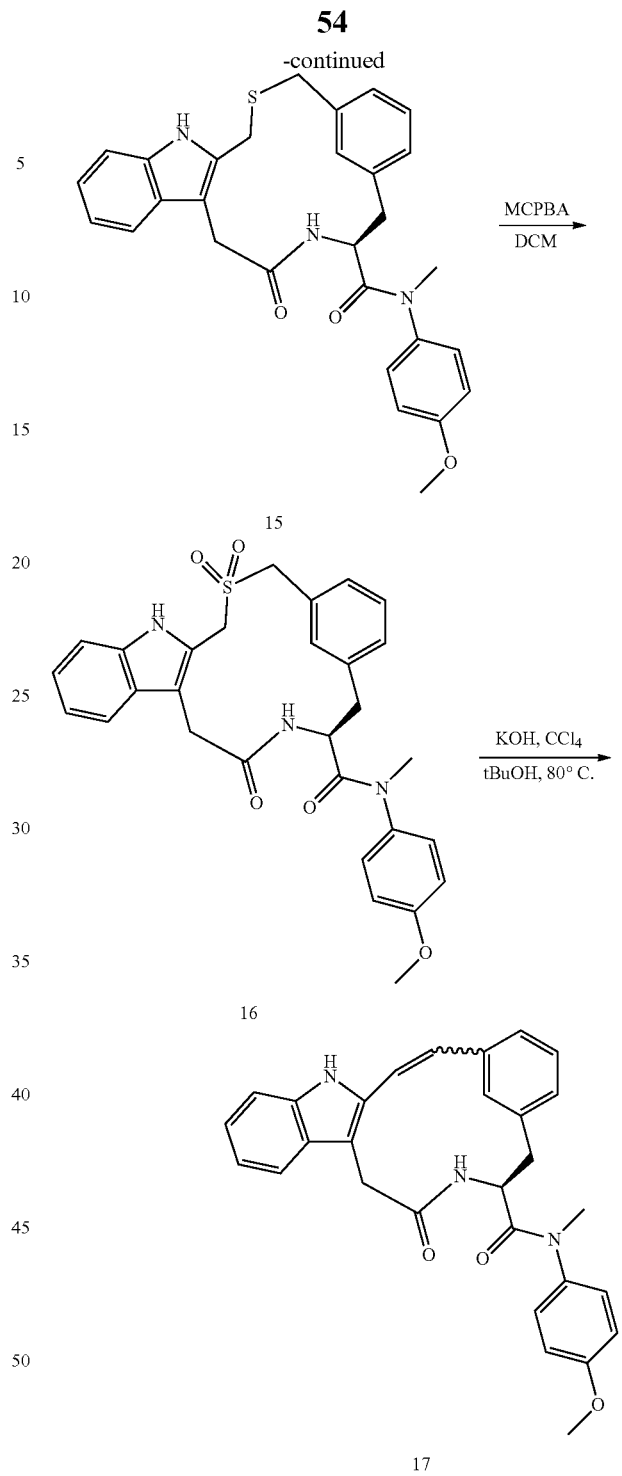

Synthesis of ethyl 2-(1-acetyl-2-(acetylthiomethyl)-1H-indol-3-yl)acetate

To a solution of ethyl 2-(1-acetyl-2-(bromomethyl)-1H-indol-3-yl)acetate (I-4A, 640 mg, 1.9 mmol) in acetone (10 ml) was added potassium ethanethioate (1.3 g, 11.2 mmol). The solution was heated at reflux for 1 hour. The solution was cooled and then diluted with EtOAc (50 ml) and washed with NaHCO$_3$ (aq) (2×25 ml). The organic layer was dried with Na$_2$SO$_4$, filtered and concentrated. The crude product was introduced to a silica gel loading column and purified by column chromatography (10-30 EtOAc/hexanes) to get 533 mg (1.6 mmol, 84%) product. MS (m/z) 334 [M+H]$^+$.

Synthesis of (S)-ethyl 2-(2-((3-(2-(tert-butoxycarbonylamino)-3-((4-methoxyphenyl)(methyl)amino)-3-oxopropyl)benzylthio)methyl)-1H-indol-3-yl)acetate To a solution 2-(1-acetyl-2-(acetylthiomethyl)-1H-indol-3-yl)acetate (392 mg, 1.17 mmol) in ethanol (10 ml), was added potassium hydroxide (0.13 g, 2.32 mmol). After 10 minutes, (S)-tert-butyl 3-(3-(chloromethyl)phenyl)-1-((4-methoxyphenyl)(methyl)amino)-1-oxopropan-2-ylcarbamate (507 mg, 1.17 mmol) was added to the solution. The reaction was stirred for 2 hours and then neutralized with 1N (aq) HCl. The mixture was extracted with EtOAc. The organic layer was dried over $Na_2SO_4$, filtered and concentrated. The crude product was introduced to a silica gel loading column and purified by column chromatography (3-6% MeOH/DCM) to provide the desired product (650 mg, 1.0 mmol), 85%. MS (m/z) 646 [M+H]$^+$.

Synthesis of (S)-2-(2-((3-(2-amino-3-((4-methoxyphenyl)(methyl)amino)-3-oxopropyl)benzylthio)methyl)-1H-indol-3-yl)acetic acid To a solution of (S)-ethyl 2-(2-((3-(2-(tert-butoxycarbonylamino)-3-(4-methoxyphenyl)(methyl)amino)-3-oxopropyl)benzylthio)methyl)-1H-indol-3-yl)acetate (650 mg, 1.0 mmol) in 1 ml of tetrahydrofuran was added 1 ml of methanol and 2 ml of 2N (aq) LiOH. The reaction was heated at 60° C. for 2 hours. The reaction was cooled to room temperature and then acidified with 1N (aq) HCl. The mixture was extracted with EtOAc (2×50 ml). The organic layer was dried over $Na_2SO_4$, filtered and concentrated. TFA (5 ml) was added to the crude product. After 20 minutes, the solvent was removed and the residue was dried under high vacuum. The crude product was dissolved in DMF and the solution was filtered and purified by RP HPLC using a C18 column and a gradient of 20% B to 85% B over 25 minutes (A=0.1% TFA/$H_2O$, B=0.1% TFA/acetonitrile) to provide the desired product (160 mg, 0.31 mmol). MS (m/z) 518 [M+H]$^+$.

Synthesis of (10S)—N-(4-methoxyphenyl)-N-methyl-12-oxo-9,10,11,12,13,18-hexahydro-1H-8,4-(metheno)[1,7]thiazacyclopentadecino[3,4-b]indole-10(3H)-carboxamide To a solution of (S)-2-(2-((3-(2-amino-3-((4-methoxyphenyl)(methyl)amino)-3-oxopropyl)benzylthio)methyl)-1H-indol-3-yl)acetic acid (160 mg, 0.31 mmol) and DIPEA (0.54 ml, 3.1 mmol) in DMF (100 ml) was added diphenylphosphoryl azide (410 mg, 1.55 mmol) in 3 ml of DMF dropwise. The reaction was stirred overnight at room temperature and then 1 ml of acetic acid and 5 ml of methanol were added to quench the reaction. The solvent was removed and the residue dissolved in EtOAc (100 ml) and then washed with brine. The organic layer was dried over $Na_2SO_4$, filtered and concentrated. The crude product was introduced to a silica gel loading column and purified by column chromatography (1-5% MeOH/DCM). The product was dissolved in DMF and the solution was filtered and purified by RP HPLC using a C18 column and a gradient of 20% B to 80% B over 25 minutes (A=0.1% TFA/$H_2O$, B=0.1% TFA/acetonitrile). The yield was 76 mg of the TFA salt. MS (m/z) 500 [M+H]$^+$.

Synthesis of (10S)—N-(4-methoxyphenyl)-N-methyl-12-oxo-9,10,11,12,13,18-hexahydro-1H-8,4-(metheno)[1,7]thiazacyclopentadecino[3,4-b]indole-10(3H)-carboxamide 2,2-dioxide To a solution of (10S)—N-(4-methoxyphenyl)-N-methyl-12-oxo-9,10,11,12,13,18-hexahydro-1H-8,4-(metheno)[1,7]thiazacyclopentadecino[3,4-b]indole-10(3H)-carboxamide (24 mg, 0.048 mmol) in DCM (3 ml) was added meta-chloroperoxybenzoic acid (22 mg, 77%, 0.96 mmol). The reaction was stirred for 2 hours at room temperature, and then diluted with DCM (20 ml). The solution was washed with $NaHCO_3$ (aq), and brine. The organic layer was dried over $Na_2SO_4$, filtered and concentrated. The crude product was dissolved in DMF and the solution was filtered and purified by RP HPLC using a C18 column and a gradient of 20% B to 80% B over 25 minutes (A=0.1% TFA/$H_2O$, B=0.1% TFA/acetonitrile). The yield was 17 mg of the TFA salt. MS (m/z) 532 [M+H]$^+$.

Synthesis of (4S,11Z)—N-(4-methoxyphenyl)-N-methyl-2-oxo-1,2,3,4,5,13-hexahydro-6,10-(metheno)azacyclotetradecino[5,4-b]indole-4-carboxamide Finely powdered KOH (140 mg, 2.49 mmol, 22 equiv) was added in a single portion to a solution of a portion of (10S)—N-(4-methoxyphenyl)-N-methyl-12-oxo-9,10,11,12,13,18-hexahydro-1H-8,4-(metheno)[1,7]thiazacyclopentadecino[3,4-b]indole-10(3H)-carboxamide 2,2-dioxide (60 mg, 0.113 mmol) in a mixture of $CCl_4$/t-BuOH/$H_2O$ (5/5/1, 1 mL/1 mL/0.2 mL) at 25° C. The resultant slurry was then stirred for 1 h at 80° C. Upon completion, the reaction mixture was quenched with saturated aqueous $NH_4Cl$ (5 mL), poured into water (5 mL) and extracted with EtOAc (30 ml). The organic layer was washed with water (20 mL) and brine (20 mL), dried over $Na_2SO_4$, filtered and concentrated. The crude product was dissolved in DMF and the solution was filtered and purified by RP HPLC using a C18 column and a gradient of 20% B to 80% B over 25 minutes (A=0.1% TFA/$H_2O$, B=0.1% TFA/acetonitrile). The yield was 4 mg of the TFA salt as Z and E isomer mixture. MS (m/z) 466 [M+H]$^+$.

| Example | Structure | Exact Mass | Observed Mass M + 1 | Retention time (min) |
|---|---|---|---|---|
| Example 15 | 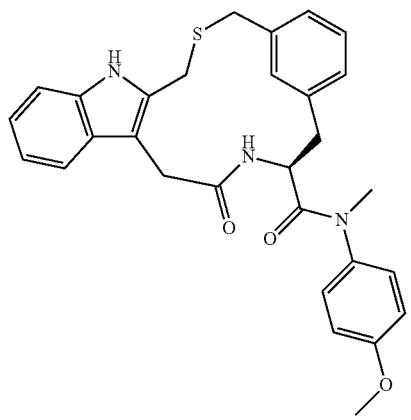 [SMILES: COc1ccc(N(C)C(=O)[C@@H]2Cc3cccc(c3)CSCc3[nH]c4ccccc4c3CC(=O)N2)cc1] | 499 | 500 | 1.45 |

| Example | Structure | Exact Mass | Observed Mass M + 1 | Retention time (min) |
|---|---|---|---|---|
| Example 16 | 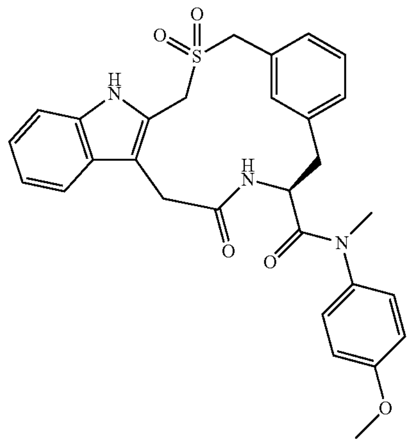 [SMILES: COc1ccc(N(C)C(=O)[C@@H]2Cc3cccc(c3)CS(=O)(=O)Cc3[nH]c4ccccc4c3CC(=O)N2)cc1] | 531 | 532 | 1.27 |
| Example 17 | 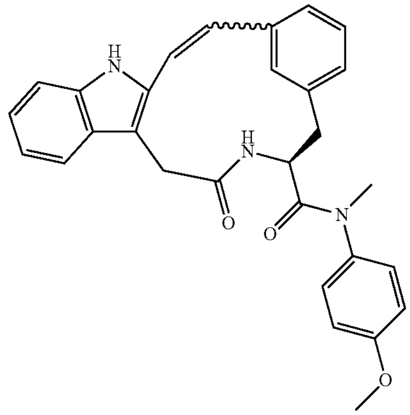 [SMILES: COc1ccc(N(C)C(=O)[C@@H]2Cc3cccc(c3)C=Cc3[nH]c4ccccc4c3CC(=O)N2)cc1] | 1.39 | 465 | 466 |
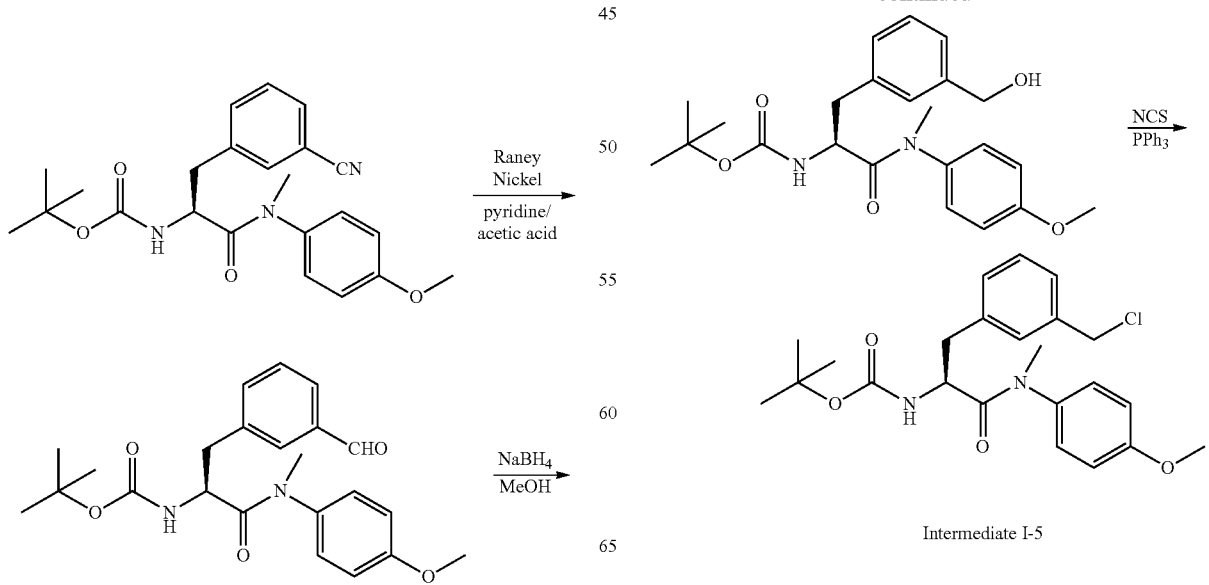
Intermediate I-5

Synthesis of (5)-tert-butyl 3-(3-formylphenyl)-1-((4-methoxyphenyl)(methyl)amino)-1-oxopropan-2-ylcarbamate (S)-tert-Butyl 3-(3-cyanophenyl)-1-((4-methoxyphenyl) (methyl)amino)-1-oxopropan-2-ylcarbamate (2.7 g, 6.60 mmole) was dissolved in pyridine (18.6 ml) and acetic acid (9.3 ml). Raney Nickel (2.7 g of a slurry in H$_2$O) was added and the resulting suspension was stirred at 46° C. overnight. The reaction was confirmed complete by reverse phase HPLC/MS. The reaction was cooled to room temperature and then filtered through celite. The filtrate was concentrated under reduced pressure and then partitioned between EtOAc and H$_2$O. The aqueous layer was extracted with EtOAc (3×). The combined organics were washed with H$_2$O (2×) and brine (2×). The organic layer was dried over MgSO$_4$, filtered and concentrated. The crude produce was dried under high vacuum overnight and used without further purification. Yield was 2.70 g. MS (m/z) 413 [M+H]$^+$.

Synthesis of (5)-tert-butyl 3-(3-(hydroxymethyl) phenyl)-1-((4-methoxyphenyl)(methyl)amino)-1-oxopropan-2-ylcarbamate (S)-tert-Butyl 3-(3-formylphenyl)-1-((4-methoxyphenyl) (methyl)amino)-1-oxopropan-2-ylcarbamate (2.71 g, 6.58 mmole) was dissolved in methanol (66 ml). The solution was cooled to 0° C. in an ice bath. NaBH$_4$ was added to the cooled solution and the resulting reaction mixture was stirred for 30 min. The reaction was confirmed to be complete by tlc and HPLC/MS. The reaction was concentrated under reduced pressure and then partitioned between EtOAc and H$_2$O. The aqueous layer was extracted with EtOAc (2×). The combined organics were washed with H$_2$O (2×) and brine (2×). The organic layer was dried over MgSO$_4$, filtered and concentrated. The crude product was purified by flash column using EtOAc/hexanes. Yield=1.3 g. MS (m/z) 415 [M+14]$^+$.

Synthesis of (5)-tert-butyl 3-(3-(chloromethyl)phenyl)-1-((4-methoxyphenyl)(methyl)amino)-1-oxopropan-2-ylcarbamate (S)-tert-Butyl 3-(3-(hydroxymethyl)phenyl)-1-((4-methoxyphenyl)(methyl)amino)-1-oxopropan-2-ylcarbamate (1.0 g, 2.42 mmole) was dissolved in CH$_2$Cl$_2$ (5 ml). Triphenylphosphine (666 mg, 2.54 mmole) was added followed by N-chlorosuccinimide (355 mg, 2.66 mmole). After the vigorous reaction subsided, TLC showed ~10% of unreacted starting material remained. Added 300 mg more N-chlorosuccinimide. TLC showed that the reaction was complete. The reaction mixture was purified without work-up by flash chromatography. Yield=1.0 g. MS (m/z) 433 [M+H]$^+$.

Examples 18-19

Preparation of Compounds 18-19

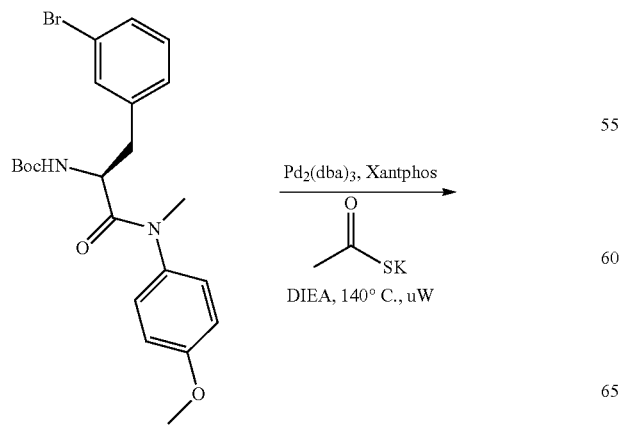

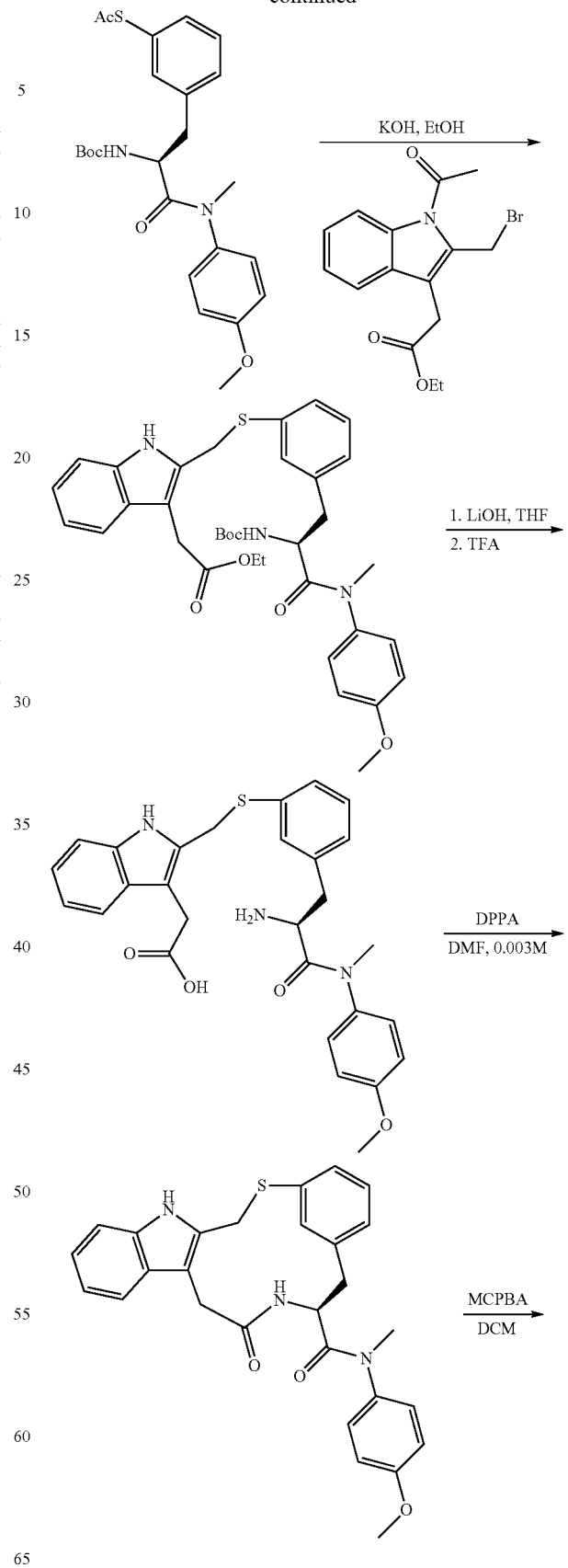

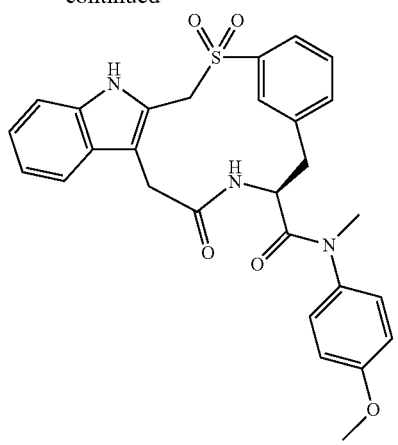

19

Synthesis of (S)—S-3-(2-(tert-butoxycarbonylamino)-3-((4-methoxyphenyl)(methyl)amino)-3-oxopropyl)phenyl ethanethioate A solution of (S)-tert-butyl 3-(3-bromophenyl)-1-((4-methoxyphenyl)(methyl)amino)-1-oxopropan-2-ylcarbamate (464 mg, 1.0 mmol), potassium ethanethioate (171.3 mg, 1.5 mmol), tris(dibenzylideneacetone)dipalladium(0) (46 mg, 0.05 mmol), xantphos (58 mg, 0.1 mmol) and DIPEA (0.35 ml, 2 mmol) in 1,4-dioxane (4 ml) was heated at 150° C. for 20 minutes in a microwave reactor. The mixture was filtered through celite and the celite was washed with EtOAc (2×50 ml). The organic layer was dried with Na$_2$SO$_4$, filtered and concentrated. The crude product was introduced to a silica gel loading column and purified by column chromatography (20-45% EtOAc/hexanes) to provide the desired product (300 mg, 0.65 mmol), 65%. MS (m/z) 459 [M+H]$^+$.

Synthesis of (S)-ethyl 2-(2-((3-(2-(tert-butoxycarbonylamino)-3-((4-methoxyphenyl)(methyl)amino)-3-oxopropyl)phenylthio)methyl)-1H-indol-3-yl)acetate To a solution of (S)—S-3-(2-(tert-butoxycarbonylamino)-3-((4-methoxyphenyl)(methyl)amino)-3-oxopropyl)phenyl ethanethioate (335 mg, 0.73 mmol) in ethanol (2 ml) was added potassium hydroxide (82 mg, 1.46 mmol). After 10 minutes, ethyl 2-(1-acetyl-2-(bromomethyl)-1H-indol-3-yl)acetate (I-4A, 272 mg, 0.8 mmol) was added. The reaction was stirred for 2 hours and then neutralized with 1N (aq) HCl then extracted with EtOAc. The organic layer was dried with Na$_2$SO$_4$, filtered and concentrated. The crude product was introduced to a silica gel loading column and purified by column chromatography (1-5% MeOH/DCM) to provide the desired product (347 mg, 0.55 mmol), 75.3%. MS (m/z) 632 [M+H]$^+$.

Synthesis of (S)-2-(2-((3-(2-amino-3-((4-methoxyphenyl)(methyl)amino)-3-oxopropyl)phenylthio)methyl)-1H-indol-3-yl)acetic acid To a solution of (S)-ethyl 2-(2-((3-(2-(tert-butoxycarbonylamino)-3-(4-methoxyphenyl)(methyl)amino)-3-oxopropyl)phenylthio)methyl)-1H-indol-3-yl)acetate (347 mg, 0.55 mmol) in 2 ml of tetrahydrofuran and 2 ml of methanol was added 4 ml of 2N LiOH. The reaction was heated at 60° C. for 2 hours, then cooled to room temperature and acidified with 1 N (aq) HCl. Extracted with EtOAc (2×50 ml). The organic layer was dried with Na$_2$SO$_4$ and concentrated. TFA (5 ml) was added to the crude product. After 20 minutes, the solvent was removed and the residue dried with high vacuum. The crude product was dissolved in DMF and the solution was filtered and purified by RP HPLC using a C18 column and a gradient of 20% B to 80% B over 25 minutes (A=0.1% TFA/H$_2$O, B=0.1% TFA/acetonitrile), to provide the desired product (111 mg, 0.22 mmol). MS (m/z) 504 [M+H]$^+$.

Synthesis (9S)—N-(4-methoxyphenyl)-N-methyl-11-oxo-8,9,10,11,12,17-hexahydro-1H-7,3-(metheno)[1,7]thiazacyclotetradecino[3,4-b]indole-9-carboxamide To a solution of (S)-2-(2-((3-(2-amino-3-((4-methoxyphenyl)(methyl)amino)-3-oxopropyl)phenylthio)methyl)-1H-indol-3-yl)acetic acid (111 mg, 0.22 mmol) and DIPEA (0.38 ml, 2.2 mmol) in DMF (70 ml) was added diphenylphosphoryl azide (292 mg, 1.1 mmol) in 3 ml of DMF dropwise. The reaction was stirred overnight at room temperature then 1 ml of acetic acid and 5 ml of methanol were added to quench the reaction. The solvent was removed in vacuo and the residue was dissolved in EtOAc (100 ml) then washed with brine. The organic layer was dried over Na$_2$SO$_4$, filtered and concentrated. The crude product was introduced to a silica gel loading column and purified by column chromatography (1-5% MeOH/DCM). The product was dissolved in DMF and the solution was filtered and purified by RP HPLC using a C18 column and a gradient of 20% B to 80% B over 25 minutes (A=0.1% TFA/H$_2$O, B=0.1% TFA/acetonitrile). The yield was 70 mg of the TFA salt. MS (m/z) 486 [M+H]$^+$.

Synthesis of (9S)—N-(4-methoxyphenyl)-N-methyl-11-oxo-8,9,10,11,12,17-hexahydro-1H-7,3-(metheno)[1,7]thiazacyclotetradecino[3,4-b]indole-9-carboxamide 2,2-dioxide To a solution (9S)—N-(4-methoxyphenyl)-N-methyl-11-oxo-8,9,10,11,12,17-hexahydro-1H-7,3-(metheno)[1,7]thiazacyclotetradecino[3,4-b]indole-9-carboxamide (29 mg, 0.06 mmol) in DCM (3 ml) was added meta-chloroperoxybenzoic acid (27.5 mg, 77%, 0.12 mmol). The reaction was stirred for 2 hours at room temperature, and then diluted with DCM (20 ml). The solution was washed with NaHCO$_3$ (aq), and brine. The organic layer was dried over Na$_2$SO$_4$, filtered and concentrated. The crude product was dissolved in DMF and the solution was filtered and purified by RP HPLC using a C18 column and a gradient of 20% B to 80% B over 25 minutes (A=0.1% TFA/H$_2$O, B=0.1% TFA/acetonitrile). The yield was 22 mg of the TFA salt. MS (m/z) 518 [M+H]$^+$.

| Example | Structure | Exact Mass | Observed Mass M + 1 | Retention time (min) |
|---|---|---|---|---|
| Example 18 | 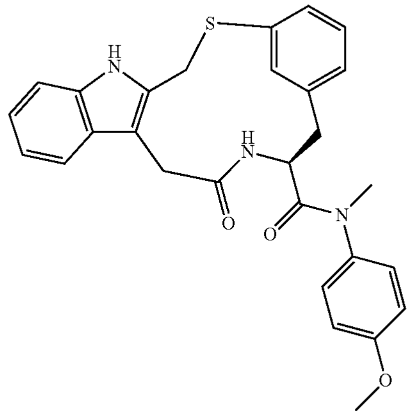 [SMILES: COc1ccc(N(C)C(=O)[C@@H]2Cc3cccc(c3)SCc3[nH]c4ccccc4c3CC(=O)N2)cc1] | 485 | 486 | 1.43 |
| Example 19 | 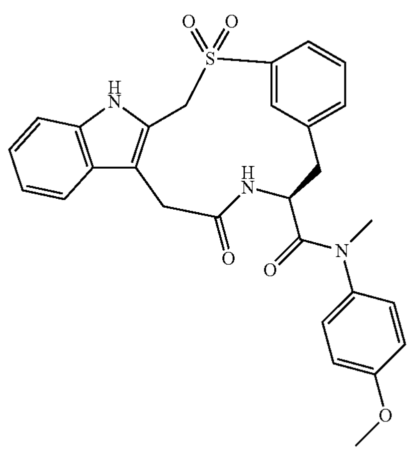 [SMILES: COc1ccc(N(C)C(=O)[C@@H]2Cc3cccc(c3)S(=O)(=O)Cc3[nH]c4ccccc4c3CC(=O)N2)cc1] | 517 | 518 | 1.25 |
Examples 20-21
Preparation of Compounds 20-21
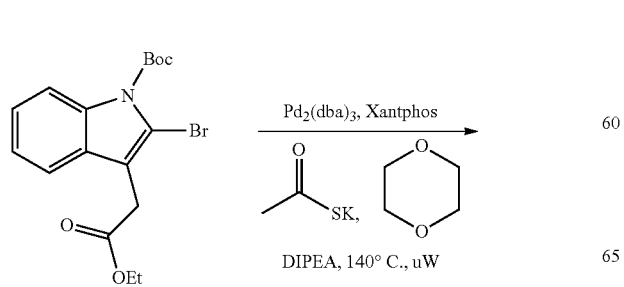
-continued
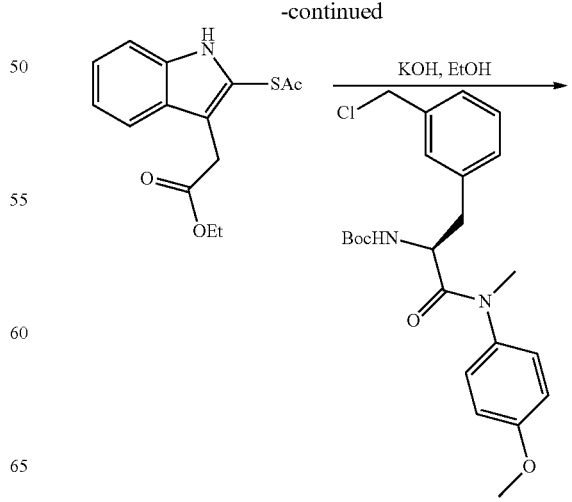

65

-continued

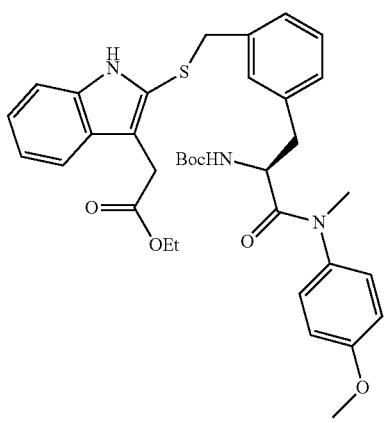

1. LiOH, THF
2. TFA →

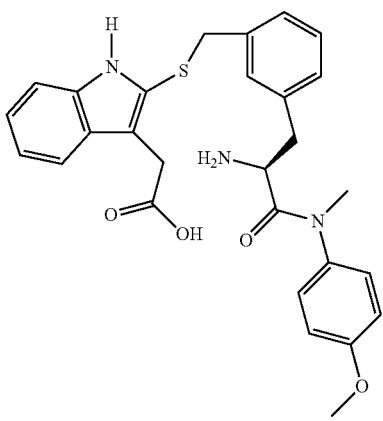

DPPA
DMF, 0.003M →

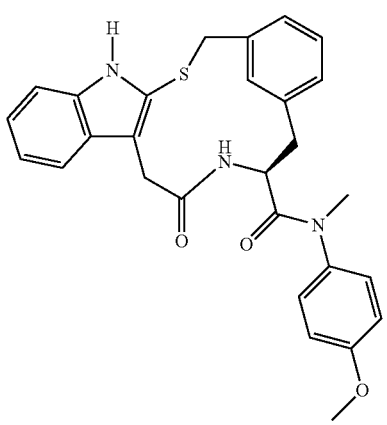

MCPBA
DCM →

66

-continued

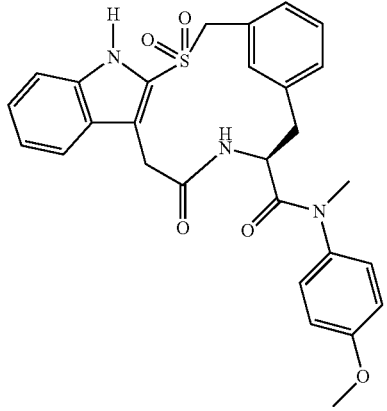

21

Synthesis of ethyl 2-(2-(acetylthio)-1H-indol-3-yl)acetate

A solution of tert-butyl 2-bromo-3-(2-ethoxy-2-oxoethyl)-1H-indole-1-carboxylate (500 mg, 1.3 mmol), potassium ethanethioate (200 mg, 1.7 mmol), tris(dibenzylideneacetone)dipalladium(0) (60 mg, 0.065 mmol), xantphos (75 mg, 0.13 mmol) and DIPEA (0.5 ml, 2.6 mmol) in 1,4-dioxane (4 ml), was heated at 150° C. for 20 minutes in a microwave reactor. TFA (5 ml) was added to the mixture and stirred for 1 hour until Boc deprotection was complete. Filtered reaction mixture through celite and washed with EtOAc (2×50 ml). The organic layer was dried over $Na_2SO_4$, filtered and concentrated. The crude product was introduced to a silica gel loading column and purified by column chromatography (10-30% EtOAc/Hexanes) to provide the desired product (190 mg, 0.69 mmol), 52.8%. MS (m/z) 278 $[M+H]^+$.

Synthesis of (S)-ethyl 2-(2-(3-(2-(tert-butoxycarbonylamino)-3-((4-methoxyphenyl)(methyl)amino)-3-oxopropyl)benzylthio)-1H-indol-3-yl)acetate To a solution ethyl 2-(2-(acetylthio)-1H-indol-3-yl)acetate (380 mg, 1.4 mmol) in ethanol (5 ml) was added potassium hydroxide (84 mg, 1.5 mmol). After 10 minutes, (S)-tert-butyl 3-(3-(chloromethyl)phenyl)-1-((4-methoxyphenyl)(methyl)amino)-1-oxopropan-2-ylcarbamate (I-5, 605 mg, 1.4 mmol) was added to the solution. The reaction was stirred for 2 hours and then neutralized with 1$\underline{N}$ (aq) HCl and then extracted with EtOAc. The organic layer was dried over $Na_2SO_4$, filtered and concentrated. The crude product was introduced to a silica gel loading column and purified by column chromatography (1-5% MeOH/DCM) to provide the desired product (796 mg, 1.26 mmol), 90%. MS (m/z) 632 $[M+H]^+$.

Synthesis of (S)-2-(2-(3-(2-amino-3-((4-methoxyphenyl)(methyl)amino)-3-oxopropyl)benzylthio)-1H-indol-3-yl)acetic acid To a solution of (S)-ethyl 2-(2-(3-(2-(tert-butoxycarbonylamino)-3-(4-methoxyphenyl)(methyl)amino)-3-oxopropyl)benzylthio)-1H-indol-3-yl)acetate (796 mg, 1.26 mmol) in 2 ml of tetrahydrofuran and 2 ml of methanol was added 4 ml of 2$\underline{N}$ LiOH. The reaction was heated at 60° C. for 2 hours. The cooled reaction was acidified with 1$\underline{N}$ (aq) HCl and then extracted with EtOAc (2×50 ml). The organic layer was dried over Na$_2$SO$_4$, filtered and concentrated. TFA (5 ml) was added to the crude product. After 20 minutes, the solvent was removed and the residue was dried under high vacuum. The crude product was dissolved in DMF and the solution was filtered and purified by RP HPLC using a C18 column and a gradient of 20% B to 80% B over 25 minutes (A=0.1% TFA/H$_2$O, B=0.1% TFA/acetonitrile) to provide the desired product (600 mg, 1.19 mmol). MS (m/z) 504 [M+H]$^+$.

Synthesis (9S)—N-(4-methoxyphenyl)-N-methyl-11-oxo-8,9,10,11,12,17-hexahydro-7,3-(metheno)[1,6]thiazacyclotetradecino[2,3-b]indole-9(2H)-carboxamide To a solution of (S)-2-(2-(3-(2-amino-3-((4-methoxyphenyl)(methyl)amino)-3-oxopropyl)benzylthio)-1H-indol-3-yl)acetic acid (600 mg, 1.19 mmol) and DIPEA (1.9 ml, 11.2 mmol) in DMF (390 ml) was added diphenylphosphoryl azide (1.58 mg, 5.95 mmol) in 7 ml of DMF dropwise. The reaction was stirred overnight, then 2 ml of acetic acid and 10 ml of methanol were added to quench the reaction. The solvent was removed in vacuo and the residue was dissolved in EtOAc (200 ml). The solution was washed with brine. The organic layer was dried over Na$_2$SO$_4$, filtered and concentrated. The crude product was introduced to a silica gel loading column and purified by column chromatography (1-5% MeOH/DCM). The product was dissolved in DMF and the solution was filtered and purified by RP HPLC using a C18 column and a gradient of 20% B to 80% B over 25 minutes (A=0.1% TFA/H$_2$O, B=0.1% TFA/acetonitrile). The yield was 380 mg of the TFA salt. MS (m/z) 486 [M+H]$^+$.

Synthesis of (9S)—N-(4-methoxyphenyl)-N-methyl-11-oxo-8,9,10,11,12,17-hexahydro-7,3-(metheno)[1,6]thiazacyclotetradecino[2,3-b]indole-9(2H)-carboxamide 1,1-dioxide To a solution (9S)—N-(4-methoxyphenyl)-N-methyl-11-oxo-8,9,10,11,12,17-hexahydro-7,3-(metheno)[1,6]thiazacyclotetradecino[2,3-b]indole-9(2H)-carboxamide (80 mg, 0.17 mmol) in DCM (5 ml) was added meta-chloroperoxybenzoic acid (74 mg, 77%, 0.34 mmol). The reaction was stirred for 2 hours and then diluted with DCM (20 ml). The organic layer was washed with NaHCO$_3$ (aq) and brine. The organic layer was dried over Na$_2$SO$_4$, filtered and concentrated. The crude product was dissolved in DMF and the solution was filtered and purified by RP HPLC using a C18 column and a gradient of 20% B to 80% B over 25 minutes (A=0.1% TFA/H$_2$O, B=0.1% TFA/acetonitrile). The yield was 40 mg of the TFA salt. MS (m/z) 518 [M+H]$^+$.

| Example | Structure | Exact Mass | Observed Mass M + 1 | Retention time (min) |
| --- | --- | --- | --- | --- |
| Example 20 | 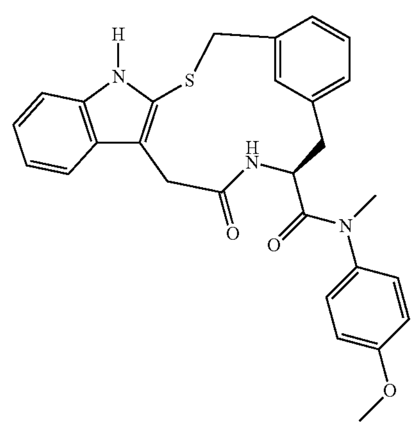 [SMILES: COc1ccc(N(C)C(=O)[C@@H]2Cc3cccc(c3)CSc3[nH]c4ccccc4c3CC(=O)N2)cc1] | 485 | 486 | 1.42 |
| Example 21 | 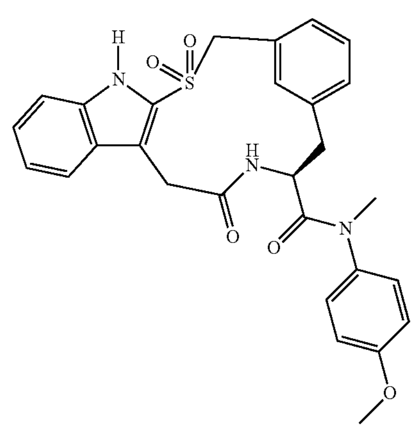 [SMILES: COc1ccc(N(C)C(=O)[C@@H]2Cc3cccc(c3)CS(=O)(=O)c3[nH]c4ccccc4c3CC(=O)N2)cc1] | 517 | 518 | 1.23 |

Example 22

Preparation of Compound 22

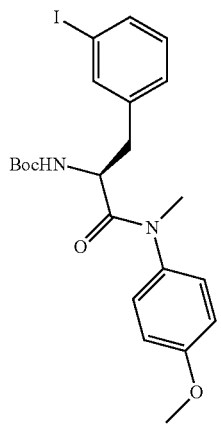

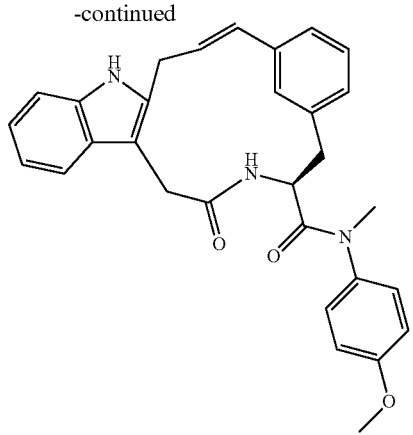

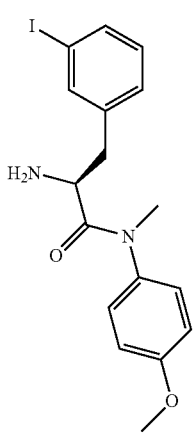 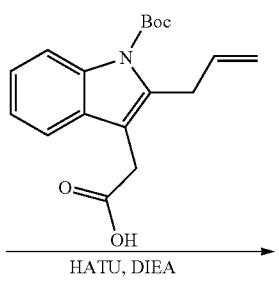

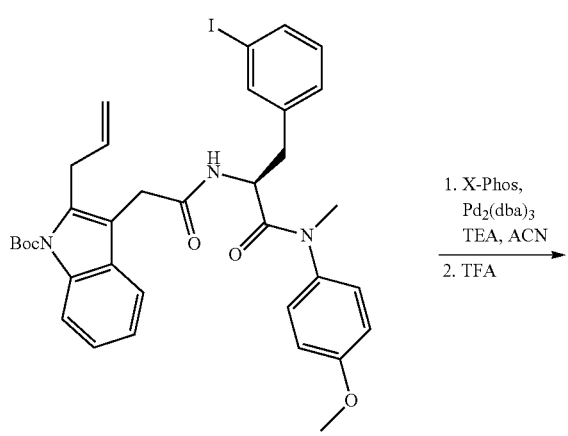

Synthesis of (5)-tert-butyl 2-allyl-3-(2-(3-(3-iodophenyl)-1-((4-methoxyphenyl)(methyl)amino)-1-oxopropan-2-ylamino)-2-oxoethyl)-1H-indole-1-carboxylate A solution of (S)-tert-butyl 3-(3-iodophenyl)-1-((4-methoxyphenyl)(methyl)amino)-1-oxopropan-2-ylcarbamate (556 mg, 1.09 mml) in TFA (3 ml) was stirred for 10 minutes. The solvent was removed in vacuo. 2-(2-allyl-1-(tert-butoxycarbonyl)-1H-indol-3-yl)acetic acid (343 mg, 1.09 mmol), DIEA (0.38 ml, 2.18 mmol) and O-(7-Azabenzotriazol-1-yl)-N,N,N',N'-tetramethyluronium hexafluorophosphate (HATU, 414.4 mg, 1.09 mmol) were dissolved in DMF. After 10 minutes, the solution was added to TFA salt. The reaction was stirred for 2 hours at room temperature. The mixture was diluted with EtOAc (100 ml) and washed with brine (2×50 ml). The organic layer was dried over $Na_2SO_4$, filtered and concentrated. The oily crude product was introduced to a silica gel loading column and purified by column chromatography (20-50% EtOAc/hexanes) to provide the desired product (620 mg, 0.94 mmol. MS (m/z) 660 $[M+H]^+$.

Synthesis of (4S,11E)-N-(4-methoxyphenyl)-N-methyl-2-oxo-2,3,4,5,13,14-hexahydro-1H-6,10-(metheno)azacyclopentadecino[5,4-b]indole-4-carboxamide A solution of (5)-tert-butyl 2-allyl-3-(2-(3-(3-iodophenyl)-1-((4-methoxyphenyl)(methyl)amino)-1-oxopropan-2-ylamino)-2-oxoethyl)-1H-indole-1-carboxylate (620 mg, 0.94 mmol), $Pd_2(dba)_3$ in TEA (6 ml) and ACN (42 ml) was heated at reflux overnight. The reaction was cooled to room temperature and filtered through celite. The filtrate was concentrated and the crude product was introduced to a silica gel loading column and purified by column chromatography (20-40% EtOAc/hexanes) to provide the desired product (313 mg). The product was dissolved in TFA (2 ml). After stirring 10 minutes, the solvent was removed. The crude product was dissolved in DMF and the solution was filtered and purified by RP HPLC using a C18 column and a gradient of 20% B to 80% B over 25 minutes (A=0.1% TFA/H$_2$O, B=0.1% TFA/acetonitrile). The yield was 61 mg of the TFA salt. MS (m/z) 480 [M+H]$^+$.
Example 23
Preparation of Compound 23
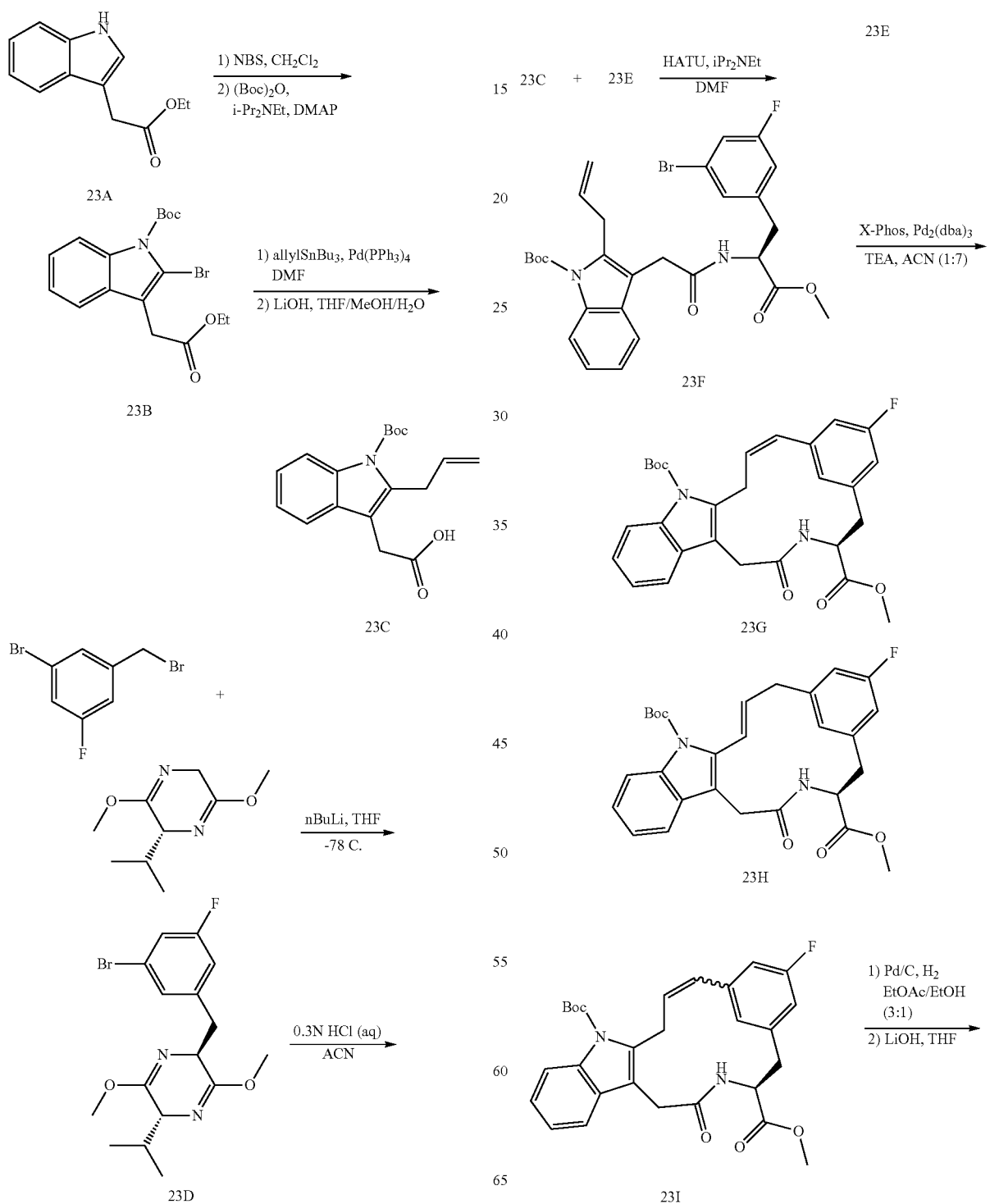

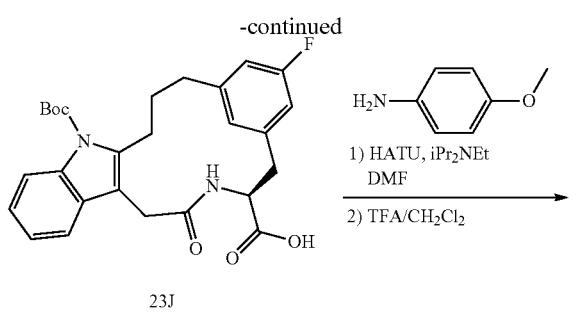

Preparation of tert-butyl 2-bromo-3-(2-ethoxy-2-oxoethyl)-1H-indole-1-carboxylate Ethyl 2-(1H-indol-3-yl)acetate (15 g, 73.9 mmol) was dissolved in DCM (750 mL). At ambient temperature, NBS (13.15 g, 73.9 mmol) was added to the reaction mixture in 5 portions approximately 2 minutes apart. After the last addition of NBS, iPr$_2$NEt (28 mL, 162 mmol) was added slowly to the reaction mixture and stirred for 5 minutes. Boc$_2$O (33.8 g, 155 mmol) was added followed by DMAP (900 mg). After stirring at 16 h, the reaction was partitioned between DCM and H$_2$O. The organics were washed with aqueous 1N HCl and dried over sodium sulfate. After removal of solvent, the crude product was purified by silica gel chromatography to provide tert-butyl 2-bromo-3-(2-ethoxy-2-oxoethyl)-1H-indole-1-carboxylate (16.3 g, 58%). MS (m/z) 382 [M+H]$^+$.

Preparation of tert-butyl 2-allyl-3-(2-methoxy-2-oxoethyl)-1H-indole-1-carboxylate Argon was bubbled into a solution of tert-butyl 2-bromo-3-(2-ethoxy-2-oxoethyl)-1H-indole-1-carboxylate (3.68 g, 9.66 mmol) in DMF (50 mL) for 1 h. Allyltributyltin (3 mL, 9.66 mmol) was added to the reaction mixture followed by the addition of Pd(PPh$_3$)$_4$ (1.1 g, 10 mol %). The reaction was heated at 80° C. for 6 h and then diluted with EtOAc and H$_2$O. The entire solution was filtered over celite and to the solute was added 20% aqueous KH$_2$PO$_4$. The organics were separated and dried over sodium sulfate. After removal of solvent, the crude product was purified by silica gel chromatography to provide tert-butyl 2-allyl-3-(2-methoxy-2-oxoethyl)-1H-indole-1-carboxylate (2.52 g, 76%). MS (m/z) 330 [M+H]$^+$.

Preparation of 2-(2-allyl-1-(tert-butoxycarbonyl)-1H-indol-3-yl)acetic acid

To a solution of tert-butyl 2-allyl-3-(2-methoxy-2-oxoethyl)-1H-indole-1-carboxylate (0.94 g, 2.74 mmol) in THF (15 mL) and MeOH (5 mL) was added a solution of LiOH (170 mg, 6.8 mmol) in H$_2$O (5 mL). The solution was stirred for 2 h. The reaction was partitioned between EtOAc and 20% aqueous KH$_2$PO$_4$. The organics were separated, dried over sodium sulfate, and the solvents removed in vacuo to provide 2-(2-allyl-1-(tert-butoxycarbonyl)-1H-indol-3-yl)acetic acid (900 mg). MS (m/z) 316 [M+H]$^+$.

Preparation of (2S,5R)-2-(3-bromo-5-fluorobenzyl)-5-isopropyl-3,6-dimethoxy-2,5-dihydropyrazine To (R)-2,5-dihydro-3,6-dimethoxy-2-isopropylpyrazine (2 mL, 11.03 mmol) in THF (90 mL) at −78° C. was added n-BuLi (1.6 M in hexanes solution, 7.5 mL, 12 mmol). After stirring for 30 min, 1-bromo-3-(bromomethyl)-5-fluorobenzene (2.68 g, 10 mmol) in THF (10 mL) was added dropwise over 30 min. The temperature was maintained at −78° C. for 30 min then allowed to warm to ambient temperature. After stirring for 16 h, saturated aqueous NH$_4$Cl (30 mL) was added followed by dilution with EtOAc and H$_2$O. The THF was removed in vacuo and the remaining organics were separated and dried over sodium sulfate. After removal of solvent, the crude product was purified by silica gel chromatography to provide (2S,5R)-2-(3-bromo-5-fluorobenzyl)-5-isopropyl-3,6-dimethoxy-2,5-dihydropyrazine (3.17 g, 77%). MS (m/z) 371 [M+H]$^+$.

Preparation of (S)-methyl 2-amino-3-(3-bromo-5-fluorophenyl)propanoate hydrochloride A stirred solution of (2S,5R)-2-(3-bromo-5-fluorobenzyl)-5-isopropyl-3,6-dimethoxy-2,5-dihydropyrazine (1.21 g, 3.27 mmol) in acetonitrile (15 mL) was treated with 0.3 N aqueous HCl (15 mL). The reaction was stirred for 2 h and then neutralized with the addition of 1N aq. NaOH. The acetonitrile was removed in vacuo and the solution was extracted with EtOAc. The organics were combined, dried over sodium sulfate, and removed in vacuo to provide (S)-methyl 2-amino-3-(3-bromo-5-fluorophenyl)propanoate hydrochloride (720 mg, 70%). MS (m/z) 276 [M+H]$^+$.

Preparation of (S)-tert-butyl 2-allyl-3-(2-(3-(3-bromo-5-fluorophenyl)-1-methoxy-1-oxopropan-2-ylamino)-2-oxoethyl)-1H-indole-1-carboxylate 2-(2-allyl-1-(tert-butoxycarbonyl)-1H-indol-3-yl)acetic acid (850 mg, 2.7 mmol) and (S)-methyl 2-amino-3-(3-bromo-5-fluorophenyl)propanoate hydrochloride (720 mg, 2.61 mmol) were combined in DCM (13 mL) and treated with HATU (1.49 g, 3.9 mmol) and iPr$_2$NEt (1.13 mL, 6.5 mmol). After stirring for 16 h at room temperature, the reaction was partitioned between DCM and H$_2$O. The organics were separated and dried over sodium sulfate. After removal of solvent, the crude product was purified by silica gel chromatography to provide (S)-tert-butyl 2-allyl-3-(2-(3-(3-bromo-5-fluorophenyl)-1-methoxy-1-oxopropan-2-ylamino)-2-oxoethyl)-1H-indole-1-carboxylate (0.98 g, 63%). MS (m/z) 573 [M+H]$^+$.

Preparation of 23G, 23H, 23I

Argon was bubbled into a solution of (S)-tert-butyl 2-allyl-3-(2-(3-(3-bromo-5-fluorophenyl)-1-methoxy-1-oxopropan-2-ylamino)-2-oxoethyl)-1H-indole-1-carboxylate in acetonitrile (350 mL) and TEA (50 mL) for 30 min. X-Phos (82 mg, 15 mol %) and Pd(PPh$_3$)$_4$ (52 mg, 5 mol %) were added and the reaction mixture was heated to reflux for 3 h.

Due to a lack of progression, the reaction was cooled to ambient temperature, filtered over celite, and argon was bubbled through the resultant solute. X-Phos (41 mg) and Pd$_2$(dba)$_3$ (26 mg) were added to the reaction and again heated to reflux for 3 h. After cooling to ambient temperature, the reaction was filtered over celite and solvents removed in vacuo. The resultant crude was partitioned between EtOAc and H$_2$O. The organics were separated, washed with 0.5N aqueous HCL and dried over sodium sulfate. After removal of solvents, the crude product was purified by silica gel chromatography to provide two mixtures of olefin isomers. Mixture A contained 14-tert-butyl 4-methyl (4S,11Z)-8-fluoro-2-oxo-1,2,3,4,5,13-hexahydro-14H-6,10-(metheno)azacyclopentadecino[5,4-b]indole-4,14-dicarboxylate (23G) and 14-tert-butyl 4-methyl (4S,12E)-8-fluoro-2-oxo-1,2,3,4,5,11-hexahydro-14H-6,10-(metheno)azacyclopentadecino[5,4-b]indole-4,14-dicarboxylate (23H) (45 mg, ratio ~5:1); MS (m/z) 493 [M+H]$^+$. Mixture B contained a complex mixture of olefin isomers (375 mg); MS (m/z) 493 [M+H]$^+$.

Preparation of (4S)-14-(tert-butoxycarbonyl)-8-fluoro-2-oxo-2,3,4,5,11,12,13,14-octahydro-1H-6,10-(metheno)azacyclopentadecino[5,4-b]indole-4-carboxylic acid Mixture B (375 mg, 0.76 mmol) from the previous step was dissolved in EtOAc (8 mL) and EtOH (1 mL) and treated with Pd/C (40 mg). The reaction was placed under an atmosphere of H$_2$ and stirred for 6 h. The reaction was filtered over celite and the solvents removed in vacuo. The residue was dissolved in THF (4.2 mL) and MeOH (1.4 mL) and treated with a solution of LiOH (44 mg, 1.8 mmol) in H$_2$O (1.4 mL). After stirring for 3 h at ambient temperature, the reaction was treated with 20% aqueous KH$_2$PO$_4$ and extracted with EtOAc. The combined organics were washed with brine, dried over sodium sulfate, and the solvents were removed in vacuo to provide (4S)-14-(tert-butoxycarbonyl)-8-fluoro-2-oxo-2,3,4,5,11,12,13,14-octahydro-1H-6,10-(metheno)azacyclopentadecino[5,4-b]indole-4-carboxylic acid. MS (m/z) 481 [M+H]$^+$.

Preparation of (4S)-8-fluoro-N-(4-methoxyphenyl)-N-methyl-2-oxo-2,3,4,5,11,12,13,14-octahydro-1H-6,10-(metheno)azacyclopentadecino[5,4-b]indole-4-carboxamide To a solution of (4S)-14-(tert-butoxycarbonyl)-8-fluoro-2-oxo-2,3,4,5,11,12,13,14-octahydro-1H-6,10-(metheno)azacyclopentadecino[5,4-b]indole-4-carboxylic acid (29 mg, 0.06 mmol), 4-methoxy-N-methylaniline (9 mg, 0.07 mmol), and HATU (28 mg, 0.072 mmol) in DMF (0.6 mL) was added iPr$_2$NEt (0.016 mL). After stirring at ambient temperature for 16 h, the reaction was partitioned between EtOAc and H$_2$O. The organics were washed with brine and dried over sodium sulfate. After removal of solvent, the crude product was purified by silica gel chromatography. The resultant product was dissolved in DCM (1 mL) and treated with TFA (0.5 mL). After 30 min, the solvent was removed in vacuo and the crude product purified by RP HPLC to provide (4S)-8-fluoro-N-(4-methoxyphenyl)-N-methyl-2-oxo-2,3,4,5,11,12,13,14-octahydro-1H-6,10-(metheno)azacyclopentadecino[5,4-b]indole-4-carboxamide: 1H NMR: CD3OD δ 7.48 (dd, 1H), 7.32 (d, 2H), 7.29 (dd, 1H), 7.04 (d, 2H), 7.00 (m, 2H), 6.73 (d, 1H), 6.26 (d, 1H), 6.25 (s, 1H), 4.74 (dd, 1H), 3.82 (s, 3H), 3.52 (d, 1H), 3.36 (d, 1H), 3.24 (s, 3H), 2.80 (dd, 1H), 2.69 (dd, 2H), 2.58 (dd, 1H), 2.51 (m, 1H), 2.31 (m, 1H), 2.25 (m, 1H), 2.02 (m, 1H); MS (m/z) 500 [M+H]$^+$ Example 24

Preparation of Compound 24

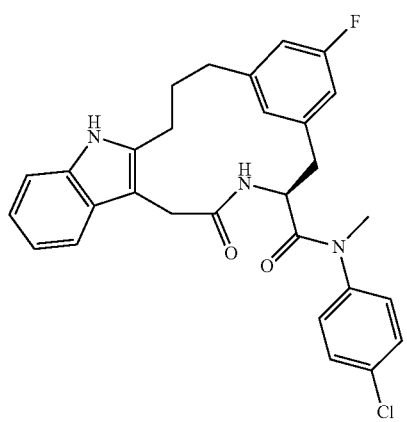 [SMILES: CN(C(=O)[C@@H]1Cc2cc(F)cc(c2)CCCc2[nH]c3ccccc3c2CC(=O)N1)c1ccc(Cl)cc1]

Compound 24 was prepared according to the method presented in the final step for the synthesis of Example 23 substituting 4-chloro-N-methylaniline for 4-methoxy-N-methylaniline to provide (4S)—N-(4-chlorophenyl)-8-fluoro-N-methyl-2-oxo-2,3,4,5,11,12,13,14-octahydro-1H-6,10-(metheno)azacyclopentadecino[5,4-b]indole-4-carboxamide: 1H NMR: CD3OD δ 7.44 (d, 2H), 7.39 (dd, 1H), 7.26 (d, 1H), 7.21 (dd, 2H), 6.93 (m, 2H), 6.67 (d, 1H), 6.26 (d, 1H), 6.19 (s, 1H), 4.64 (dd, 1H), 3.42 (d, 1H), 3.28 (d, 1H), 3.19 (s, 3H), 2.73 (dd, 1H), 2.62 (dd, 2H), 2.56 (m, 1H), 2.41 (m, 1H), 2.25 (m, 1H), 2.16 (m, 1H), 1.95 (m, 1H); MS (m/z) 504 [M+H]$^+$ Example 25

Preparation of Compound 25

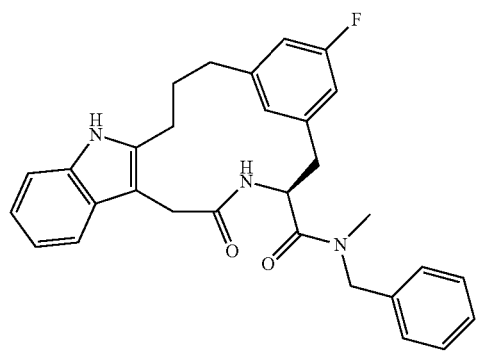 [SMILES: CN(Cc1ccccc1)C(=O)[C@@H]1Cc2cc(F)cc(c2)CCCc2[nH]c3ccccc3c2CC(=O)N1]

Compound 25 was prepared according to the method presented in the final step for the synthesis of Example 23 substituting N-benzylmethylamine for 4-methoxy-N-methylaniline to provide (4S)—N-benzyl-8-fluoro-N-methyl-2-oxo- 2,3,4,5,11,12,13,14-octahydro-1H-6,10-(metheno) azacyclopentadecino[5,4-b]indole-4-carboxamide: MS (m/z) 484 [M+H]+

Examples 26-27

Preparation of Compounds 26-27

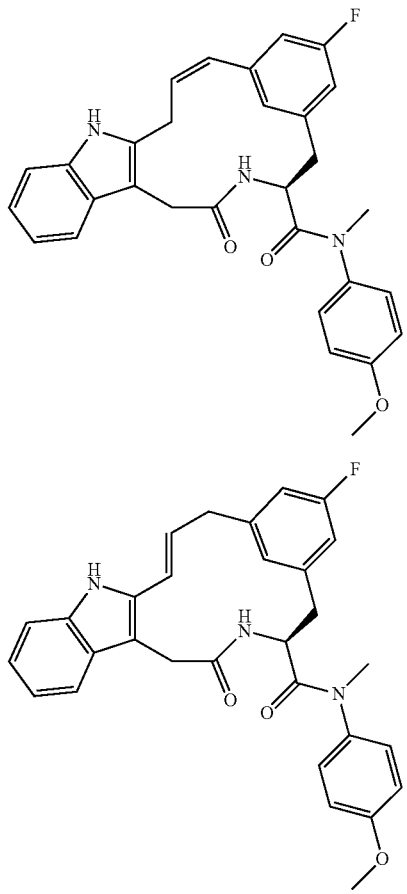

Example 26 and Example 27 were prepared according to the method presented for the synthesis of Example 23 utilizing Mixture A of 23G and 23H and omitting the Pd/C. Purification of the final step provided two products.

Compound 26: (4S,11Z)-8-fluoro-N-(4-methoxyphenyl)-N-methyl-2-oxo-2,3,4,5,13,14-hexahydro-1H-6,10-(metheno)azacyclopentadecino[5,4-b]indole-4-carboxamide 1H NMR: CD3OD δ 7.33 (d, 2H), 7.29 (d, 2H), 7.18 (d, 2H), 7.03 (d, 2H), 6.99 (m, xH), 6.94 (m, xH), 6.87 (m, xH), 6.40 (m, 1H), 5.46 (s, 1H), 5.39 (bs, 1H), 4.66 (m, 1H), 3.95 (m, 1H), 3.84 (m, 1H), 3.82 (s, 3H), 3.73 (d, 1H), 3.60 (d, 1H), 3.16 (m, 3H), 2.81 (dd, 1H), 2.56 (m, 1H). MS (m/z) 498 [M+H]+

Compound 27: (4S,12E)-8-fluoro-N-(4-methoxyphenyl)-N-methyl-2-oxo-2,3,4,5,11,14-hexahydro-1H-6,10-(metheno)azacyclopentadecino[5,4-b]indole-4-carboxamide 1H NMR: CD3OD δ 7.42 (dd, 1H), 7.37 (d, 2H), 7.21 (dd, 1H), 7.00 (m, 1H), 6.99 (d, 2H), 6.72 (m, 1H), 6.40 (m, 1H), 6.22 (m, 1H), 6.08 (m, 1H), 4.87 (m, 1H, obscured by solvent), 3.80 (s, 3H), 3.65 (m, 1H), 3.56 (m, 1H), 3.46 (m, 2H), 3.01 (m, 1H), 2.86 (m, 1H). MS (m/z) 498 [M+H]+

Example 28

Preparation of Compound 28

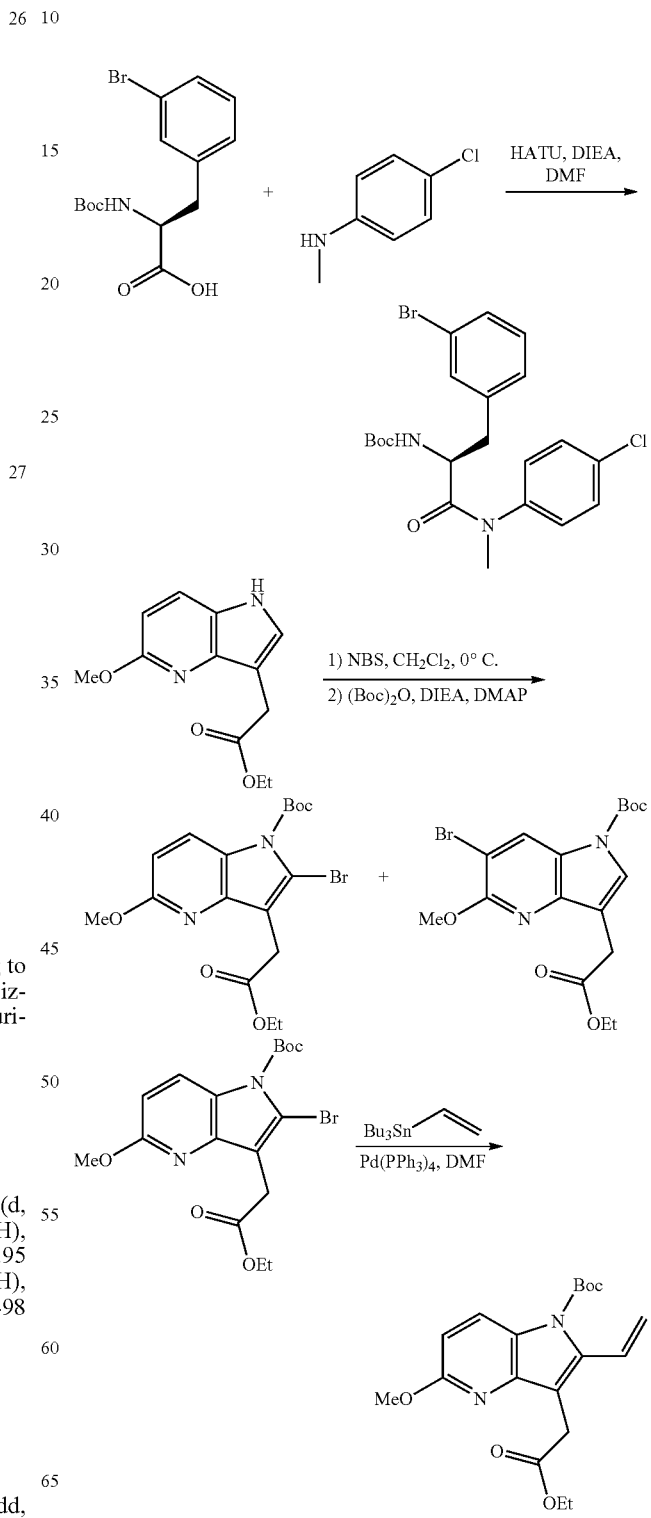

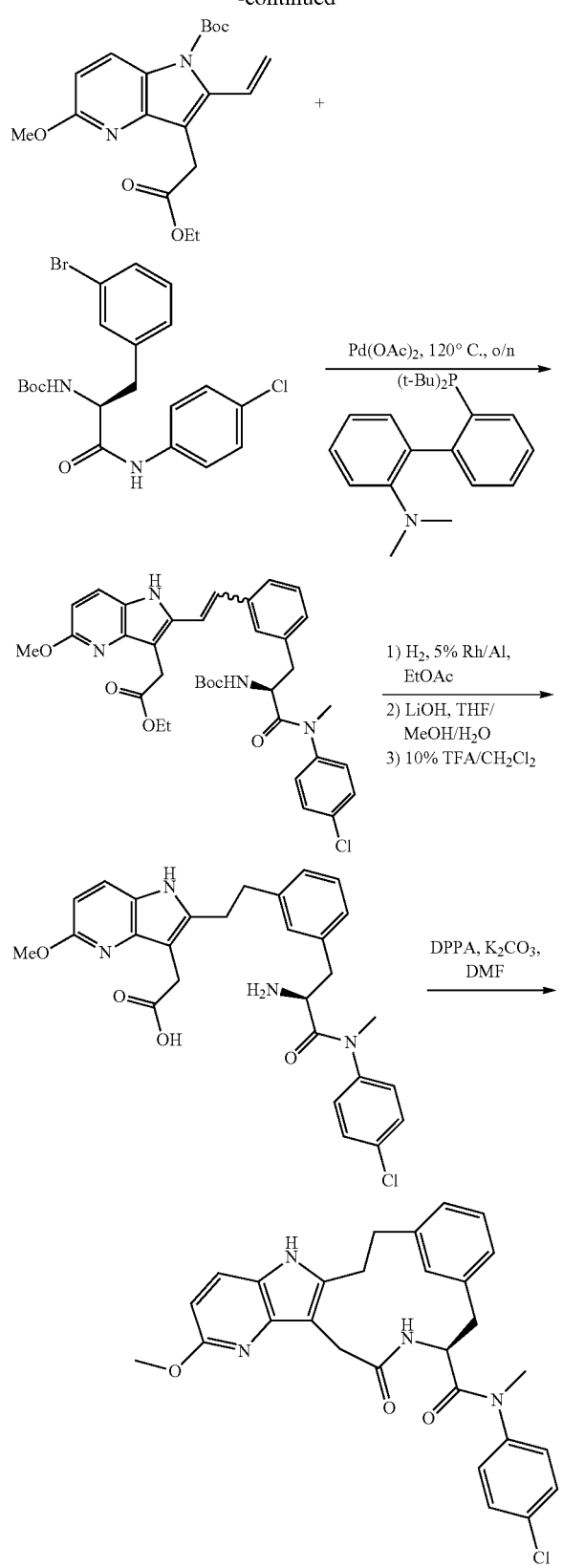

Preparation of (S)-tert-butyl 3-(3-bromophenyl)-1-((4-chlorophenyl)(methyl)amino)-1-oxopropan-2-ylcarbamate Boc-L-3-BromoPhe (5 g, 14.5 mmol) was dissolved in 50 mL of DMF and to it were added 4-chloro-N-methylaniline (2.1 mL, 17.4 mmol) and N,N-diisopropylethylamine (7.6 mL, 43.5 mmol). The reaction mixture was cooled to 0° C. and to it was added HATU portion wise (6.6 g, 17.4 mmol). The reaction mixture was allowed to stir at ambient temperature overnight and then was partitioned between ethyl acetate and water. The organic layer was separated and washed with 5% aqueous LiCl, saturated aqueous NaHCO$_3$ and brine. The mixture was then dried over MgSO$_4$, filtered and concentrated to afford crude product which was purified by silica gel chromatography eluting with ethyl acetate/hexanes to afford 5.6 g of (S)-tert-butyl 3-(3-bromophenyl)-1-((4-chlorophenyl)(methyl)amino)-1-oxopropan-2-ylcarbamate as a white solid. MS (m/z): 469.1 [M+H]$^+$; HPLC retention time 4.39 min (5-99% acetonitrile:water with 0.05% formic acid).

Preparation of tert-butyl 2-bromo-3-(2-ethoxy-2-oxoethyl)-5-methoxy-1H-pyrrolo[3,2-b]pyridine-1-carboxylate Ethyl 2-(5-methoxy-1H-pyrrolo[3,2-b]pyridin-3-yl)acetate (1.0 g, 4.26 mmol) was dissolved in methylene chloride (40 mL) and cooled to 0° C. with ice-water bath. NBS (760 mg, 4.26 mmol) was added in small portions over 1 hour. The reaction mixture was allowed to stir at 0° C. for two more hours. Then, to the reaction mixture were added N,N-diisopropylethylamine (1.86 mL, 8.52 mmol), di-tert-butyl carbonate (1.86 g, 8.52 mmol) and 4-dimethylaminopyridine (52 mg, 0.42 mmol). The resulting mixture was allowed to stir overnight at ambient temperature. More methylene chloride was added and washed with water and half-brine. The organic layer was separated and dried over MgSO$_4$. The mixture was filtered and the filtrate was concentrated to dryness, and the residue was purified by silica gel chromatography (loading with toluene, eluting with EtOAc/hexanes) then RP HPLC eluting with acetonitrile/water to afford 455 mg of tert-butyl 2-bromo-3-(2-ethoxy-2-oxoethyl)-5-methoxy-1H-pyrrolo[3,2-b]pyridine-1-carboxylate and 131 mg of side product. MS (m/z): 415.0 [M+H]+; HPLC retention time 4.68 min (5-99% acetonitrile:water with 0.05% formic acid).

Preparation of tert-butyl 3-(2-ethoxy-2-oxoethyl)-5-methoxy-2-vinyl-1H-pyrrolo[3,2-b]pyridine-1-carboxylate Under a nitrogen atmosphere, tert-butyl 2-bromo-3-(2-ethoxy-2-oxoethyl)-5-methoxy-1H-pyrrolo[3,2-b]pyridine-1-carboxylate (207 mg, 0.5 mmol), tributylvinyl tin (175 µL, 0.6 mmol) and tetrakis(triphenylphosphine)palladium(0) (29 mg, 0.025 mmol) were combined in 10 mL of DMF, and the mixture was heated to 85° C. overnight. The reaction was allowed to cool to ambient temperature and was partitioned between ethyl acetate and water. The organic layer was separated and washed with 5% aqueous LiCl and brine. The organic layer was then dried over MgSO$_4$, filtered and concentrated to afford crude product which was purified by RP HPLC eluting with acetonitrile and water to afford 120 mg of tert-butyl 3-(2-ethoxy-2-oxoethyl)-5-methoxy-2-vinyl-1H-pyrrolo[3,2-b]pyridine-1-carboxylate. MS (m/z): 361.2 [M+H]+; HPLC retention time 4.69 min (5-99% acetonitrile:water with 0.05% formic acid).

Preparation of (S)-ethyl 2-(2-(3-(2-(tert-butoxycar-bonylamino)-3-((4-chlorophenyl)(methyl)amino)-3-oxopropyl)styryl)-5-methoxy-1H-pyrrolo[3,2-b]pyridin-3-yl)acetate Under a nitrogen atmosphere, tert-butyl 3-(2-ethoxy-2-oxoethyl)-5-methoxy-2-vinyl-H-pyrrolo[3,2-b]pyridine-1-carboxylate (120 mg, 0.33 mmol), (S)-tert-butyl 3-(3-bromophenyl)-1-((4-chlorophenyl)(methyl)amino)-1-oxopropan-2-ylcarbamate (170 ma, 0.36 mmol), palladium acetate (7.4 mg, 0.033 mmol), 2-di-tert-butylphosphino-2'-(N,N-dimethylamino) biphenyl (22.5 mg, 0.066 mmol), triethylamine (368 µL, 2.6 mmol) and DMF (2 mL) were mixed in a microwave vessel which was sealed and purged with $N_2$. The vial was heated to 120° C. overnight. The reaction was allowed to cool to ambient temperature and was partitioned between ethyl acetate and water. The organic layer was separated and washed with 5% aqueous LiCl and brine. The organic layer was then dried over $MgSO_4$, filtered and concentrated to afford crude product which was purified by silica gel chromatography eluting with ethyl acetate and hexanes to afford 170 mg of (S)-ethyl 2-(2-(3-(2-(tert-butoxycarbonylamino)-3-((4-chlorophenyl)(methyl)amino)-3-oxopropyl)styryl)-5-methoxy-1H-pyrrolo[3,2-b]pyridin-3-yl)acetate. MS (m/z): 647.1 [M+H]+; HPLC retention time 4.38 min (5-99% acetonitrile:water with 0.05% formic acid).

Preparation of (S)-2-(2-(3-(2-amino-3-((4-chlorophenyl)(methyl)amino)-3-oxopropyl)phenethyl)-5-methoxy-1H-pyrrolo[3,2-b]pyridin-3-yl)acetic acid (S)-ethyl 2-(2-(3-(2-(tert-butoxycarbonylamino)-3-((4-chlorophenyl)(methyl)amino)-3-oxopropyl)styryl)-5-methoxy-1H-pyrrolo[3,2-b]pyridin-3-yl)acetate (170 mg, 0.26 mmol) was dissolved in 50 mL of ethyl acetate and purged with nitrogen. Rhodium (5 wt. % on alumina powder, 60 mg) was added. The reaction mixture was purged with hydrogen and stirred at ambient temperature overnight under a hydrogen balloon. After completion of the reaction, the mixture was filtered, rinsing with ethyl acetate. The filtrate was concentrated to afford (S)-ethyl 2-(2-(3-(2-(tert-butoxycarbonylamino)-3-((4-chlorophenyl)(methyl)amino)-3-oxopropyl)phenethyl)-5-methoxy-1H-pyrrolo[3,2-b]pyridin-3-yl)acetate which was dissolved in 5 mL of THF/MeOH/$H_2O$ (3/2/1), and to it was added LiOH.$H_2O$ (55 mg). The reaction mixture was allowed to stir at ambient temperature for two hours and then purified by RP HPLC eluting with acetonitrile/water (with 0.1% TFA) to afford (S)-2-(2-(3-(2-(tert-butoxycarbonylamino)-3-((4-chlorophenyl)(methyl)amino)-3-oxopropyl)phenethyl)-5-methoxy-1H-pyrrolo[3,2-b]pyridin-3-yl)acetic acid. The compound was dissolved in 3 mL of 10% TFA/$CH_2Cl_2$ and stirred at ambient temperature for two hours. The reaction was cooled down to 0° C. and quenched with 0.3 mL of pyridine. The solvent was removed and the residue was purified by RP HPLC eluting with acetonitrile and water to afford 106 mg of (S)-2-(2-(3-(2-amino-3-((4-chlorophenyl)(methyl)amino)-3-oxopropyl)phenethyl)-5-methoxy-1H-pyrrolo[3,2-b]pyridin-3-yl)acetic acid. MS (m/z): 521.3 [M+H]+; HPLC retention time 2.05 min (5-99% acetonitrile:water with 0.05% formic acid).

Preparation of (14S)—N-(4-chlorophenyl)-2-methoxy-N-methyl-16-oxo-5,6,7,13,14,15,16,17-octahydro-12,8-(metheno)pyrido[2',3':4,5]pyrrolo[3,2-d]azacyclotetradecine-14-carboxamide (S)-2-(2-(3-(2-amino-3-((4-chlorophenyl)(methyl)amino)-3-oxopropyl)phenethyl)-5-methoxy-1H-pyrrolo[3,2-b]pyridin-3-yl)acetic acid (106 mg, 0.2 mmol) was dissolved in 100 mL of DMF and to it were added diphenylphosphoryl azide (112 mg, 0.4 mmol) and sodium bicarbonate (50 mg, 0.6 mmol). The reaction mixture was allowed to stir at ambient temperature for one day. The solvent was removed and the residue was purified by RP HPLC eluting with acetonitrile and water (with 0.1% TFA) to afford 19 mg of (14S)—N-(4-chlorophenyl)-2-methoxy-N-methyl-16-oxo-5,6,7,13,14,15,16,17-octahydro-12,8-(metheno)pyrido[2',3':4,5]pyrrolo[3,2-d]azacyclotetradecine-14-carboxamide. $^1$H NMR (400 MHz, $CD_3OD$, ppm) δ 7.64 (d, J=8.6 Hz, 1H), 7.54 (d, J=8.4 Hz, 2H), 7.39 (d, J=8.4 Hz, 2H), 7.05-6.81 (m, 3H), 6.59 (d, J=8.7 Hz, 1H), 6.44 (d, J=6.9 Hz, 1H), 4.55 (m, 1H), 4.03 (s, 3H), 3.74 (d, J=16.1 Hz, 1H), 3.15 (s, 3H), 3.12 (m, 1H), 2.95 (m, 4H), 2.81-2.61 (m, 2H). MS (m/z): 503.2 [M+H]+; HPLC retention time 2.73 min (5-99% acetonitrile:water with 0.05% formic acid).

Example 29

Preparation of Compound 29

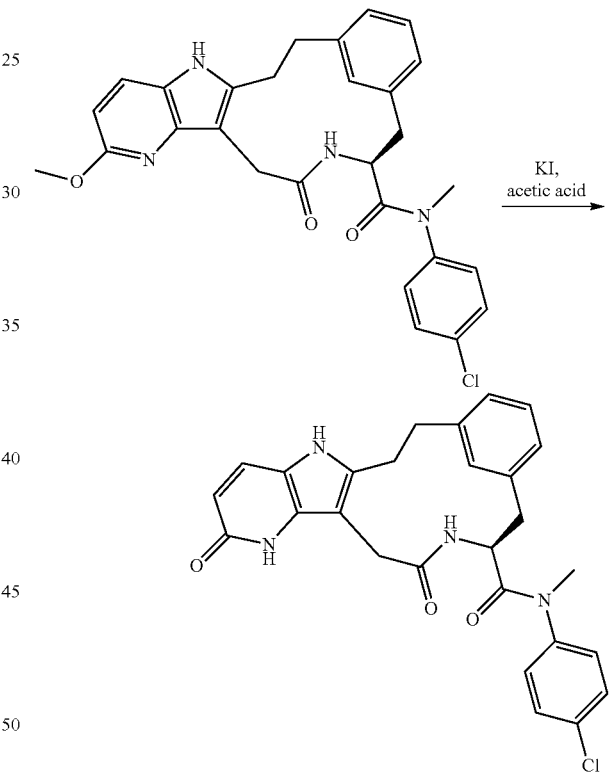

29

Preparation of (14S)—N-(4-chlorophenyl)-N-methyl-2,16-dioxo-1,2,5,6,7,13,14,15,16,17-decahydro-12,8-(metheno)pyrido[2',3':4,5]pyrrolo[3,2-d]azacyclotetradecine-14-carboxamide (14S)—N-(4-chlorophenyl)-2-methoxy-N-methyl-16-oxo-5,6,7,13,14,15,16,17-octahydro-12,8-(metheno)pyrido[2',3':4,5]pyrrolo[3,2-d]azacyclotetradecine-14-carboxamide (19 mg, 0.037 mmol) was dissolved in 1 mL of acetic acid, and to it was added KI (24 mg, 0.148 mmol). The reaction mixture was heated at 100° C. for two hours and then cooled to ambient temperature. The solvent was removed and the residue was purified by RP HPLC eluting with acetonitrile and water (with 0.1% TFA) to afford 1.3 mg of (14S)—N-(4-chlorophenyl)-N-methyl-2,16-dioxo-1,2,5,6,7,13,14,15,16,17-decahydro-12,8-(metheno)pyrido[2',3':4,5]pyrrolo[3,2-d]azacyclotetradecine-14-carboxamide and recovered 3.2 mg of starting material. $^1$H NMR (400 MHz, CD$_3$OD, ppm) δ 7.53 (m, 3H), 7.38 (d, J=8.3 Hz, 2H), 6.99 (s, 1H), 6.76 (m, 1H), 6.65 (m, 1H), 6.36 (d, J=7.1 Hz, 1H), 6.13 (d, J=9.2 Hz, 1H), 4.55 (m, 1H), 3.46 (d, J=15.5 Hz, 1H), 3.25 (s, 3H), 3.16 (m, 2H), 3.02-2.75 (m, 3H), 2.57 (t, J=11.9 Hz, 1H). MS (m/z): 488.9 [M+H]+; HPLC retention time 2.81 min (5-99% acetonitrile:water with 0.05% formic acid).

Example 30

Preparation of Compound 30

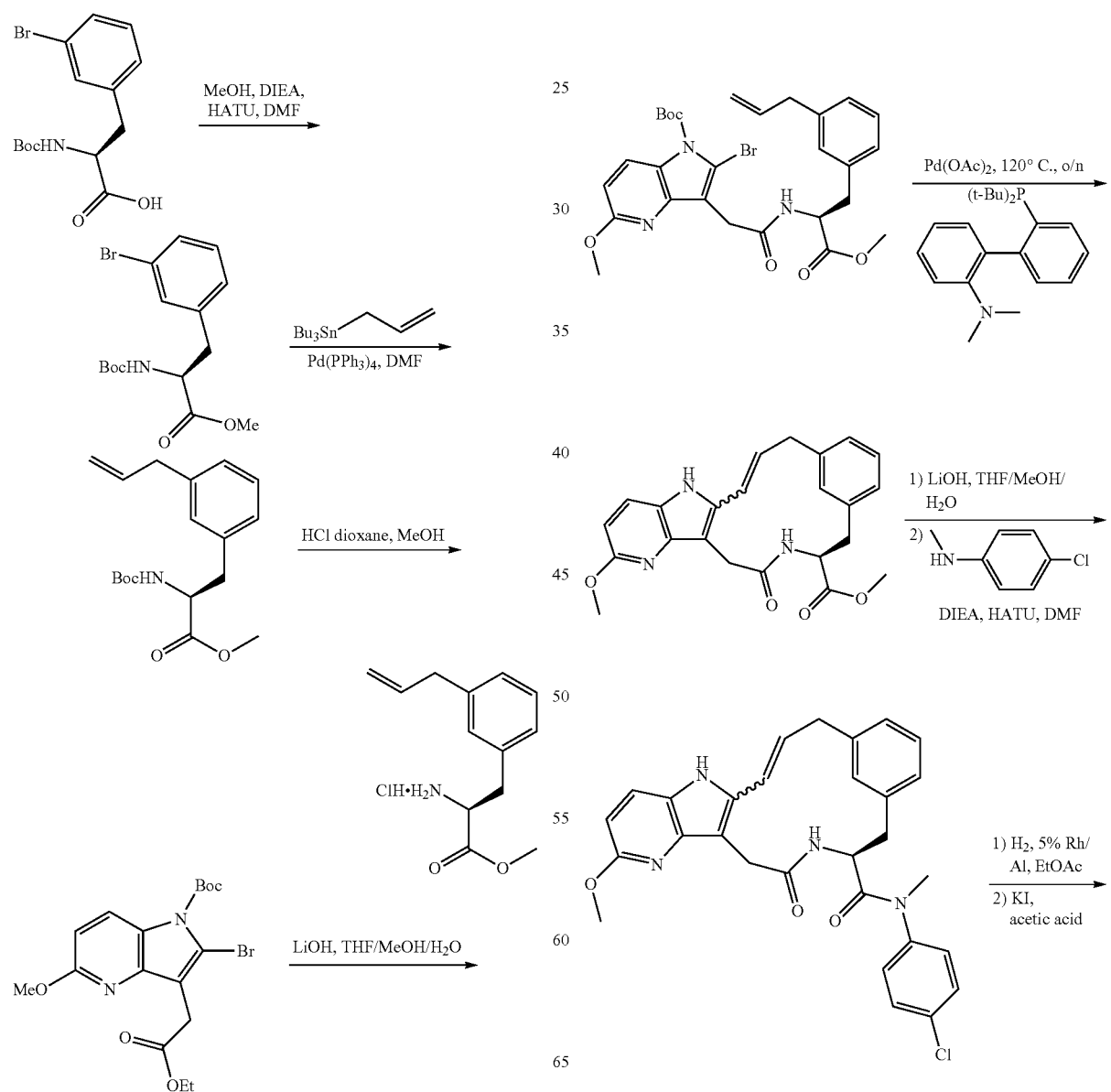

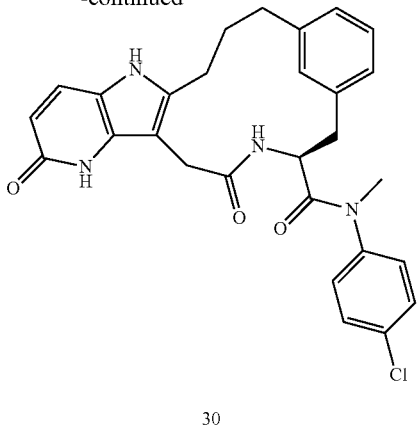

Preparation of (S)-methyl 3-(3-allylphenyl)-2-aminopropanoate hydrochloride

Boc-L-3-BromoPhe (5 g, 14.5 mmol) was dissolved in 30 mL of DMF and to it were added methanol (1 mL) and N,N-diisopropylethylamine (6.3 mL, 36.3 mmol). The reaction mixture was cooled down to 0° C. and to it was added HATU portionwise (6.6 g, 17.4 mmol). The reaction mixture was allowed to stir at ambient temperature overnight and then was partitioned between ethyl acetate and water. The organic layer was separated and washed with 5% aqueous LiCl, saturated aqueous NaHCO$_3$ and brine. It was then dried over MgSO$_4$, filtered and concentrated to afford crude product which was purified by silica gel chromatography eluting with ethyl acetate/hexanes to afford 4.9 g of Boc-L-3-BromoPhe-OMe.

2 g of the above Boc-L-3-BromoPhe-OMe (5.58 mmol) was dissolved in 60 mL of DMF. The system was degassed and purged with nitrogen. Allyltributylstannane (2.6 mL, 8.37 mmol) and tetrakis(triphenylphosphine)palladium(0) (19 mg, 0.017 mmol) were added and the mixture was stirred at 120° C. for one day. The solvent was removed and the residue was dissolved in ethyl ether, to it was added water (150 µL, 8.37 mmol) and DBU (1.25 mL, 8.37 mmol). The mixture was stirred at ambient temperature for two hours and the resulting precipitate was filtered off. The filtrate was concentrated and purified by silica gel chromatography eluting with ethyl acetate/hexanes to afford 906 mg of Boc-L-3-allylPhe-OMe.

Boc-L-3-allylPhe-OMe (770 mg, 2.4 mmol) was dissolved in 5 mL of methanol and to it was added 4N HCl in 1,4-dioxane (2.4 mL). The mixture was stirred at ambient temperature for 3 hours. The solvent was removed to afford (S)-methyl 3-(3-allylphenyl)-2-aminopropanoate hydrochloride. MS (m/z): 220.2 [M+H]+; HPLC retention time 1.72 min (5-99% acetonitrile:water with 0.05% formic acid).

Preparation of (S)-tert-butyl 3-(2-(3-(3-allylphenyl)-1-methoxy-1-oxopropan-2-ylamino)-2-oxoethyl)-2-bromo-5-methoxy-1H-pyrrolo[3,2-b]pyridine-1-carboxylate tert-Butyl 2-bromo-3-(2-ethoxy-2-oxoethyl)-5-methoxy-1H-pyrrolo[3,2-b]pyridine-1-carboxylate (380 mg, 0.9 mmol) was dissolved in 12 mL of THF/MeOH/H$_2$O (3/2/1) and to it was added LiOH.H$_2$O (116 mg, 2.7 mmol). The reaction mixture was allowed to stir at ambient temperature for 3 hours and then purified by RP HPLC eluting with acetonitrile/water to afford 220 mg of 2-(2-bromo-5-methoxy-1H-pyrrolo[3,2-b]pyridin-3-yl)acetic acid. Dissolved 200 mg of the above acid (0.7 mmol) and (S)-methyl 3-(3-allylphenyl)-2-aminopropanoate hydrochloride (197 mg, 0.77 mmol) in 5 mL of DMF and to it was added N,N-diisopropylethylamine (366 µL, 2.1 mmol). The reaction mixture was cooled down to 0° C. and to it was added HATU (319 mg, 8.4 mmol), and then it was allowed to stir at ambient temperature for 20 minutes. The reaction mixture was purified by RP HPLC eluting with acetonitrile/water (with 0.1% TFA) to afford 210 mg (0.43 mmol) of (S)-methyl 3-(3-allylphenyl)-2-(2-(2-bromo-5-methoxy-1H-pyrrolo[3,2-b]pyridin-3-yl)acetamido)propanoate which was dissolved in 5 mL of CH$_2$Cl$_2$ and cooled down to 0° C. To it were added N,N-diisopropylethylamine (0.15 mL, 0.86 mmol), di-tert-butyl carbonate (113 mg, 0.86 mmol) and 4-dimethylaminopyridine (5.2 mg, 0.04 mmol). The resulting mixture was allowed to stir for 5 minutes and then partitioned between ethyl acetate and water. The organic layer was separated and washed with brine, dried over MgSO$_4$, filtered and the filtrate was concentrated to dryness. It was purified by silica gel chromatography eluting with EtOAc/hexanes) to afford 230 mg of (S)-tert-butyl 3-(2-(3-(3-allylphenyl)-1-methoxy-1-oxopropan-2-ylamino)-2-oxoethyl)-2-bromo-5-methoxy-1H-pyrrolo[3,2-b]pyridine-1-carboxylate MS (m/z): 586.0 [M+H]+; HPLC retention time 4.86 min (5-99% acetonitrile:water with 0.05% formic acid).

Preparation of methyl (6E,15S)-2-methoxy-17-oxo-8,14,15,16,17,18-hexahydro-5H-13,9-(metheno)pyrido[2',3':4,5]pyrrolo[3,2-d]azacyclopentadecine-15-carboxylate Under a nitrogen atmosphere, (5)-tert-butyl 3-(2-(3-(3-allylphenyl)-1-methoxy-1-oxopropan-2-ylamino)-2-oxoethyl)-2-bromo-5-methoxy-1H-pyrrolo[3,2-b]pyridine-1-carboxylate (220 mg, 0.37 mmol), palladium acetate (8.3 mg, 0.037 mmol), 2-di-tert-butylphosphino-2'-(N,N-dimethylamino) biphenyl (25.2 mg, 0.074 mmol), triethylamine (309 µL, 2.22 mmol) and DMF (150 mL) were mixed and purged with N$_2$. The reaction mixture was heated to 120° C. for 5 hours. The reaction was allowed to cool to ambient temperature and then most of the solvent was removed. It was then partitioned between ethyl acetate and water. The organic layer was separated and washed with 5% aqueous LiCl and brine, dried over MgSO$_4$, filtered and concentrated to afford crude product which was purified by RP HPLC eluting with acetonitrile and water (with 0.1% TFA) to afford 50 mg of methyl (6E,15S)-2-methoxy-17-oxo-8,14,15,16,17,18-hexahydro-5H-13,9-(metheno)pyrido[2',3':4,5]pyrrolo[3,2-d]azacyclopentadecine-15-carboxylate. MS (m/z): 406.2 [M+H]+; HPLC retention time 2.39 min (5-99% acetonitrile:water with 0.05% formic acid).

Preparation of (6E,15S)—N-(4-chlorophenyl)-2-methoxy-N-methyl-17-oxo-8,14,15,16,17,18-hexahydro-5H-13,9-(metheno)pyrido[2',3':4,5]pyrrolo[3,2-d]azacyclopentadecine-15-carboxamide Methyl (6E,15S)-2-methoxy-17-oxo-8,14,15,16,17,18-hexahydro-5H-13,9-(metheno)pyrido[2',3':4,5]pyrrolo[3,2-d]azacyclopentadecine-15-carboxylate (33 mg, 0.08 mmol) was dissolved in 2 mL of THF/MeOH/H$_2$O (3/2/1), and to it was added LiOH.H$_2$O (10 mg, 0.24 mmol). The reaction mixture was allowed to stir at ambient temperature for 0.5 hour and then purified by RP HPLC eluting with acetonitrile/water (with 0.1% TFA) to afford 24 mg of the acid (0.06 mmol). It was dissolved in 1 mL of DMF and to it were added 4-chloro-N-methylaniline (8.2 μL, 0.066 mmol) and N,N-diisopropylethylamine (31 μL, 0.18 mmol). The reaction mixture was cooled down to 0° C. and to it was added HATU (27 mg, 0.072 mmol). It was allowed to stir at ambient temperature overnight and then was purified by RP HPLC eluting with acetonitrile and water (with 0.1% TFA) to afford 22 mg of (6E,15S)—N-(4-chlorophenyl)-2-methoxy-N-methyl-17-oxo-8,14,15,16,17,18-hexahydro-5H-13,9-(metheno)pyrido[2',3':4,5]pyrrolo[3,2-d]azacyclopentadecine-15-carboxamide. MS (m/z): 514.8 [M+H]+; HPLC retention time 3.02 min (5-99% acetonitrile:water with 0.05% formic acid).

Preparation of (15S)—N-(4-chlorophenyl)-N-methyl-2,17-dioxo-1,5,6,7,8,14,15,16,17,18-decahydro-2H-13,9-(metheno)pyrido[2',3':4,5]pyrrolo[3,2-d]azacyclopentadecine-15-carboxamide (6E,15S)—N-(4-chlorophenyl)-2-methoxy-N-methyl-17-oxo-8,14,15,16,17,18-hexahydro-5H-13,9-(metheno)pyrido[2',3':4,5]pyrrolo[3,2-d]azacyclopentadecine-15-carboxamide (20 mg) was dissolved in 10 mL of ethyl acetate and purged with nitrogen. Rhodium (5 wt. % on alumina powder, 10 mg) was added. The reaction mixture was purged with hydrogen and stirred at ambient temperature overnight under a hydrogen balloon. After completion of the reaction, the reaction mixture was filtered and washed with ethyl acetate. The filtrate was concentrated and purified by RP HPLC eluting with acetonitrile/water (with 0.1% TFA) to afford 10 mg of the product which was dissolved in 1 mL of acetic acid, and to it was added KI (12 mg). The reaction mixture was heated up to 100° C. for two hours and then cooled down to ambient temperature. The solvent was removed and the residue was purified by RP HPLC eluting with acetonitrile and water (with 0.1% TFA) to afford 2.3 mg of (15S)—N-(4-chlorophenyl)-N-methyl-2,17-dioxo-1,5,6,7,8,14,15,16,17,18-decahydro-2H-13,9-(metheno)pyrido[2',3':4,5]pyrrolo[3,2-d]azacyclopentadecine-15-carboxamide. $^1$H NMR (400 MHz, CD$_3$OD, ppm) δ 8.01 (d, J=10.0 Hz, 1H), 7.51 (m, 3H), 7.38 (d, J=8.1 Hz, 2H), 7.14 (s, 1H), 6.65 (t, J=7.6 Hz, 1H), 6.48 (d, J=7.7 Hz, 1H), 6.27 (d, J=7.1 Hz, 1H), 6.10 (d, J=9.1 Hz, 1H), 4.52 (m, 1H), 3.55 (m, 1H), 3.39 (m, 1H), 3.30 (s, 3H), 3.14 (m, 1H), 2.82 (m, 1H), 2.63 (m, 2H), 1.44 (m, 4H). MS (m/z): 503.1[M+H]+; HPLC retention time 2.89 min (5-99% acetonitrile:water with 0.05% formic acid).

Example 31

Preparation of Compound 31

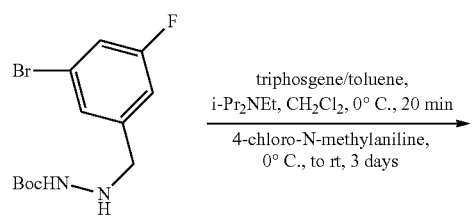

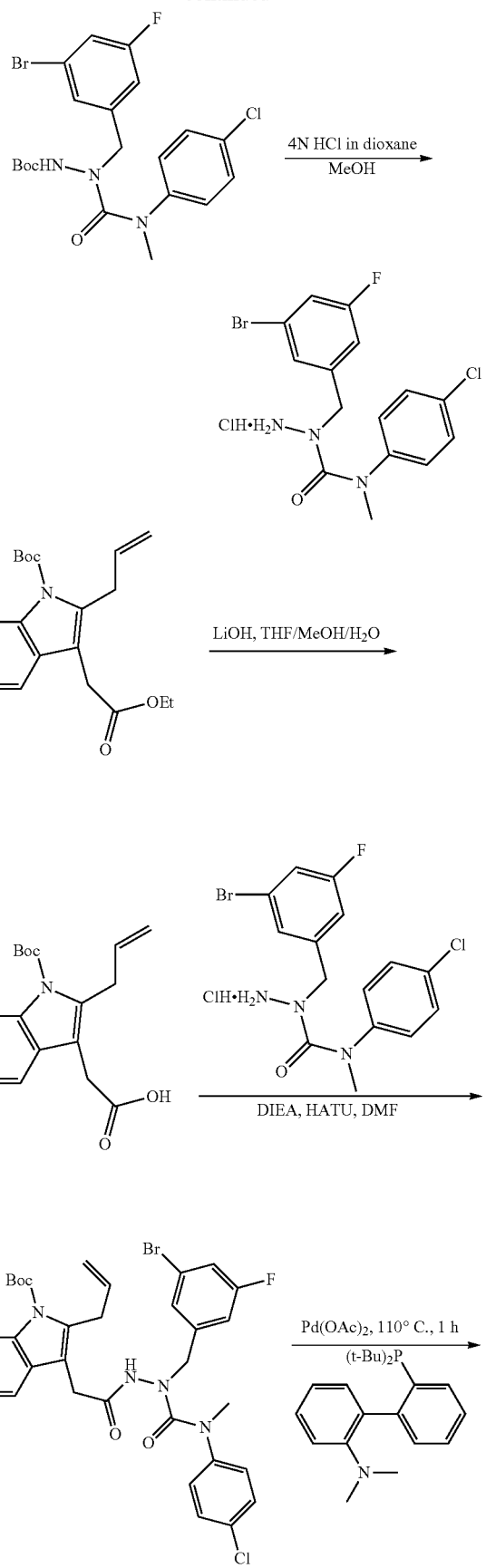

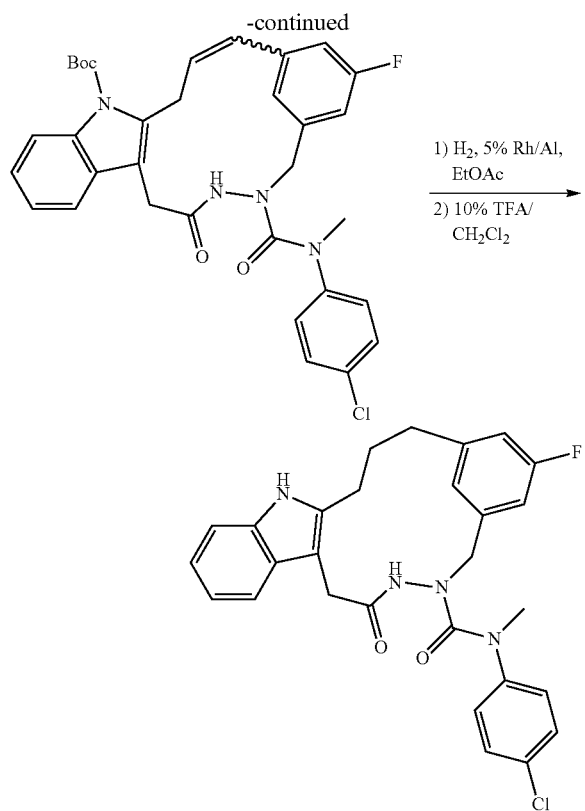

Preparation of 1-(3-bromo-5-fluorobenzyl)-N-(4-chlorophenyl)-N-methylhydrazinecarboxamide hydrochloride Triphosgene (593 mg, 2.0 mmol) was dissolved in 13 mL of methylene chloride and cooled to 0° C. To it was added a solution of tert-butyl 2-(3-bromo-5-fluorobenzyl)hydrazinecarboxylate (1.6 g, 5 mmol) and N,N-diisopropylethylamine (1.3 mL, 7.5 mmol) in 13 mL of methylene chloride. The reaction mixture was allowed to stir at 0° C. for 20 min, and to it was added a solution of 4-chloro-N-methylaniline (726 µL, 6 mmol) in 4 mL of methylene chloride. The resulting mixture was allowed to stir at ambient temperature for 3 days. It was diluted with methylene chloride and washed with 1N HCl, half saturated NaHCO$_3$ and half brine, then dried over MgSO$_4$, filtered and concentrated. The residue was purified by silica gel chromatography eluting with ethyl acetate and hexanes to afford 359 mg of tert-butyl 2-(3-bromo-5-fluorobenzyl)-2-((4-chlorophenyl)(methyl)carbamoyl)hydrazinecarboxylate (0.74 mmol). It was then dissolved in 2 mL of methanol, and to it was added 4N HCl in 1,4-dioxane (0.9 mL, 3.7 mmol). The mixture was stirred at ambient temperature overnight. The solvent was removed to afford 1-(3-bromo-5-fluorobenzyl)-N-(4-chlorophenyl)-N-methylhydrazinecarboxamide hydrochloride. MS (m/z): 387.9 [M+H]$^+$; HPLC retention time 3.88 min (5-99% acetonitrile:water with 0.05% formic acid).

Preparation of tert-butyl 2-allyl-3-(2-(2-(3-bromo-5-fluorobenzyl)-2-((4-chlorophenyl)(methyl)carbamoyl)hydrazinyl)-2-oxoethyl)-1H-indole-1-carboxylate tert-Butyl 2-allyl-3-(2-ethoxy-2-oxoethyl)-1H-indole-1-carboxylate (300 ma, 0.87 mmol) was dissolved in 6 mL of THF/MeOH/H$_2$O (3/2/1) and to it was added LiOH.H$_2$O (110 mg, 2.6 mmol). The reaction mixture was allowed to stir at ambient temperature for 20 minutes. The reaction mixture was cooled to 0° C. and acidified with 1N (aq) HCl. The reaction mixture was extracted with ethyl acetate and the organic layer was separated and dried over MgSO$_4$. The mixture was filtered and concentrated to afford 260 mg of 2-(2-allyl-1-(tert-butoxycarbonyl)-1H-indol-3-yl) acetic acid. The acid from the step above (260 mg, 0.82 mmol) was dissolved in 4 mL of DMF, and to it were added 1-(3-bromo-5-fluorobenzyl)-N-(4-chlorophenyl)-N-methylhydrazinecarboxamide hydrochloride (0.74 mmol) and N,N-diisopropylethylamine (427 µL, 2.5 mmol). The reaction mixture was cooled to 0° C. and HATU (343 mg, 0.9 mmol) was added. The reaction mixture was allowed to stir at ambient temperature for two hours and then was partitioned between ethyl acetate and water. The organic layer was separated and washed with 5% aqueous LiCl, saturated aqueous NaHCO$_3$ and brine. The organic layer was then dried over MgSO$_4$, filtered and concentrated to afford crude product which was purified by silica gel chromatography eluting with ethyl acetate/hexanes to afford 418 mg of tert-butyl 2-allyl-3-(2-(2-(3-bromo-5-fluorobenzyl)-2-(4-chlorophenyl)(methyl)carbamoyl)hydrazinyl)-2-oxoethyl)-1H-indole-1-carboxylate as a white solid. MS (m/z): 685.1 [M+H]+; HPLC retention time 5.14 min (5-99% acetonitrile:water with 0.05% formic acid).

Preparation of N-(4-chlorophenyl)-8-fluoro-N-methyl-2-oxo-2,3,11,12,13,14-hexahydro-1H-6,10-(metheno)[1,2]diazacyclopentadecino[6,5-b]indole-4(5H)-carboxamide Under a nitrogen atmosphere, tert-butyl 2-allyl-3-(2-(2-(3-bromo-5-fluorobenzyl)-2-(4-chlorophenyl)(methyl)carbamoyl)hydrazinyl)-2-oxoethyl)-1H-indole-1-carboxylate (220 mg, 0.32 mmol), palladium acetate (5 mg), 2-di-tert-butylphosphino-2'-(N,N-dimethylamino) biphenyl (5 mg), triethylamine (13 mL) and acetonitrile (90 mL) mixed in a pressure reaction vessel and heated to 110° C. for one hour. The reaction was allowed to cool to ambient temperature and was partitioned between ethyl acetate and water. The organic layer was separated and washed with 0.5 N HCl and brine. The organic layer was then dried over MgSO$_4$, filtered and concentrated to afford crude product which was purified by RP HPLC eluting with acetonitrile/water (with 0.1% TFA) to afford 45.5 mg of tert-butyl (11Z)-4-[(4-chlorophenyl)(methyl)carbamoyl]-8-fluoro-2-oxo-1,2,3,4,5,13-hexahydro-14H-6,10-(metheno)[1,2]diazacyclopentadecino[6,5-b]indole-14-carboxylate 20 mg of the tert-butyl (11Z)-4-[(4-chlorophenyl)(methyl)carbamoyl]-8-fluoro-2-oxo-1,2,3,4,5,13-hexahydro-14H-6,10-(metheno)[1,2]diazacyclopentadecino[6,5-b]indole-14-carboxylate was dissolved in 10 mL of EtOAc and purged with nitrogen. Rhodium (5 wt. % on alumina powder, 10 mg) was added. The reaction mixture was purged with hydrogen and stirred at ambient temperature overnight under a hydrogen balloon. After completion of the reaction, the mixture was filtered and washed with ethyl acetate. The filtrate was concentrated and the product was dissolved in 2 mL of 10% TFA/CH$_2$Cl$_2$ and purified and stirred at ambient temperature for one hour. The solvent was removed and the residue was purified by reverse phase HPLC eluting with acetonitrile/water (with 0.1% TFA) to afford N-(4-chlorophenyl)-8-fluoro-N-methyl-2-oxo-2,3,11,12,13,14-hexahydro-1H-6,10-(metheno)[1,2]diazacyclopentadecino[6,5-b]indole-4(5H)-carboxamide. $^1$H NMR (400 MHz, CDCl$_3$, ppm) δ 7.83 (s, 1H), 7.29 (d, J=8.7 Hz, 2H), 7.22 (d, J=6.7 Hz, 1H), 7.10-6.94 (m, 5H), 6.70 (t, J=8.6 Hz, 2H), 6.22 (s, 1H), 5.99 (s, 1H), 4.51 (br, 1H), 4.23 (br, 1H), 3.22 (s, 3H), 3.08 (br, 1H), 2.85 (br, 1H), 2.73-1.96 (m, 6H). MS (m/z): 505.2 [M+H]+; HPLC retention time 4.01 min (2-98% acetonitrile: water with 0.05% formic acid).

Example 32

Preparation of Compound 32

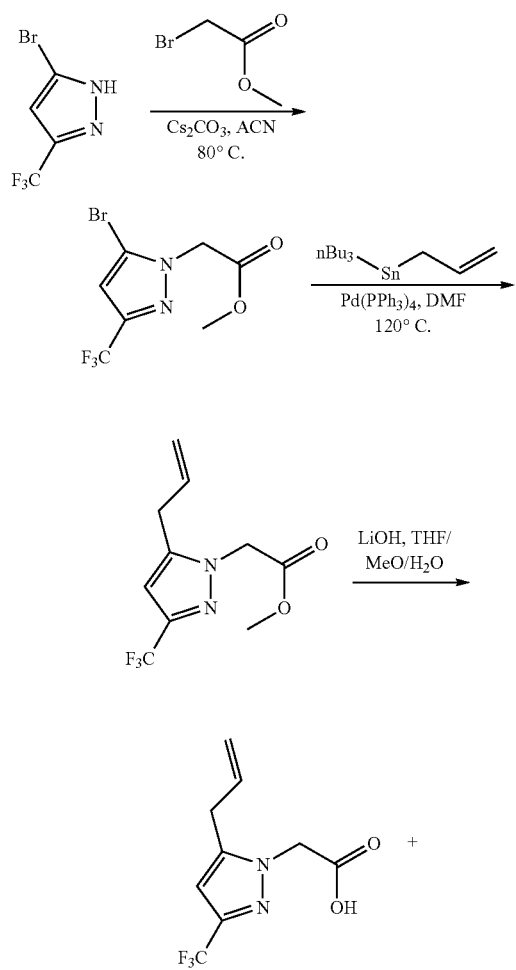

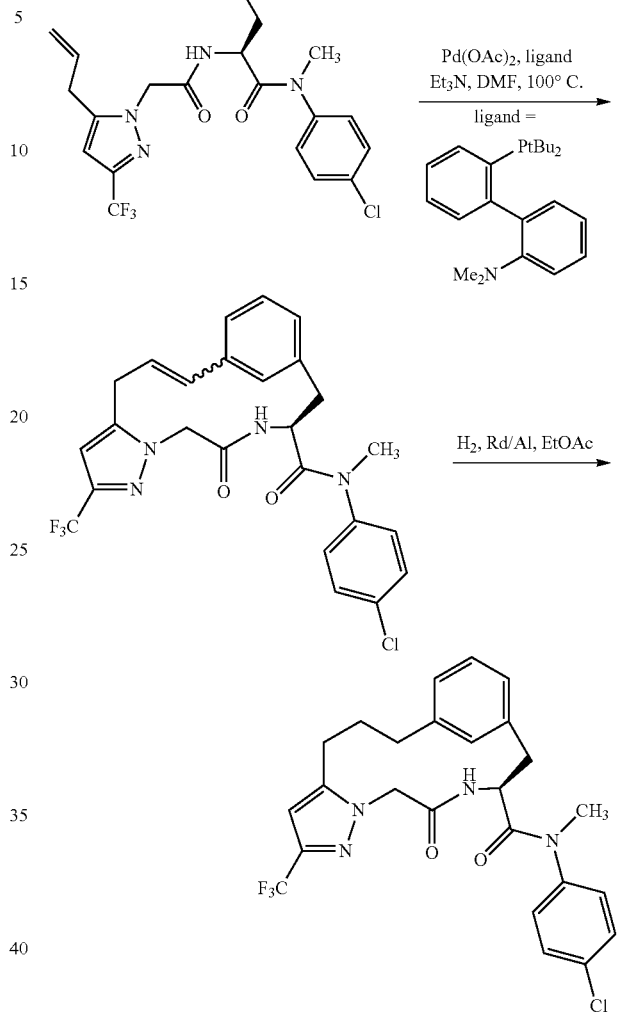

32

Synthesis of methyl 2-(5-bromo-3-(trifluoromethyl)-1H-pyrazol-1-yl)acetate

Preparation of 2-(5-bromo-3-(trifluoromethyl)-1H-pyrazol-1-yl)acetate

To a solution of 5-bromo-3-(trifluoromethyl)-1H-pyrazole (1.0 g, 4.6 mmol) and $Cs_2CO_3$ (3.0 g, 9.3 mmol) in acetonitrile (10 mL) was added methyl 2-bromoacetate (865 mg, 5.6 mmol). The reaction was heated at 80° C. for 3 h. After the reaction was cooled to room temperature, the mixture was portioned between ethyl acetate and water. The organic layer was separated and washed with saturated aqueous $NH_4Cl$ and brine. The organic layer was then dried over $Na_2SO_4$, filtered and concentrated to afford crude product which was purified by silica gel chromatography eluting with dichloromethane/hexanes to afford methyl 2-(5-bromo-3-(trifluoromethyl)-1H-pyrazol-1-yl)acetate (420 mg, 32%) as a clear oil. MS (m/z): 287.1 [M+H]+; HPLC retention time 2.93 min (2-98% acetonitrile:water with 0.05% trifluoroacetic acid).

Preparation of methyl 2-(5-allyl-3-(trifluoromethyl)-1H-pyrazol-1-yl)acetate Methyl 2-(5-bromo-3-(trifluoromethyl)-1H-pyrazol-1-yl)acetate (420 mg, 1.47 mmol), tri n-butyl allyltin (729 mg, 2.20 mmol) and tetrakis(triphenylphosphine)palladium(0) (50 mg, 0.043 mmol) were dissolved in DMF (10 mL). The solution was degassed with argon for 10 min and then heated at 120° C. overnight. After the solution was cooled to room temperature, the volatiles were removed under vacuum. The resulting residue was purified by silica gel chromatography (loading with toluene, eluting with dichloromethane/hexanes) to afford methyl 2-(5-allyl-3-(trifluoromethyl)-1H-pyrazol-1-yl)acetate (140 mg, 38%) as a clear oil. MS (m/z): 249.1 [M+H]+; HPLC retention time 3.51 min (2-98% acetonitrile:water with 0.05% trifluoroacetic acid).

Preparation of 2-(5-allyl-3-(trifluoromethyl)-1H-pyrazol-1-yl)acetic acid

Methyl 2-(5-allyl-3-(trifluoromethyl)-1H-pyrazol-1-yl)acetate (120 mg, 0.48 mmol) was dissolved in THF (1 mL). To this solution was added lithium hydroxide monohydrate (70 mg) in water (1 mL) and MeOH (0.1 mL). The resulting solution was stirred at room temperature overnight. Upon completion of the reaction, the product was purified by reverse phase HPLC eluting with acetonitrile/water (with 0.1% TFA) to afford 2-(5-allyl-3-(trifluoromethyl)-1H-pyrazol-1-yl)acetic acid (110 mg, 99%) as an oil. MS (m/z): 235.3 [M+H]+; HPLC retention time 3.03 min (2-98% acetonitrile:water with 0.05% trifluoroacetic acid).

Preparation of (S)-2-(2-(5-allyl-3-(trifluoromethyl)-1H-pyrazol-1-yl)acetamido)-3-(3-bromophenyl)-N-(4-chlorophenyl)-N-methylpropanamide)

To a solution of methyl 2-(5-allyl-3-(trifluoromethyl)-1H-pyrazol-1-yl)acetate (110 mg, 0.48 mmol) and (S)-2-amino-3-(3-bromophenyl)-N-(4-chlorophenyl)-N-methylpropanamide (194 mg, 0.48 mmol) in DMF (2 mL) was added HATU (228 mg, 0.6 mmol) and DIEA (193 mg, 1.5 mmol). Upon completion of the reaction, the product was purified by reverse phase HPLC eluting with acetonitrile/water (with 0.1% TFA) to afford (S)-2-(2-(5-allyl-3-(trifluoromethyl)-1H-pyrazol-1-yl)acetamido)-3-(3-bromophenyl)-N-(4-chlorophenyl)-N-methylpropanamide (68 mg, 24%) as a solid. MS (m/z): 582.9 [M+H]+; HPLC retention time 4.52 min (2-98% acetonitrile:water with 0.05% trifluoroacetic acid).

Preparation of the Pyrazole Macrocycle

Under a nitrogen atmosphere, (S)-2-(2-(5-allyl-3-(trifluoromethyl)-1H-pyrazol-1-yl)acetamido)-3-(3-bromophenyl)-N-(4-chlorophenyl)-N-methylpropanamide (45 mg, 0.076 mmol), palladium acetate (1.7 mg, 0.076 mmol), 2-di-tert-butylphosphino-2'-(N,N-dimethylamino)biphenyl (5.2 mg, 0.015 mmol), triethylamine (85 µL) and DMF (27 mL) were mixed in a microwave vessel which was sealed and purged with $N_2$. The vial was heated to 120° C. overnight. The reaction was allowed to cool to ambient temperature and the product was purified by reverse phase HPLC eluting with acetonitrile/water (with 0.1% TFA) as a mixture of stereoisomers which were used in the next step. The product from last step was dissolved in EtOAc (10 mL). To this solution was added Rd/Al (10 mg) and the reaction was stirred under 1 atm $H_2$ at room temperature. Upon completion of the reaction, the volatiles were removed in vacuo and the product was purified by reverse phase HPLC eluting with acetonitrile/water (with 0.1% TFA) to afford the pyrazole macrocycle (5.9 mg, 15% two steps) as a solid. $^1$H NMR (400 MHz, CDCl$_3$) δ 7.43 (d, J=8 Hz, 2H), 7.20 (d, J=8.8 Hz, 2H), 7.04 (t, J=7.6 Hz, 1H), 6.88 (d, J=7.6 Hz, 1H), 6.38 (m, 2H), 6.30 (d, J=9.2 Hz, 1H), 6.03 (s, 1H), 4.72 (d, J=16 Hz, 1H), 4.65 (m, 1H), 4.29 (d, J=16.8 Hz, 1H), 3.22 (s, 3H), 2.76 (m, 1H), 2.65 (m, 2H), 2.39 (d, J=11.6 Hz, 1H), 2.32 (m, 1H), 1.87 (m, 3H). MS (m/z): 505.2 [M+H]+; HPLC retention time 4.21 min (2-98% acetonitrile:water with 0.05% trifluoroacetic acid).

Example 33

The following illustrate representative pharmaceutical dosage forms, containing a compound of formula I ('Compound X'), for therapeutic or prophylactic use in humans.

| (i) Tablet 1 | mg/tablet |
| --- | --- |
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
| --- | --- |
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
| --- | --- |
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
| --- | --- |
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
| --- | --- |
| Compound X = (free acid form) | 10.0 |
| Monobasic sodium phosphate | 0.3 |

| (v) Injection 2 (10 mg/ml) | mg/ml |
|---|---|
| Dibasic sodium phosphate | 1.1 |
| Polyethylene glycol 400 | 200.0 |

1.0 N Sodium hydroxide solution
(pH adjustment to 7.0-7.5) q.s.
Water for injection q.s. ad 1 mL

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All references, including publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

The use of the terms "a" and "an" and "the" and similar references in the context of this disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., such as, preferred, preferably) provided herein, is intended merely to further illustrate the content of the disclosure and does not pose a limitation on the scope of the claims. No language in the specification should be construed as indicating any non-claimed element as essential to the practice of the present disclosure.

Alternative embodiments of the claimed disclosure are described herein, including the best mode known to the inventors for practicing the claimed invention. Of these, variations of the disclosed embodiments will become apparent to those of ordinary skill in the art upon reading the foregoing disclosure. The inventors expect skilled artisans to employ such variations as appropriate (e.g., altering or combining features or embodiments), and the inventors intend for the invention to be practiced otherwise than as specifically described herein.

Accordingly, this invention includes all modifications and equivalents of the subject matter recited in the claims appended hereto as permitted by applicable law. Moreover, any combination of the above described elements in all possible variations thereof is encompassed by the invention unless otherwise indicated herein or otherwise clearly contradicted by context.

The use of individual numerical values is stated as approximations as though the values were preceded by the word "about" or "approximately." Similarly, the numerical values in the various ranges specified in this application, unless expressly indicated otherwise, are stated as approximations as though the minimum and maximum values within the stated ranges were both preceded by the word "about" or "approximately." In this manner, variations above and below the stated ranges can be used to achieve substantially the same results as values within the ranges. As used herein, the terms "about" and "approximately" when referring to a numerical value shall have their plain and ordinary meanings to a person of ordinary skill in the art to which the disclosed subject matter is most closely related or the art relevant to the range or element at issue. The amount of broadening from the strict numerical boundary depends upon many factors. For example, some of the factors which may be considered include the criticality of the element and/or the effect a given amount of variation will have on the performance of the claimed subject matter, as well as other considerations known to those of skill in the art. As used herein, the use of differing amounts of significant digits for different numerical values is not meant to limit how the use of the words "about" or "approximately" will serve to broaden a particular numerical value or range. Thus, as a general matter, "about" or "approximately" broaden the numerical value. Also, the disclosure of ranges is intended as a continuous range including every value between the minimum and maximum values plus the broadening of the range afforded by the use of the term "about" or "approximately." Thus, recitation of ranges of values herein are merely intended to serve as a shorthand method of referring individually to each separate value falling within the range, unless otherwise indicated herein, and each separate value is incorporated into the specification as if it were individually recited herein.

It is to be understood that any ranges, ratios and ranges of ratios that can be formed by, or derived from, any of the data disclosed herein represent further embodiments of the present disclosure and are included as part of the disclosure as though they were explicitly set forth. This includes ranges that can be formed that do or do not include a finite upper and/or lower boundary. Accordingly, a person of ordinary skill in the art most closely related to a particular range, ratio or range of ratios will appreciate that such values are unambiguously derivable from the data presented herein.

What is claimed is:

1. A compound of formula I:

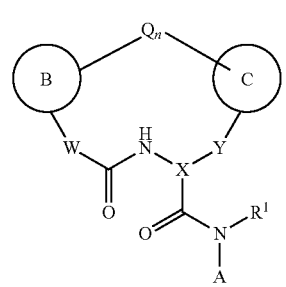

wherein:

A is $(C_6-C_{12})$aryl or aryl$(C_1-C_4)$alkyl- wherein any aryl or aryl$(C_1-C_4)$alkyl- of A is optionally substituted with 1, 2, 3, 4 or 5 $Z^1$ groups;

B is a monocyclic or bicyclic heteroaryl, wherein the heteroaryl of B has 2-10 carbon atoms and 1-5 heteroatoms selected from oxygen, nitrogen, and sulfur, and is optionally substituted with 1, 2, 3, 4 or 5 $Z^2$ groups, and wherein Q and W are connected to adjacent ring atoms of B;

C is phenyl, 5-membered heteroaryl or 6-membered heteroaryl, wherein any phenyl, 5-membered heteroaryl or 6-membered heteroaryl of C is optionally substituted with 1, 2, 3, or 4 $Z^3$ groups, and wherein the 5-membered heteroaryl or 6-membered heteroaryl of C has 1-6 carbon atoms and 1-4 heteroatoms selected from oxygen, nitrogen, and sulfur, and is monocyclic, and wherein Q and Y are connected to adjacent ring atoms of C, or Q and Y are connected to the first and third atom of three consecutive ring atoms of C;

each Q is independently selected from —C($R^{2a}$)$_2$—, —O—, —N$R^{1a}$—, —S—, —C(=O)—, —S(=O)— and —S(=O)$_2$—, or two adjacent Q groups taken together can be —C$R^{2b}$=C$R^{2b}$—;

W is —CH$_2$—;
X is CH or N;
Y is —CH$_2$—;
n is 1, 2, 3, 4 or 5;
$R^1$ is selected from (C$_1$-C$_6$)alkyl, (C$_3$-C$_7$)carbocycle, and (C$_3$-C$_7$)carbocycle(C$_1$-C$_6$)alkyl;
$R^{1a}$ is H or (C$_1$-C$_4$)alkyl, each $R^{2a}$ is independently H, halogen or (C$_1$-C$_4$)alkyl, and each $R^{2b}$ is independently H or (C$_1$-C$_4$)alkyl, or one $R^{2a}$ together with an adjacent Q group forms a three membered carbocycle;

each $Z^1$ is independently selected from (C$_1$-C$_4$)alkyl, (C$_2$-C$_4$)alkenyl, (C$_2$-C$_4$)alkynyl, halogen, —CN, —OR$_{n1}$, —OC(O)R$_{p1}$, —OC(O)NR$_{q1}$R$_{r1}$, —SR$_{n1}$, —S(O)R$_{p1}$, —S(O)$_2$OH, —S(O)$_2$R$_{p1}$, —S(O)$_2$NR$_{q1}$R$_{r1}$, —NR$_{q1}$R$_{r1}$, —NR$_{n1}$COR$_{p1}$, —NR$_{n1}$CO$_2$R$_{p1}$, —NR$_{q1}$R$_{r1}$, —NR$_{n1}$S(O)$_2$R$_{p1}$, —NR$_{n1}$S(O)$_2$OR$_{p1}$, —NR$_{n1}$S(O)$_2$NR$_{q1}$OR$_{r1}$, NO$_2$, —C(O)R$_{n1}$, —C(O)OR$_{n1}$ and —C(O)NR$_{q1}$R$_{r1}$, wherein any (C$_1$-C$_4$)alkyl, (C$_2$-C$_4$)alkenyl or (C$_2$-C$_4$)alkynyl of $Z^1$ is optionally substituted with 1, 2, 3, 4 or 5 $Z^{1a}$ groups;

each $Z^{1a}$ is independently selected from halogen, —CN, —OR$_{n2}$, —OC(O)R$_{p2}$, —OC(O)NR$_{q2}$R$_{r2}$, —SR$_{n2}$, (O)R$_{p2}$, —S(O)$_2$OH, (O)$_2$R$_{p2}$, (O)$_2$NR$_{q2}$R$_{r2}$, —NR$_{q2}$R$_{r2}$, —NR$_{n2}$COR$_{p2}$, —NR$_{n2}$CO$_2$R$_{p2}$, —NR$_{n2}$CONR$_{q2}$R$_{r2}$, —NR$_{n2}$S(O)$_2$R$_{p2}$, —NR$_{n2}$S(O)$_2$OR$_{p2}$, —NR$_{n2}$S(O)$_2$NR$_{q2}$R$_{r2}$, NO$_2$, —C(O)R$_{n2}$, —C(O)OR$_{n2}$ and —C(O)NR$_{q2}$R$_{r2}$;

each $Z^{1b}$ is independently selected from (C$_1$-C$_4$)alkyl, (C$_2$-C$_4$)alkenyl and (C$_2$-C$_4$)alkynyl;

each R$_{p1}$ is independently selected from H, (C$_1$-C$_4$)alkyl, (C$_2$-C$_4$)alkenyl, (C$_2$-C$_4$)alkynyl, wherein any (C$_1$-C$_4$)alkyl, (C$_2$-C$_4$)alkenyl or (C$_2$-C$_4$)alkynyl of R$_{n1}$ is optionally substituted with 1, 2, 3, 4 or 5 $Z^{1a}$ groups;

each R$_{p1}$ is independently selected from (C$_1$-C$_4$)alkyl, (C$_1$-C$_4$)haloalkyl, (C$_2$-C$_4$)alkenyl, (C$_2$-C$_4$)alkynyl wherein any (C$_1$-C$_4$)alkyl, (C$_2$-C$_4$)alkenyl or (C$_2$-C$_4$)alkynyl of R$_{p1}$ is optionally substituted with 1, 2, 3, 4 or 5 $Z^{1a}$ groups;

R$_{q1}$ and R$_{r1}$ are each independently selected from H, (C$_1$-C$_4$)alkyl, (C$_2$-C$_4$)alkenyl, (C$_2$-C$_4$)alkynyl, wherein any (C$_1$-C$_4$)alkyl, (C$_2$-C$_4$)alkenyl or (C$_2$-C$_4$)alkynyl of R$_{q1}$ or R$_{r1}$ is optionally substituted with 1, 2, 3, 4 or 5 $Z^{1a}$ groups, or R$_{q1}$ and R$_{r1}$ together with the nitrogen to which they are attached form a 5, 6 or 7-membered heterocycle, wherein the 5, 6 or 7-membered heterocycle has 1 to 3 heteroatoms selected from the group consisting of oxygen, nitrogen and sulfur and is optionally substituted with 1, 2, 3, 4 or 5 $Z^{1a}$ or $Z^{1b}$ groups;

each R$_{n2}$ is independently selected from H, (C$_1$-C$_4$)alkyl, (C$_2$-C$_4$)alkenyl, (C$_2$-C$_4$)alkynyl, and (C$_1$-C$_4$)haloalkyl;

each R$_{p1}$ is independently selected from (C$_1$-C$_4$)alkyl, (C$_2$-C$_4$)alkenyl, (C$_2$-C$_4$)alkynyl, and (C$_1$-C$_4$)haloalkyl;

R$_{q2}$ and R$_{r2}$ are each independently selected from H, (C$_1$-C$_4$)alkyl, (C$_2$-C$_4$)alkenyl, (C$_2$-C$_4$)alkynyl, and (C$_1$-C$_4$)haloalkyl, or R$_{q2}$ and R$_{r2}$ together with the nitrogen to which they are attached form a 5, 6 or 7-membered heterocycle wherein the 5, 6 or 7-membered heterocycle has 1 to 3 heteroatoms selected from the group consisting of oxygen, nitrogen and sulfur;

each $Z^2$ is independently selected from (C$_1$-C$_4$)alkyl, (C$_2$-C$_4$)alkenyl, (C$_2$-C$_4$)alkynyl, halogen, —CN, —OR$_{n3}$, —OC(O)R$_{p3}$, —OC(O)NR$_{q3}$R$_{r3}$, —SR$_{n3}$, —S(O)R$_{p3}$, —S(O)$_2$OH, —S(O)$_2$R$_{p3}$, —S(O)$_2$NR$_{q3}$R$_{r3}$, —NR$_{q3}$R$_{r3}$, —NR$_{n3}$COR$_{p3}$, —NR$_{n3}$CO$_2$R$_{p3}$, —NR$_{n3}$CONR$_{q3}$R$_{r3}$, —NR$_{n3}$S(O)$_2$R$_{p3}$, —NR$_{n3}$S(O)$_2$OR$_{p3}$, —NR$_{n3}$S(O)$_2$NR$_{q3}$R$_{r3}$, NO$_2$, —C(O)R$_{n3}$, —C(O)OR$_{n3}$ and —C(O)NR$_{q3}$R$_{r3}$, wherein any (C$_1$-C$_4$)alkyl, (C$_2$-C$_4$)alkenyl or (C$_2$-C$_4$)alkynyl of $Z^2$ is optionally substituted with 1, 2, 3, 4 or 5 $Z^{2a}$ groups;

each $Z^{2a}$ is independently selected from halogen, —CN, —OR$_{n4}$, —OC(O)R$_{p4}$, —OC(O)NR$_{q4}$R$_{r4}$, —SR$_{n4}$, —S(O)R$_{p4}$, —S(O)$_2$OH, —S(O)$_2$R$_{p4}$, —S(O)$_2$NR$_{q4}$R$_{r4}$, —NR$_{q4}$R$_{r4}$, —NR$_{n4}$COR$_{p4}$, —NR$_{n4}$CO$_2$R$_{p4}$, —NR$_{n4}$CONR$_{q4}$R$_{r4}$, —NR$_{n4}$S(O)$_2$R$_{p4}$, —NR$_{n4}$S(O)$_2$OR$_{p4}$, —NR$_{n4}$S(O)$_2$NR$_{q4}$R$_{r4}$, NO$_2$, —C(O)R$_{n4}$, —C(O)OR$_{n4}$ and —C(O)NR$_{q4}$R$_{r4}$;

each $Z^{2b}$ is independently selected from (C$_1$-C$_4$)alkyl, (C$_2$-C$_4$)alkenyl and (C$_2$-C$_4$)alkynyl;

each R$_{n3}$ is independently selected from H, (C$_1$-C$_4$)alkyl, (C$_2$-C$_4$)alkenyl, (C$_2$-C$_4$)alkynyl, wherein any (C$_1$-C$_4$)alkyl, (C$_2$-C$_4$)alkenyl or (C$_2$-C$_4$)alkynyl of R$_{n3}$ is optionally substituted with 1, 2, 3, 4 or 5 $Z^{2a}$ groups;

each R$_{p3}$ is independently selected from (C$_1$-C$_4$)alkyl, (C$_1$-C$_4$)haloalkyl, (C$_2$-C$_4$)alkenyl, (C$_2$-C$_4$)alkynyl, wherein any (C$_1$-C$_4$)alkyl, (C$_2$-C$_4$)alkenyl or (C$_2$-C$_4$)alkynyl of R$_{p3}$ is optionally substituted with 1, 2, 3, 4 or 5 $Z^{2a}$ groups;

R$_{q3}$ and R$_{r3}$ are each independently selected from H, (C$_1$-C$_4$)alkyl, (C$_2$-C$_4$)alkenyl, (C$_2$-C$_4$)alkynyl, wherein any (C$_1$-C$_4$)alkyl, (C$_2$-C$_4$)alkenyl or (C$_2$-C$_4$)alkynyl of R$_{q3}$ or R$_{r3}$ is optionally substituted with 1, 2, 3, 4 or 5 $Z^{2a}$ groups, or R$_{q3}$ and R$_{r3}$ together with the nitrogen to which they are attached form a 5, 6 or 7-membered heterocycle, wherein the 5, 6 or 7-membered heterocycle has 1 to 3 heteroatoms selected from the group consisting of oxygen, nitrogen and sulfur is optionally substituted with 1, 2, 3, 4 or 5 $Z^{2a}$ or $Z^{2b}$ groups;

each R$_{n4}$ is independently selected from H, (C$_1$-C$_4$)alkyl, (C$_2$-C$_4$)alkenyl, (C$_2$-C$_4$)alkynyl, (C$_3$-C$_7$)carbocycle, and (C$_1$-C$_4$)haloalkyl;

each R$_{p4}$ is independently selected from (C$_1$-C$_4$)alkyl, (C$_2$-C$_4$)alkenyl, (C$_2$-C$_4$)alkynyl, (C$_3$-C$_7$)carbocycle, and (C$_1$-C$_4$)haloalkyl;

R$_{q4}$ and R$_{r4}$ are each independently selected from H, (C$_1$-C$_4$)alkyl, (C$_2$-C$_4$)alkenyl, (C$_2$-C$_8$)alkynyl, (C$_3$-C$_7$)carbocycle, and (C$_1$-C$_4$)haloalkyl, or R$_{q4}$ and R$_{r4}$ together with the nitrogen to which they are attached form a 5, 6 or 7-membered heterocycle wherein the 5, 6 or 7-membered heterocycle has 1 to 3 heteroatoms selected from the group consisting of oxygen, nitrogen or sulfur;

each $Z^3$ is independently selected from (C$_1$-C$_4$)alkyl, halogen, —CN, —OR$_{n5}$, —NR$_{n5}$COR$_{p5}$, —C(O)R$_{n5}$, and —C(O)NR$_{q5}$R$_{r5}$;

each R$_{n5}$ is independently selected from H, (C$_1$-C$_4$)alkyl, and (C$_1$-C$_4$)haloalkyl;

each R$_{p5}$ is independently selected from (C$_1$-C$_4$)alkyl, (C$_2$-C$_4$)alkenyl, (C$_2$-C$_4$)alkynyl, and (C$_1$-C$_4$)haloalkyl; and R$_{q5}$ and R$_{r5}$ are each independently selected from H, (C$_1$-C$_4$)alkyl, (C$_2$-C$_4$)alkenyl, (C$_2$-C$_4$)alkynyl, and (C$_1$-C$_4$)haloalkyl, or R$_{q5}$ and R$_{r5}$ together with the nitrogen to which they are attached form a 5, 6 or 7-membered heterocycle wherein the 5, 6 or 7-membered heterocycle has 1 to 3 heteroatoms selected from the group consisting of oxygen, nitrogen and sulfur;

or a pharmaceutically acceptable salt thereof.

2. The compound of claim 1, or a pharmaceutically acceptable salt thereof, wherein each Q is independently selected from —CH$_2$—S— and —S(=O)$_2$—, or two adjacent Q groups taken together are —CH=CH—.

3. The compound of claim 1, or a pharmaceutically acceptable salt thereof, wherein n is 2, 3 or 4.

4. The compound of claim 1, or a pharmaceutically acceptable salt thereof, wherein Q$_n$ is —CH=CHCH$_2$—, —(CH$_2$)$_2$—, —(CH$_2$)$_3$—, —(CH$_2$)$_4$—, —CH$_2$CH=CH—, —CH$_2$SCH$_2$—, —CH$_2$S(=O)$_2$CH$_2$—, —CH=CH—, —CH$_2$S(CH$_2$)$_2$—, —CH$_2$S(=O)$_2$(CH$_2$)$_2$—, —CH$_2$S—, —CH$_2$S(=O)$_2$—, —SCH$_2$— or —S(=O)$_2$CH$_2$—.

5. The compound of claim 1, or a pharmaceutically acceptable salt thereof, wherein X is CH.

6. The compound of claim 1, or a pharmaceutically acceptable salt thereof, wherein C is phenyl, 5-membered heteroaryl or 6-membered heteroaryl, wherein any phenyl, 5-membered heteroaryl or 6-membered heteroaryl of C is optionally substituted with 1, 2, 3, or 4 Z$^3$ groups, and wherein Q and Y are connected to adjacent ring atoms of C.

7. The compound of claim 1 which is a compound of formula Ic:

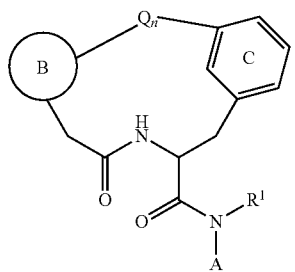

Ic wherein phenyl C is optionally substituted with 1, 2, 3, or 4 Z$^3$ groups, or a pharmaceutically acceptable salt thereof.

8. The compound of claim 1, or a pharmaceutically acceptable salt thereof, wherein each Z$^3$ is fluoro.

9. The compound of claim 1, or a pharmaceutically acceptable salt thereof, wherein R$^1$ is (C$_1$-C$_4$)alkyl.

10. The compound of claim 1, or a pharmaceutically acceptable salt thereof, wherein each Z$^1$ is independently selected from halogen and —O(C$_1$-C$_4$)alkyl.

11. The compound of claim 1, or a pharmaceutically acceptable salt thereof, wherein A is 4-methoxyphenyl, 4-chlorophenyl or benzyl.

12. The compound of claim 1, or a pharmaceutically acceptable salt thereof, wherein B is bicyclic-heteroaryl, wherein the bicyclic-heteroaryl has 2-10 carbon atoms and 1-5 heteroatoms and is optionally substituted with 1, 2, 3, 4 or 5 Z$^2$ groups.

13. The compound of claim 1, or a pharmaceutically acceptable salt thereof, wherein each Z$^2$ is independently selected from (C$_1$-C$_4$)alkyl, halogen, —OH and —O(C$_1$-C$_4$)alkyl, wherein (C$_1$-C$_4$)alkyl is optionally substituted with 1, 2, 3, 4 or 5 halogen.

14. The compound of claim 1, or a pharmaceutically acceptable salt thereof, wherein B is selected from:

wherein the wavy lines denote points of attachment of B to W and Q of the compound of formula I.

15. The compound of claim 1 selected from

101
-continued
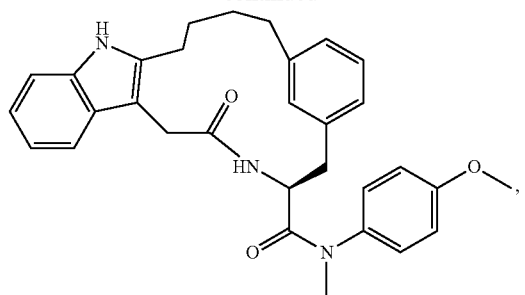
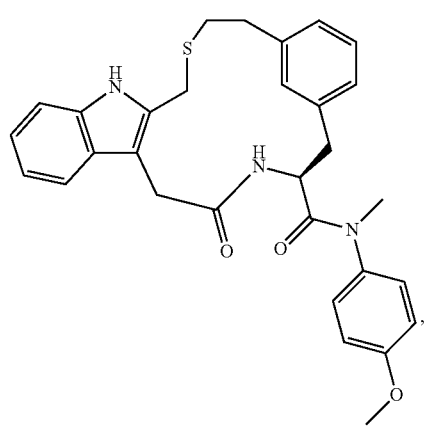
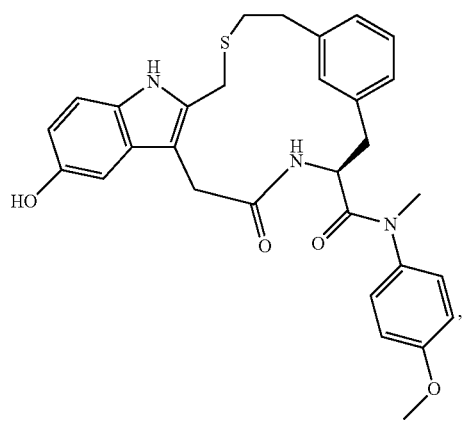
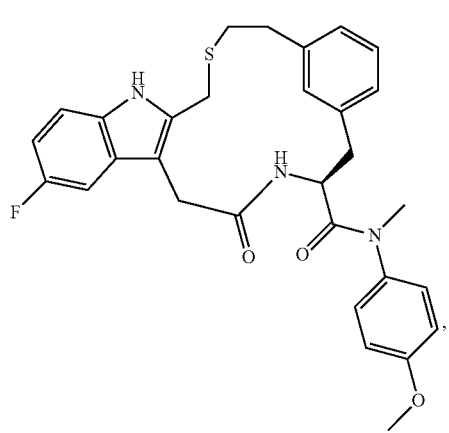
102
-continued
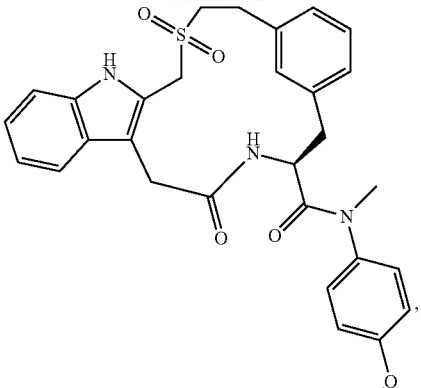
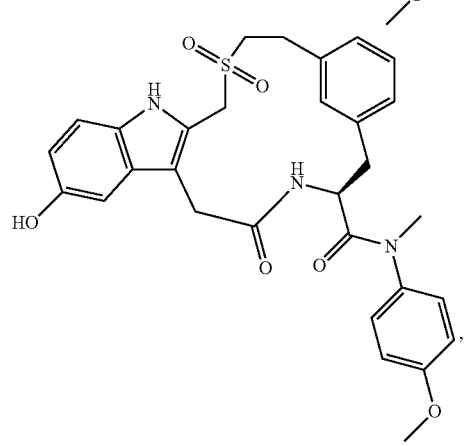
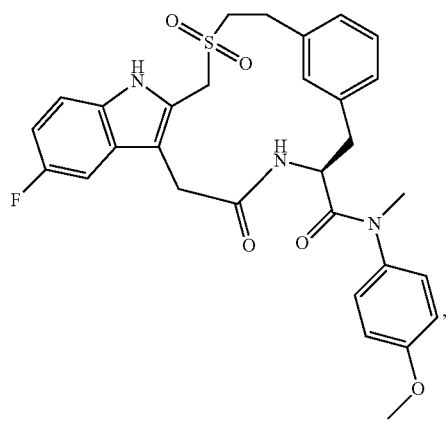
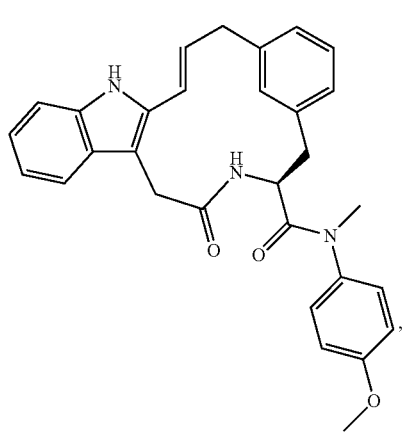

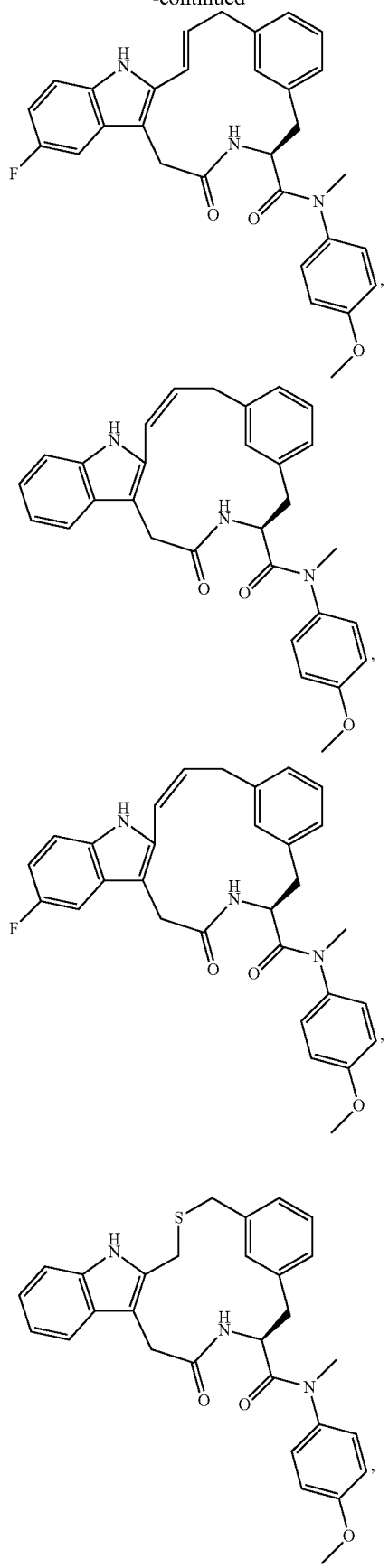
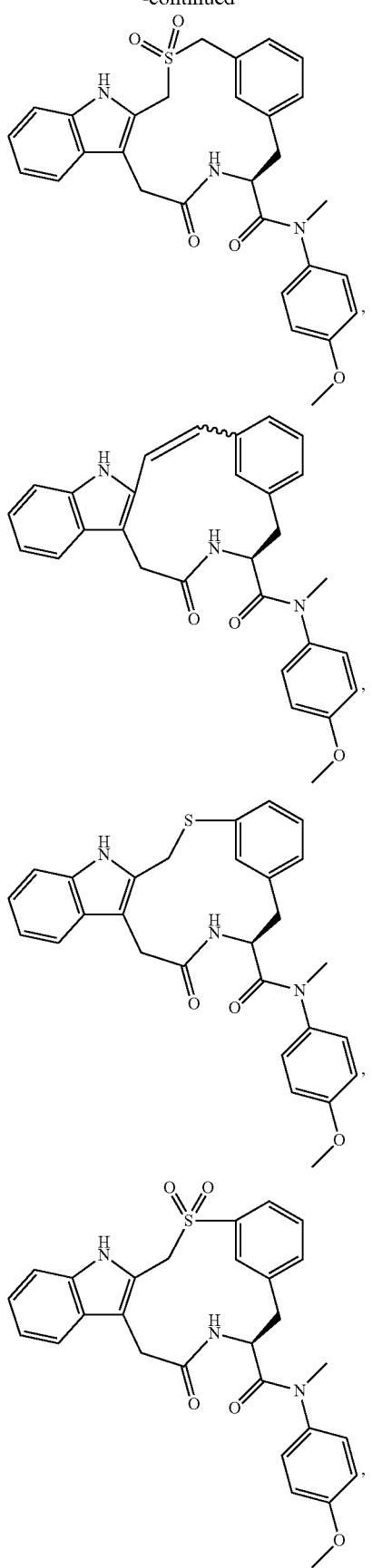

105
-continued
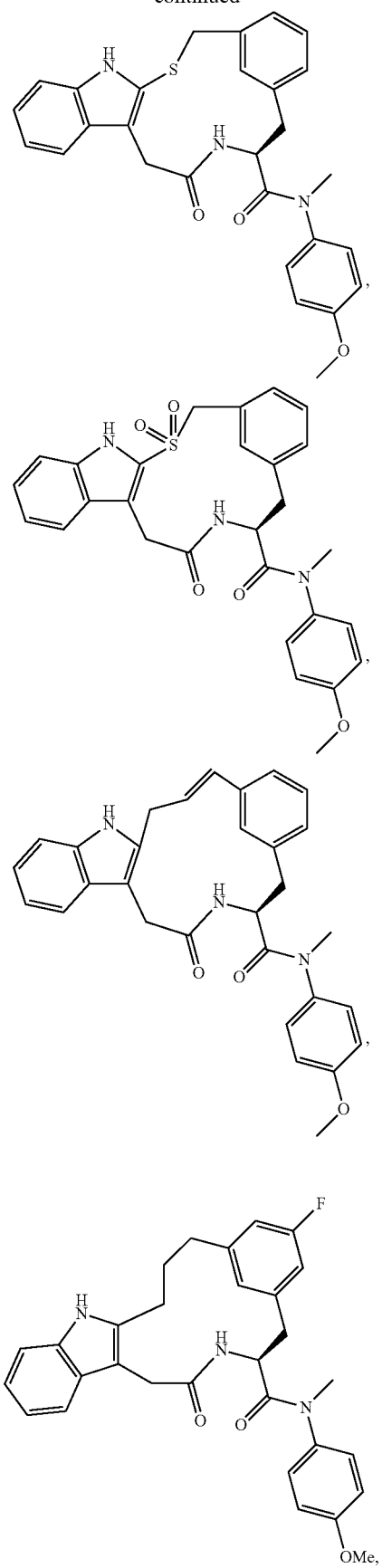
106
-continued
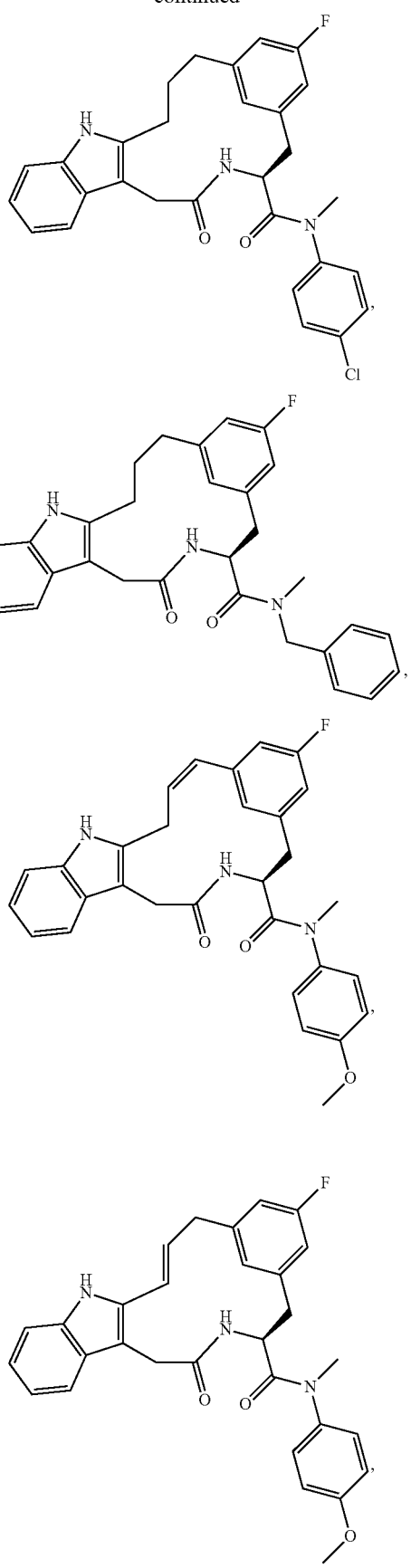

-continued

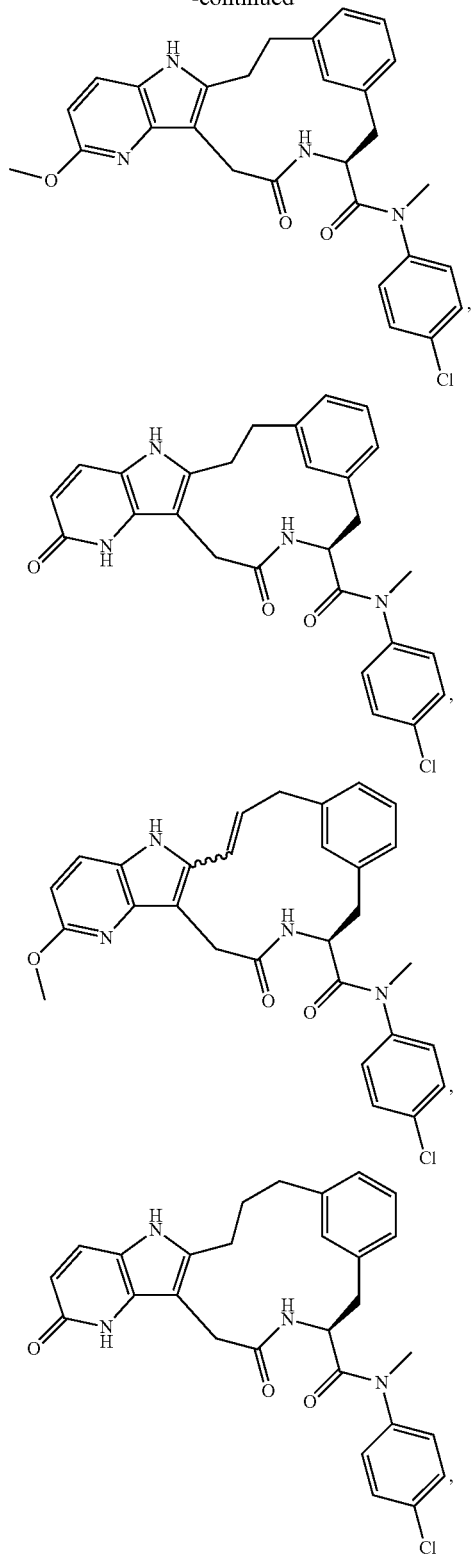

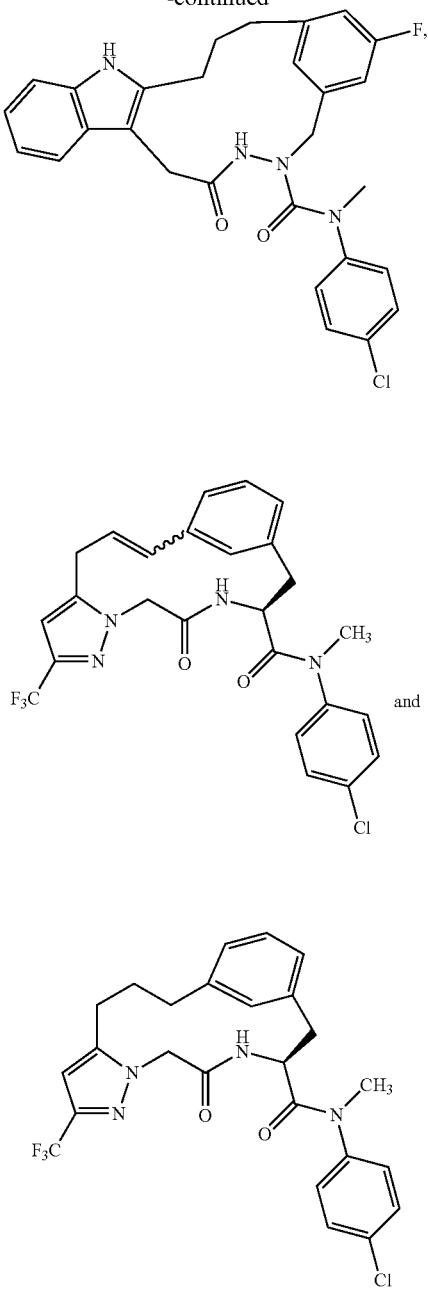

or a pharmaceutically acceptable salt thereof.

16. A pharmaceutical composition comprising a compound of claim 1, or a pharmaceutically acceptable salt thereof, and a pharmaceutically acceptable carrier.

17. A method for treating an HIV infection in a mammal comprising administering a compound of claim 1, or a pharmaceutically acceptable salt thereof, to the mammal.

* * * * *